US009026927B2

(12) United States Patent
Brumback et al.

(10) Patent No.: US 9,026,927 B2
(45) Date of Patent: May 5, 2015

(54) BIOMETRIC MONITORING DEVICE WITH CONTEXTUALLY- OR ENVIRONMENTALLY-DEPENDENT DISPLAY

(71) Applicant: Fitbit, Inc., San Francisco, CA (US)

(72) Inventors: Christine Boomer Brumback, San Francisco, CA (US); David Wayne Knight, San Francisco, CA (US); James Park, Berkeley, CA (US); Andrew Cole Axley, Oakland, CA (US); Shelten Gee Jao Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/045,574

(22) Filed: Oct. 3, 2013

(65) Prior Publication Data

US 2014/0176335 A1 Jun. 26, 2014

Related U.S. Application Data

(63) Continuation of application No. 14/029,763, filed on Sep. 17, 2013.

(60) Provisional application No. 61/789,305, filed on Mar. 15, 2013, provisional application No. 61/746,101, filed on Dec. 26, 2012.

(51) Int. Cl.
*G06F 3/048* (2013.01)
*A63B 24/00* (2006.01)
(Continued)

(52) U.S. Cl.
CPC ............ *G06F 3/0487* (2013.01); *A61B 5/0002* (2013.01); *G06F 3/0482* (2013.01);
(Continued)

(58) Field of Classification Search
CPC . G06F 3/04883; G06F 3/0483; G06F 3/0485; G06F 3/0487; G06F 1/1694; G06F 3/015; G06F 3/0346; G06F 19/3406; G06F 19/36; G06F 3/01; G06F 2200/1637; G06F 3/0482;
A61B 5/0002; A61B 5/0004; A61B 5/7475; A61B 5/681; A61B 5/7445; A61B 5/0015; A61B 5/02055; A63B 24/00–24/0087
USPC .......... 715/764, 810, 811, 813, 822, 825, 829, 715/832, 853, 854, 863, 864, 866; 340/870.16; 482/8, 9; 600/300, 301
See application file for complete search history.

(56) References Cited

U.S. PATENT DOCUMENTS

| 4,938,228 A | 7/1990 | Righter et al. |
| 5,339,294 A | 8/1994 | Rodgers |

(Continued)

FOREIGN PATENT DOCUMENTS

| EP | 1 721 237 | 8/2012 |
| WO | WO 2012/170366 | 12/2012 |

(Continued)

OTHER PUBLICATIONS

U.S. Appl. No. 14/029,759, filed Sep. 17, 2013, Park et al.

(Continued)

*Primary Examiner* — James T Durkin
(74) *Attorney, Agent, or Firm* — Weaver Austin Villeneuve & Sampson

(57) ABSTRACT

A biometric monitoring device with a display is provided. The display may, in response to receiving page advance requests from a user, advance through a plurality of different data display pages, at least some of which show aspects of biometric data recorded by the device. The biometric monitoring device may also, based on the biometric data, modify the sequential display order of the data display pages. In some implementations, a biometric monitoring device integrated into a wristband may be configured to turn a display of the biometric monitoring device on and display the time in response to biometric sensors of the biometric monitoring device detecting motion of the wearer's forearm consistent with moving the forearm into a watch-viewing position.

27 Claims, 22 Drawing Sheets

(51) Int. Cl.

| | | |
|---|---|---|
| A61B 5/00 | (2006.01) | |
| G06F 3/0487 | (2013.01) | |
| G06F 3/0482 | (2013.01) | |
| G06F 3/01 | (2006.01) | |
| G06F 19/00 | (2011.01) | |
| G06F 1/16 | (2006.01) | |
| G06F 3/0346 | (2013.01) | |
| A61B 5/0205 | (2006.01) | |

(52) U.S. Cl.
CPC .............. *A63B 24/00* (2013.01); *A61B 5/0015* (2013.01); *G06F 3/01* (2013.01); *G06F 19/36* (2013.01); *G06F 19/3406* (2013.01); *A61B 5/7445* (2013.01); *A61B 5/7475* (2013.01); *A61B 5/02055* (2013.01); *A61B 5/681* (2013.01); *G06F 1/1694* (2013.01); *G06F 3/015* (2013.01); *G06F 2200/1637* (2013.01); *G06F 3/0346* (2013.01)

(56) References Cited

U.S. PATENT DOCUMENTS

| | | | | |
|---|---|---|---|---|
| 5,612,931 | A * | 3/1997 | Sato et al. | 368/67 |
| 5,876,350 | A | 3/1999 | Lo et al. | |
| 5,946,274 | A | 8/1999 | Yamaguchi et al. | |
| 5,978,923 | A | 11/1999 | Kou | |
| 6,300,947 | B1 * | 10/2001 | Kanevsky | 715/866 |
| 6,469,718 | B1 * | 10/2002 | Setogawa et al. | 715/810 |
| 6,583,369 | B2 | 6/2003 | Montagnino et al. | |
| 6,888,927 | B1 | 5/2005 | Cruickshank et al. | |
| 7,155,729 | B1 | 12/2006 | Andrew et al. | |
| 7,254,516 | B2 | 8/2007 | Case, Jr. et al. | |
| 7,458,014 | B1 * | 11/2008 | Rubin et al. | 715/229 |
| 7,559,877 | B2 | 7/2009 | Parks et al. | |
| 7,662,065 | B1 | 2/2010 | Kahn et al. | |
| 7,793,361 | B2 | 9/2010 | Ishihara et al. | |
| 7,913,185 | B1 * | 3/2011 | Benson et al. | 715/808 |
| 8,162,804 | B2 * | 4/2012 | Tagliabue | 482/8 |
| 8,172,761 | B1 | 5/2012 | Rulkov et al. | |
| 8,180,591 | B2 * | 5/2012 | Yuen et al. | 702/160 |
| 8,306,508 | B1 | 11/2012 | Lundy et al. | |
| 8,365,073 | B2 * | 1/2013 | Kim et al. | 715/273 |
| 8,441,356 | B1 * | 5/2013 | Tedesco et al. | 340/573.1 |
| 8,600,457 | B2 | 12/2013 | Vargas et al. | |
| 8,734,296 | B1 | 5/2014 | Brumback et al. | |
| 8,784,271 | B2 | 7/2014 | Brumback et al. | |
| 2001/0002122 | A1 | 5/2001 | Vong et al. | |
| 2002/0161644 | A1 | 10/2002 | Duffield | |
| 2004/0059790 | A1 * | 3/2004 | Austin-Lane et al. | 709/207 |
| 2004/0127198 | A1 | 7/2004 | Roskind et al. | |
| 2004/0152957 | A1 * | 8/2004 | Stivoric et al. | 600/300 |
| 2005/0245793 | A1 * | 11/2005 | Hilton et al. | 600/300 |
| 2005/0250551 | A1 | 11/2005 | Helle | |
| 2006/0020177 | A1 | 1/2006 | Seo et al. | |
| 2006/0036642 | A1 | 2/2006 | Horvitz et al. | |
| 2006/0090139 | A1 * | 4/2006 | Jenni et al. | 715/760 |
| 2006/0242590 | A1 * | 10/2006 | Polivy et al. | 715/760 |
| 2006/0259537 | A1 | 11/2006 | Emberton et al. | |
| 2006/0277100 | A1 | 12/2006 | Parham | |
| 2006/0293041 | A1 | 12/2006 | Kim | |
| 2007/0049836 | A1 | 3/2007 | Chen | |
| 2007/0118043 | A1 | 5/2007 | Oliver et al. | |
| 2007/0143068 | A1 | 6/2007 | Pasolini et al. | |
| 2007/0173327 | A1 * | 7/2007 | Kilgore et al. | 463/42 |
| 2007/0188468 | A1 | 8/2007 | Lee et al. | |
| 2007/0219059 | A1 | 9/2007 | Schwartz et al. | |
| 2007/0293371 | A1 | 12/2007 | Hilfiker et al. | |
| 2008/0070603 | A1 | 3/2008 | Mao | |
| 2008/0155455 | A1 * | 6/2008 | Balasubramanian | 715/779 |
| 2008/0157956 | A1 | 7/2008 | Radivojevic et al. | |
| 2008/0191885 | A1 | 8/2008 | Loree, IV et al. | |
| 2008/0200312 | A1 * | 8/2008 | Tagliabue | 482/9 |
| 2008/0249736 | A1 | 10/2008 | Prstojevich | |
| 2008/0269625 | A1 | 10/2008 | Halperin et al. | |
| 2008/0319330 | A1 | 12/2008 | Juntunen et al. | |
| 2009/0043531 | A1 | 2/2009 | Kahn et al. | |
| 2009/0105047 | A1 | 4/2009 | Guidi et al. | |
| 2009/0125917 | A1 | 5/2009 | Parker et al. | |
| 2009/0167542 | A1 | 7/2009 | Culbert et al. | |
| 2009/0221403 | A1 | 9/2009 | Chan et al. | |
| 2009/0305732 | A1 | 12/2009 | Marcellino et al. | |
| 2009/0305744 | A1 | 12/2009 | Ullrich | |
| 2009/0307619 | A1 * | 12/2009 | Gupta et al. | 715/764 |
| 2009/0320047 | A1 | 12/2009 | Khan et al. | |
| 2010/0015584 | A1 | 1/2010 | Singer et al. | |
| 2010/0024531 | A1 | 2/2010 | Senoo | |
| 2010/0076278 | A1 | 3/2010 | van der Zande et al. | |
| 2010/0085841 | A1 * | 4/2010 | Lazaridis et al. | 368/73 |
| 2010/0105525 | A1 | 4/2010 | Thukral et al. | |
| 2010/0159995 | A1 * | 6/2010 | Stallings et al. | 455/566 |
| 2010/0185064 | A1 * | 7/2010 | Bandic et al. | 600/306 |
| 2010/0188328 | A1 * | 7/2010 | Dodge et al. | 345/156 |
| 2010/0210975 | A1 | 8/2010 | Anthony, III et al. | |
| 2010/0331145 | A1 | 12/2010 | Lakovic et al. | |
| 2010/0331147 | A1 | 12/2010 | Mikan et al. | |
| 2011/0010617 | A1 * | 1/2011 | Kim et al. | 715/273 |
| 2011/0032105 | A1 | 2/2011 | Hoffman et al. | |
| 2011/0082007 | A1 | 4/2011 | Birrell et al. | |
| 2011/0092282 | A1 * | 4/2011 | Gary | 463/31 |
| 2011/0152696 | A1 | 6/2011 | Ryan | |
| 2011/0154196 | A1 * | 6/2011 | Icho et al. | 715/702 |
| 2011/0213473 | A1 | 9/2011 | Vitolo et al. | |
| 2011/0252362 | A1 * | 10/2011 | Cho et al. | 715/784 |
| 2011/0267196 | A1 | 11/2011 | Hu et al. | |
| 2012/0010478 | A1 | 1/2012 | Kinnunen et al. | |
| 2012/0041767 | A1 | 2/2012 | Hoffman et al. | |
| 2012/0059664 | A1 | 3/2012 | Georgiev et al. | |
| 2012/0060123 | A1 * | 3/2012 | Smith | 715/833 |
| 2012/0078127 | A1 | 3/2012 | McDonald et al. | |
| 2012/0083715 | A1 * | 4/2012 | Yuen et al. | 600/595 |
| 2012/0084053 | A1 * | 4/2012 | Yuen et al. | 702/160 |
| 2012/0112908 | A1 | 5/2012 | Prykari et al. | |
| 2012/0116550 | A1 * | 5/2012 | Hoffman et al. | 700/91 |
| 2012/0129138 | A1 | 5/2012 | Redmann | |
| 2012/0159218 | A1 | 6/2012 | Vangala et al. | |
| 2012/0246246 | A1 | 9/2012 | Moore | |
| 2012/0252416 | A1 | 10/2012 | Kissinger et al. | |
| 2012/0253485 | A1 | 10/2012 | Weast et al. | |
| 2012/0258433 | A1 | 10/2012 | Hope et al. | |
| 2012/0274508 | A1 * | 11/2012 | Brown et al. | 342/357.25 |
| 2012/0277605 | A1 | 11/2012 | Colborn | |
| 2012/0303319 | A1 | 11/2012 | Kirkeby | |
| 2012/0316896 | A1 * | 12/2012 | Rahman et al. | 705/3 |
| 2013/0007665 | A1 * | 1/2013 | Chaudhri et al. | 715/830 |
| 2013/0013331 | A1 | 1/2013 | Horseman | |
| 2013/0017891 | A1 | 1/2013 | Romero et al. | |
| 2013/0067014 | A1 | 3/2013 | Lau et al. | |
| 2013/0072823 | A1 | 3/2013 | Kahn et al. | |
| 2013/0078958 | A1 | 3/2013 | Kyprianou | |
| 2013/0090881 | A1 | 4/2013 | Janardhanan et al. | |
| 2013/0106603 | A1 | 5/2013 | Weast et al. | |
| 2013/0106684 | A1 * | 5/2013 | Weast et al. | 345/156 |
| 2013/0117381 | A1 | 5/2013 | Garcia et al. | |
| 2013/0119255 | A1 * | 5/2013 | Dickinson et al. | 250/340 |
| 2013/0123959 | A1 | 5/2013 | Kan et al. | |
| 2013/0138734 | A1 | 5/2013 | Crivello et al. | |
| 2013/0157646 | A1 | 6/2013 | Ferren et al. | |
| 2013/0178334 | A1 | 7/2013 | Brammer | |
| 2013/0197681 | A1 | 8/2013 | Alberth, Jr. et al. | |
| 2013/0205306 | A1 | 8/2013 | Kelly | |
| 2013/0234924 | A1 | 9/2013 | Janefalkar et al. | |
| 2013/0237874 | A1 | 9/2013 | Zoicas | |
| 2013/0241718 | A1 | 9/2013 | Wang et al. | |
| 2013/0254525 | A1 | 9/2013 | Johnson et al. | |
| 2013/0290879 | A1 * | 10/2013 | Greisson | 715/764 |
| 2013/0293494 | A1 | 11/2013 | Reshef | |
| 2013/0310896 | A1 | 11/2013 | Mass | |
| 2013/0324368 | A1 | 12/2013 | Aragones et al. | |
| 2014/0066816 | A1 | 3/2014 | McNames et al. | |
| 2014/0070957 | A1 * | 3/2014 | Longinotti-Buitoni et al. | 340/870.01 |
| 2014/0099614 | A1 | 4/2014 | Hu et al. | |
| 2014/0143678 | A1 * | 5/2014 | Mistry et al. | 715/746 |

(56) References Cited

U.S. PATENT DOCUMENTS

| | | | | |
|---|---|---|---|---|
| 2014/0143737 | A1* | 5/2014 | Mistry et al. | 715/854 |
| 2014/0169675 | A1* | 6/2014 | King et al. | 382/182 |
| 2014/0176346 | A1 | 6/2014 | Brumback et al. | |
| 2014/0176422 | A1 | 6/2014 | Brumback et al. | |
| 2014/0180595 | A1 | 6/2014 | Brumback et al. | |

FOREIGN PATENT DOCUMENTS

| | | |
|---|---|---|
| WO | WO 2013/040674 | 3/2013 |
| WO | WO 2013/093011 | 6/2013 |
| WO | WO 2013/169755 | 11/2013 |

OTHER PUBLICATIONS

U.S. Appl. No. 14/029,760, filed Sep. 17, 2013, Park et al.
U.S. Appl. No. 14/050,182, filed Oct. 9, 2013, Brumback et al.
U.S. Appl. No. 14/062,717, filed Oct. 24, 2013, Park et al.
U.S. Appl. No. 14/261,344, filed Apr. 24, 2014, Brumback et al.
U.S. Appl. No. 14/261,347, filed Apr. 24, 2014, Brumback et al.
U.S. Appl. No. 14/261,349, filed Apr. 24, 2014, Brumback et al.
US Office Action, dated Feb. 5, 2014, issued in U.S. Appl. No. 14/045,563.
US Office Action, dated Apr. 4, 2014, issued in U.S. Appl. No. 14/045,574.
US Office Action, dated Jan. 8, 2014, issued in U.S. Appl. No. 14/045,592.
US Notice of Allowance, dated Apr. 25, 2014, issued in U.S. Appl. No. 14/045,592.
US Office Action, dated Mar. 27, 2014, issued in U.S. Appl. No. 14/062,717.
US Notice of Allowance, dated Jul. 8, 2014, issued in U.S. Appl. No. 14/062,717.
US Office Action, dated Dec. 30, 2013, issued in U.S. Appl. No. 14/029,760.
US Final Office Action, dated Apr. 8, 2014, issued in U.S. Appl. No. 14/029,760.
US Office Action, dated Dec. 24, 2013, issued in U.S. Appl. No. 14/050,166.
US Applicant-Initiated Interview Summary dated Mar. 11, 2014, issued in U.S. Appl. No. 14/050,166.
US Notice of Allowance, dated Apr. 8, 2014, issued in U.S. Appl. No. 14/050,166.
US Office Action dated Jan. 14, 2014, issued in U.S. Appl. No. 14/050,182.
US Applicant-Initiated Interview Summary dated Mar. 7, 2014, issued in U.S. Appl. No. 14/050,182.
US Final Office Action dated May 1, 2014, issued in U.S. Appl. No. 14/050,182.
US Office Action, dated Jun. 20, 2014, issued in U.S. Appl. No. 14/261,347.
US Office Action, dated Jun. 24, 2014, issued in U.S. Appl. No. 14/261,349.
"Activator is One of the Best Cydia iPhone Hacks | Control your iPhone with Gestures," iphone-tips-and-advice.com, [retrieved on Jul. 9, 2013 at http://www.iphone-tips-and-advice.com/activatior. html], 10 pp.
Ali-Hasan, N., Gavales, D., Peterson, A. & Raw, M., (Apr. 22-27, 2006) "Fitster: Social Fitness Information Visualizer," in Ext. Abstr. Hum. Factors Comput. Syst., ACM Press, 1795-1800.
Anderson, Ian et al. (Aug. 3, 2007) "Shakra: Tracking and Sharing Daily Activity Levels with Unaugmented Mobile Phones," Mobile Networks Appl. 12:185-199.
Bonato, P. (May/Jun. 2010) "Wearable Sensors and Systems," IEEE Eng. in Medicine and Biology Magazine, 29:25-36.
Buttussi, F. & Chittaro, L. (2008) "MOPET, A context-aware and user-adaptive wearable system for fitness training," Artificial Intelligence in Medicine, 42:153-163.
Chudnow, Alan (Dec. 3, 2012) "Basis Wristband Make Its Debut," The Wired Self, Living in a Wired World, published in Health [retrieved on Jul. 22, 2013 at http://thewiredself.com/health/basis-wrist-band-make-its-debut/], 3pp.

DesMarais, Christina (posted on Sep. 3, 2013) "Which New Activity Tracker is Best for You?" Health and Home, Health & Fitness , Guides & Reviews, [Retrieved on Sep. 23, 2013 at http://www.techlicious.com/guide/which-new-activity-tracker-is-right-for-you/] 4 pp.
Dobkin, B. H. & Dorsch, A. (2011) "The Promise of mHealth: Daily Activity Monitoring and Outcome Assessments by Wearable Sensors," Neurorehabilitation and Neural Repair, 25(9):788-98.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 10 Owner's Manual (Aug. 2012), Garmin Ltd., 10 pp.
Forerunner® 110 Owner's Manual, (2010) "GPS-Enabled Sport Watch," Garmin Ltd., 16 pp.
Forerunner® 201 personal trainer owner's manual, (Feb. 2006) Garmin Ltd., 48 pp.
Forerunner® 205/305 Owner's Manual, GPS-enabled trainer for runners, (2006-2008), Garmin Ltd., 80 pp.
Forerunner® 210 Owner's Manual, (2010) "GPS-Enabled Sport Watch," Garmin Ltd., 28 pp.
Forerunner® 301 personal trainer owner's manual, (Feb. 2006) Garmin Ltd., 66 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 405CX Owner's Manual, "GPS-Enabled Sports Watch With Wireless Sync," (Mar. 2009), Garmin Ltd., 56 pp.
Forerunner® 410 Owner's Manual, (Jul. 2012) "GPS-Enabled Sport Watch With Wireless Sync," Garmin Ltd., 52 pp.
Forerunner® 50 with ANT+Sport™ wireless technology, Owner's Manual, (Nov. 2007) Garmin Ltd., 44 pp.
Forerunner® 910XT Owner's Manual, (Jan. 2013) Garmin Ltd., 56 pp.
Gamelin, F.X., Berthoin, S. & Bosquet, L. (2006) "Validity of the Polar S810 Heart Rate Monitor to Measure R-R Intervals at Rest," Med. Sci. Sports Exerc. 38(5):887-893.
Garmin Swim™ Owner's Manual (Jun. 2012), 12 pp.
Gomes, N. et al. (2012) "Steptacular: An incentive mechanism for promoting wellness," in Conf. Commun. Syst. Networks, IEEE, 1-6.
Gupta, N. & Jilla, S. (2011) "Digital Fitness Connector: Smart Wearable System," First International Conference on Informatics and Computational Intelligence, IEEE Computer Society, 118-121.
Kranz, M. et al. (2013) "The mobile fitness coach: Towards individualized skill assessment using personalized mobile devices," Pervasive Mob. Computing, 9:203-215.
Lane, N. et al. (2010) "A survey of mobile phone sensing," IEEE Communications Magazine, 48:140-150.
Lark/Larkpro, User Manual, (2012) "What's in the box," Lark Technologies, 7 pp.
Larklife, User Manual, (2012) Lark Technologies, 7 pp.
Le Masurier, G. C. & Tudor-Locke, C. (2003) "Comparison of Pedometer and Accelerometer Accuracy under Controlled Conditions," Med.& Sci. in Sports & Exerc. 35:867-871.
Marschollek, M. et al. (Aug. 20-24, 2008) "A performance comparison of accelerometry-based step detection algorithms on a large, non-laboratory sample of healthy and mobility-impaired persons," 30th Annual International IEEE EMBS Conference, Vancouver, BC, Canada, Eng. Med. Biol. Mag. 1319-1322.
Milošević, M., Shrove, M. T. & Jovanov, E. (Jun. 2011) "Applications of Smartphones for Ubiquitous Health Monitoring and Wellbeing Management," Journal of Information Technology and Applications, 1:7-15.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
"Parts of Your Band," (Product Release Date Unknown, downloaded Jul. 22, 2013) Jawbone UP Band, 1 page.

(56) References Cited

OTHER PUBLICATIONS

Polar WearLink® + Coded Transmitter 31 Coded Transmitter W.I.N. D. User Manual, Polar® Listen to Your Body, *Manufactured by Polar Electro Oy*, (2010) 11 pages.

Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.

Schloesser, M., Schnitzer, A., Ying, H., Silex, C. & Schiek, M. (Aug. 20-24, 2008) "iSANLA: intelligent Sensor and Actuator Network for Life science Applications," *i 30th Annual International IEEE EMBS Conference*, Vancouver, BC, Canada, *Med. Biol. Soc.* 2369-2372.

Schneider, P.L., Crouter, S. E. & Bassett, D. R. (2004) "Pedometer Measures of Free-Living Physical Activity: Comparison of 13 Models," *Med.& Sci. in Sports & Exerc.* 36(2):331-335.

Tudor-Locke, C., Ainsworth, B.E., Thompson, R.W. & Matthews, C.E. (2002) Comparison of pedometer and accelerometer measures of free-living physical activity, *Med. Sci. Sports Exerc.* 34(12):2045-2051.

Tudor-Locke, C. et al. (Mar.-Apr. 2006) "Evaluation of Quality of Commercial Pedometers," *Can. J. Public Heal.* 97(1):S10-S15.

Ying, H., Silex, C., Schnitzer, A., Leonhardt, S. & Schiek, M. (Springer Berlin Heidelberg, 2007) "Automatic Step Detection in the Accelerometer Signal," *in Wearable Implant Body Sens. Networks* (Leonhardt, S., Falck, T. & Mahonen, P.) 13:80-85.

Zichermann, G. & Cunningham, C. (2011) "Gamification by Design, Implementing Game Mechanics in Web and Mobile Apps," *O'Reilly Media*, Excerpt of pp. 55-58.

US Final Office Action, dated Jul. 28, 2014, issued in U.S. Appl. No. 14/045,563.

US Office Action, dated Feb. 12, 2015, issued in U.S. Appl. No. 14/029,763.

\* cited by examiner

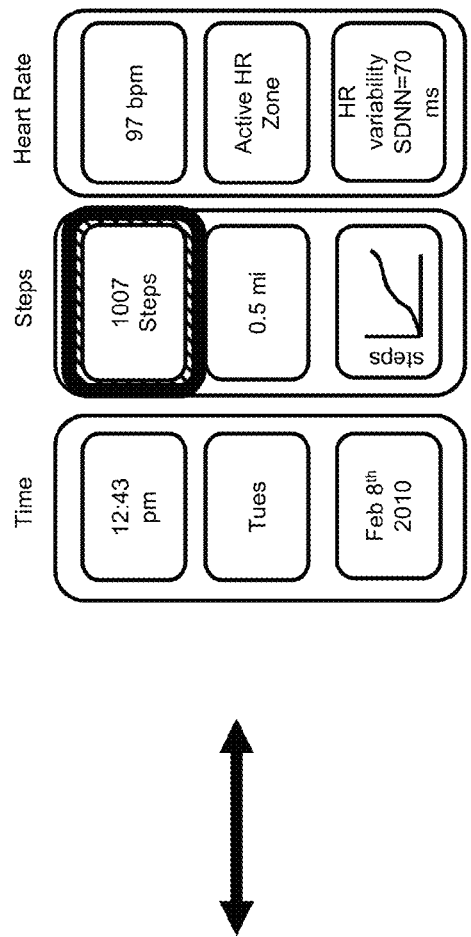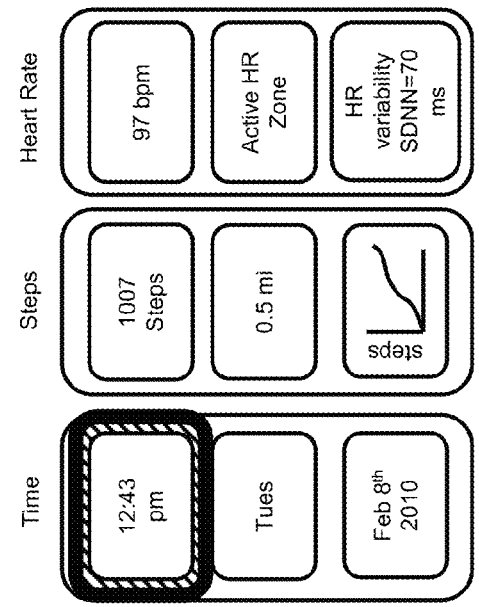
Figure 11

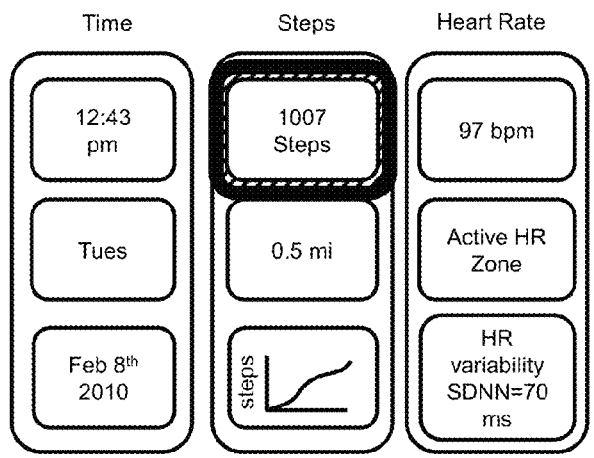
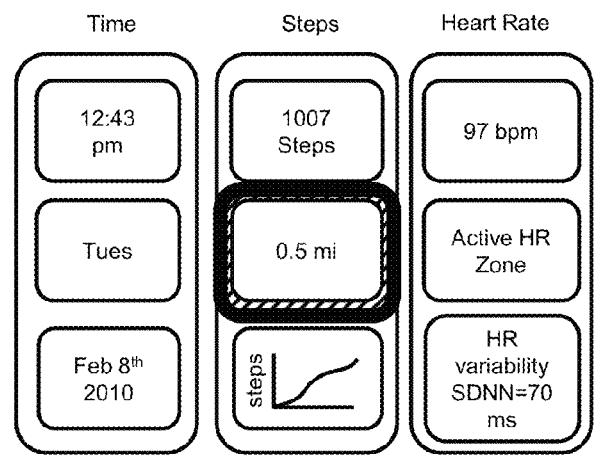
Figure 12

| Display Status | Sequential Display Order |
|---|---|
|  | Clock Data Display Page |
|  | Steps Taken Data Display Page |
| Currently Displayed | Distance Traveled Data Display Page |
| Next | Calories Burned Data Display Page |
|  | Stair Flights Climbed Data Display Page |

Figure 22A

| Display Status | Sequential Display Order |
|---|---|
|  | Clock Data Display Page |
|  | Steps Taken Data Display Page |
| Last Displayed | Distance Traveled Data Display Page |
| Next | [Interim] Clock Data Display Page |
|  | [Interim] Distance Traveled Data Display Page |
|  | Calories Burned Data Display Page |
|  | Stair Flights Climbed Data Display Page |

Figure 22B

BIOMETRIC MONITORING DEVICE WITH CONTEXTUALLY- OR ENVIRONMENTALLY-DEPENDENT DISPLAY

CROSS REFERENCE TO RELATED APPLICATIONS

This application claims priority benefit as a continuation under 35 U.S.C. §120 to U.S. patent application Ser. No. 14/029,763, filed Sep. 17, 2013, titled "DEVICE STATE DEPENDENT USER INTERFACE MANAGEMENT," and also claims priority benefit under 35 U.S.C. §119(e) to U.S. Provisional Application No. 61/746,101, filed Dec. 26, 2012, titled "CONTEXT DEPENDENT USER INTERFACE," and to U.S. Provisional Patent Application No. 61/789,305, filed Mar. 15, 2013, titled "DEVICE STATE DEPENDENT USER INTERFACE MANAGEMENT," all of which are hereby incorporated by reference in their entireties.

BACKGROUND

Recent consumer interest in personal health has led to a variety of personal health monitoring devices being offered on the market. Such devices, until recently, tended to be complicated to use and were typically designed for use with one activity, e.g., bicycle trip computers.

Recent advances in sensor, electronics, and power source miniaturization have allowed the size of personal health monitoring devices, also referred to herein as "biometric tracking" or "biometric monitoring" devices, to be offered in extremely small sizes that were previously impractical. For example, the Fitbit Ultra is a biometric monitoring device that is approximately 2" long, 0.75" wide, and 0.5" deep; it has a pixelated display, battery, sensors, wireless communications capability, power source, and interface button, as well as an integrated clip for attaching the device to a pocket or other portion of clothing, packaged within this small volume.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, an apparatus is provided. The apparatus may include a wristband configured to be worn on a person's forearm, one or more biometric sensors, a display, at least one processor, and a memory. The memory, the at least one processor, the one or more biometric sensors, and the display may be communicatively connected with one another and the memory may store computer-executable instructions for controlling the at least one processor to a) receive biometric data from the one or more biometric sensors, b) determine that the biometric data indicates that the apparatus has experienced movement consistent with movements of a person's forearm taken to bring a watch worn on the person's forearm into a position allowing the time on the watch to be read by the person, and c) cause, responsive to (b), the display to display a predetermined data display page indicating a measurement obtained or derived from the biometric data or an internal clock of the at least one processor.

In some implementations, the measurement may be the time of day, stair flights climbed, stairs climbed, steps taken, distance traveled in miles or kilometers, or calories burned.

In some implementations, the memory may further store computer-executable instructions for controlling the at least one processor to cause the display to turn on from an off state responsive to (b).

In some implementations, the apparatus may also include a backlight and the memory may further store computer-executable instructions for controlling the at least one processor to cause the backlight to turn on from an off state responsive to (b).

In some implementations, the measurement may be the time of day.

In some implementations, the biometric data may indicate that the apparatus has experienced movement corresponding with motion experienced by the distal end of the person's forearm with flexure of the forearm about the forearm's elbow joint.

In some implementations, the biometric data may indicate that the apparatus has experienced movement corresponding with motion experienced by the distal end of the person's forearm through movement of the person's forearm from a position substantially aligned with the sagittal and frontal planes of the person to a position substantially aligned with the transverse and frontal planes of the person.

In some implementations, the biometric data may indicate that the apparatus has experienced movement corresponding with motion experienced by the distal end of the person's forearm through adduction of the person's wrist joint with respect to the mid-sagittal plane of the person and medial rotation of the hand connected to the wrist joint.

In some implementations, the biometric data may indicate that the apparatus has experienced movement corresponding with motion of the distal end of the person's forearm due to rotational motion of the person's wrist joint.

In some implementations, the biometric data may indicate that the apparatus has experienced movement corresponding with motion of the distal end of the person's forearm due to rotational motion of the person's forearm.

In some implementations, an apparatus may be provided. The apparatus may include a wristband configured to be worn on a person's forearm, the wristband having a wrist axis that is substantially aligned with the person's forearm when the wristband is worn on the person's forearm. The apparatus may also include one or more biometric sensors, a display, at least one processor, and a memory. The memory, the at least one processor, the one or more biometric sensors, and the display may be communicatively connected with one another and the memory may store computer-executable instructions for controlling the at least one processor to a) receive biometric data from the one or more biometric sensors, b) determine that the biometric data indicates that the apparatus has experienced rotation about at least one axis, and c) cause, responsive to (b), the display to display a data display page including a time-of-day clock.

In some implementations, the memory may further store computer-executable instructions for controlling the at least one processor to cause the display to turn on from an off state responsive to (b).

In some implementations, the memory may further store computer-executable instructions for controlling the at least one processor to determine that the biometric data indicates that the apparatus has experienced rotation about the at least one axis when the biometric data indicates that the apparatus has experienced rotation about the wrist axis.

In some implementations, the memory may further store computer-executable instructions for controlling the at least one processor to determine that the biometric data indicates that the apparatus has experienced rotation about at least one axis when the biometric data indicates that the apparatus has experienced rotation about the wrist axis and at least one additional axis.

In some implementations, the memory may further store computer-executable instructions for controlling the at least one processor to determine that the biometric data indicates that the apparatus has experienced rotation about the at least one axis when the biometric data indicates that the apparatus has experienced rotation about the wrist axis within a predetermined range of rotational rates through a substantially continuous predetermined range of angular displacement.

In some such implementations, the predetermined range of rotational rates may include at least one rotational rate selected from the group consisting of: at least 90° per second, at least 60° per second, at least 45° per second, and at least 30° per second and the range of angular displacement includes at least one angular displacement selected from the group consisting of: at least 90°, at least 60°, at least 45°, and at least 30°.

In some implementations, the one or more biometric sensors may include at least one sensor such as a single-axis or multi-axis gyroscope, a single-axis or multi-axis accelerometer, a magnetometer, an electromagnetic field sensor, a laser rangefinder sensor, a Doppler radar sensor, or an altimeter sensor and the biometric data indicating that the apparatus has experienced rotation about at least one axis may be obtained at least in part from the at least one sensor.

In some implementations, the one or more biometric sensors may include a single-axis or multi-axis gyroscope and the biometric data may indicate that the apparatus has experienced rotation about at least one axis is obtained at least in part from the single-axis or multi-axis gyroscope.

In some implementations, the one or more biometric sensors may include a single-axis or multi-axis accelerometer and the biometric data indicating that the apparatus has experienced rotation about at least one axis may be obtained at least in part from the single-axis or multi-axis accelerometer.

In some implementations, the memory may store computer-executable instructions for controlling the at least one processor to perform (b) and (c) using biometric data exclusively from the single-axis or multi-axis accelerometer.

In some implementations, the memory may store computer-executable instructions for controlling the at least one processor to perform (b) and (c) using biometric data exclusively from the accelerometer.

In some implementations, the biometric data may indicate that the apparatus has transitioned to an orientation with the display facing in a direction substantially aligned with a direction of planetary gravitational acceleration from an orientation with the display facing in a direction substantially misaligned with the direction of planetary gravitational acceleration.

In some implementations, a method may be provided. The method may include detecting, using one or more biometric sensors connected with a wristband, rotation of the wristband about at least one axis; determining that the rotation of the wristband about the at least one axis meets a first threshold; and causing, responsive to the determining, a display connected with the wristband to be transitioned between a state in which the display does not show a time-of-day to a state in which the display shows a time-of-day.

In some implementations, an apparatus may be provided. The apparatus may include one or more biometric sensors, a display, at least one processor, and a memory. The memory, the at least one processor, the one or more biometric sensors, and the display may be communicatively connected with one another and the memory may store computer-executable instructions for controlling the at least one processor to: determine a sequential display order for a plurality of data display pages; receive one or more page advance requests; cause, for each received page advance request, the display to advance to the data display page that is next in the sequential display order with respect to the data display page that is displayed on the display prior to the advance; receive biometric data from the one or more biometric sensors; determine that the biometric data indicates, at least in part, a first contextual or environmental state; and modify the sequential display order of the data display pages based on the determination that the biometric data indicates the first contextual or environmental state to produce a first sequential display order.

In some implementations of the apparatus, when the data display page that is displayed on the display prior to the advance is the last data display page in the sequential display order, the data display page that is first in the sequential display order may be treated as the data display page that is next in the sequential display order.

In some implementations of the apparatus, the sequential display order may reverse after the data display page that is displayed on the display prior to the advance is the last data display page in the sequential display order.

In some implementations of the apparatus, the memory may further store computer-executable instructions for controlling the at least one processor to modify the sequential display order of the data display pages based on the determination that the biometric data indicates the first contextual or environmental state in conjunction with a determination that a mode of the apparatus is active to produce the first sequential display order.

In some implementations of the apparatus, the first contextual or environmental state may be associated with activities selected from the group consisting of walking, running, stair climbing, bicycling, swimming, resting, working, being at home, being in transit in a car or other powered vehicle, driving, and being in a meeting.

In some implementations of the apparatus, the page advance requests may be generated responsive to data collected from the one or more biometric sensors.

In some implementations of the apparatus, the apparatus may further include a page advance input separate from the one or more biometric sensors and the memory, the at least one processor, the one or more biometric sensors, the page advance input, and the display may be communicatively connected with one another. The memory and/or at least one processor may also be configured to receive the one or more page advance requests responsive to corresponding one or more activations of the page advance input. In some such implementations, the page advance input may be a button.

In some further such implementations, the apparatus may be free of buttons except for the page advance input and the one or more biometric sensors and the page advance input may be the only mechanisms in the apparatus that are capable of detecting tactile or audio input to the apparatus.

In some implementations of the apparatus, the memory may further store computer-executable instructions for controlling the at least one processor to determine that the biometric data indicates, at least in part, a second contextual or environmental state different from the first contextual or environmental state, and to modify the sequential display order of the data display pages based on the determination that the biometric data indicates the second contextual or environmental state to produce a second sequential display order, wherein the first sequential display order and the second sequential display order are different.

In some implementations of the apparatus, the memory may further store computer-executable instructions for controlling the at least one processor to modify the sequential display order of the data display pages by adding or removing a data display page from the plurality of data display pages based on the determination that the biometric data indicates the first contextual or environmental state.

In some implementations of the apparatus, the memory may further store computer-executable instructions for controlling the at least one processor to: determine that the first contextual or environmental state is associated with a first user-specified sequential display order and to modify the sequential display order of the data display pages to correspond to the first user-specified sequential display order to produce the first sequential display order.

In some such implementations of the apparatus, the apparatus may also include a communications interface and the memory, the at least one processor, the one or more biometric sensors, the page advance input, the display, and the communications interface may be communicatively connected with one another. The memory and/or at least one processor may be configured to receive data indicating the user-specific sequential display order via the communications interface and from a device external to the apparatus.

In some implementations of the apparatus, the memory may further store computer-executable instructions for controlling the at least one processor to determine that at least one of the data display pages in the plurality of data display pages has a user-specified priority and modify the sequential display order of the data display pages based on the determination that the biometric data indicates the first contextual or environmental state and the user-specified priority of the at least one data display page to produce a first sequential display order.

In some implementations of the apparatus, the memory may further store computer-executable instructions for controlling the at least one processor to determine that the display is turned off when a page advance request is received, determine the data display page displayed on the display when the display was turned off, cause the display to turn on responsive to the page advance request, and modify the sequential display order such that the data display page that was displayed on the display when the display was turned off is displayed on the display after the display is turned on again and responsive to the page advance request.

In some implementations of the apparatus, the memory may further store computer-executable instructions for controlling the at least one processor to determine that the display is turned off when a page advance request is received, determine the data display page displayed on the display when the display was turned off, cause the display to turn on again, modify the sequential display order such that at least one interim data display page different from the data display page that was displayed on the display when the display was turned off is the first data display page or pages displayed on the display after the display is turned on again and responsive to the page advance request, and modify the sequential display order such that the data display page that was displayed on the display when the display was turned off is the next data display page that is displayed on the display after the at least one interim data display page is displayed.

In some such implementations of the apparatus, the at least one interim data display page may include a data display page showing a time-of-day clock.

In some such implementations of the apparatus, the at least one interim data display page may include a data display page such as a data display page showing a low battery indicator, a data display page showing a low memory indicator, or a data display page showing a sync-in-progress indicator.

In some such implementations of the apparatus, the at least one interim data display page may include a data display page showing user achievement indicator that indicates that one or more quantities based on data provided by the one or more biometric sensors have exceeded a pre-defined threshold, the user achievement indicator in addition to displaying the one or more quantities.

In some such implementations of the apparatus, the apparatus may further include a communications interface configured to communicate with a device external to the apparatus and the memory, the at least one processor, the one or more biometric sensors, the display, and the communications interface may be communicatively connected with one another and the memory may further store computer-executable instructions for controlling the at least one processor to receive a message from the device external to the apparatus via the communications interface, and display a data display page on the display indicating at least some content associated with the message as an interim data display page of the at least one interim data page.

In some further such implementations of the apparatus, the message may be a text message, tweet, social networking website comment, or email.

In some further such implementations of the apparatus, the message may include data indicating a user achievement indicator that indicates that one or more quantities based on data provided by another one or more biometric sensors external to the apparatus have exceeded a pre-defined threshold.

In some such implementations of the apparatus, the plurality of data display pages may include a first subset of at least one data display page, and the memory may further store computer-executable instructions for controlling the at least one processor to cause the at least one data display page of the first subset to be displayed on the display after the display is turned on again regardless of whether the data display page that was displayed on the display when the display was turned off is in the first subset.

In some implementations of the apparatus, at least one of the data display pages in the plurality of data display pages may have a plurality of data display subpages, and the memory may further store computer-executable instructions for controlling the at least one processor to determine a sequential subpage display order for the plurality of data display subpages, receive one or more subpage advance requests, cause, for each received subpage advance request received when the data display subpage having the plurality of data display subpages is displayed, the display to advance to the data display subpage that is next in the sequential subpage display order with respect to the data display subpage that is displayed on the display prior to the advance, wherein when the data display subpage that is displayed on the display prior to the advance is the last data display subpage in the sequential subpage display order, the data display subpage that is first in the sequential subpage display order is treated as the data display subpage that is next in the sequential subpage display order, wherein the data display page having the data display subpage that is displayed on the display is represented by the data display subpage that is displayed on the display.

In some such implementations of the apparatus, each data display subpage of the plurality of data display subpages may present data associated with the data page display having the data display subpages in different units, different formats, or a combination thereof.

In some implementation, a method may be provided. The method may include determining, by one or more processors of a biometric tracking device, a sequential display order for a plurality of data display pages; receiving, by the one or more processors, one or more page advance requests; causing, for each received page advance request, a display of the biometric tracking device to advance to the data display page that is next in the sequential display order with respect to the data display page that is displayed on the display prior to the advance; receiving biometric data from one or more biometric sensors in communication with the biometric tracking device; determining, by the one or more processors, that the biometric data indicates, at least in part, a first contextual or environmental state; and modifying, by the one or more processors, the sequential display order of the data display pages to produce a first sequential display order based on the determination that the biometric data indicates the first contextual or environmental state.

In some implementations of the method, when the data display page that is displayed on the display prior to the advance is the last data display page in the sequential display order, the data display page that is first in the sequential display order may be treated as the data display page that is next in the sequential display order.

In some such implementations of the method, the sequential display order may reverse when the data display page that is displayed on the display prior to the advance is the last data display page in the sequential display order.

In some such implementations of the method, the modifying of the sequential display order of the data display pages to produce the first sequential display order may be based on the determination that the biometric data indicates the first contextual or environmental state in conjunction with a determination that a mode of the apparatus is active.

In some implementations, an apparatus may be provided that includes a wristband, one or more biometric sensors, a display, at least one processor, and a memory. The memory, the at least one processor, the one or more biometric sensors, and the display may be communicatively connected with one another. The wristband, the one or more biometric sensors, the display, the at least one processor, and the memory may form a biometric monitoring device configured to be worn on a person's forearm. The memory may store computer-executable instructions for controlling the at least one processor to receive biometric data from the one or more biometric sensors, display aspects of the biometric data on the display, determine that the biometric data indicates, at least in part, a first contextual or environmental state, and change the content displayed on the display according to the first contextual or environmental state such that the content includes biometric data that has been predetermined to be pertinent to the first contextual or environmental state.

In some implementations of the apparatus, the first contextual or environmental state may be an ambulatory motion state. In some such implementations, the ambulatory motion state may be a walking state, a running state, a hiking state, an interval training state, or a treadmill state, and the content displayed on the display may include one or more data display pages including data such as step count since the first contextual or environmental state was determined, running pace, miles per hour, kilometers per hour, distance run since the first contextual or environmental state was determined, stairs climbed since the first contextual or environmental state was determined, elevation change since the first contextual or environmental state was determined, current elevation, time elapsed since the first contextual or environmental state was determined, current heart rate, current heart rate zone, calories burned, calories burned since the first contextual or environmental state was determined, or combinations thereof.

In some implementations of the apparatus, the ambulatory motion state may be a running state. In some such implementations, the first contextual or environmental state may be determined based on the biometric data indicating a step rate above a first threshold.

In some implementations of the apparatus, the first contextual or environmental state may be determined based on the biometric data indicating a speed above 4 miles per hour and below 20 miles per hour coupled with the biometric data indicating that the person is engaged in ambulatory motion.

In some implementations of the apparatus, the ambulatory motion state may be a walking state. In some such implementations of the apparatus, the first contextual or environmental state may be determined based on the biometric data indicating a non-zero step rate below a first threshold. In some additional or alternative such implementations, the first contextual or environmental state may be determined based on the biometric data indicating a non-zero speed of less than 4 miles per hour coupled with the biometric data indicating that the person is engaged in ambulatory motion.

In some implementations of the apparatus, the first contextual or environmental state may be a water sports state. In some such implementations, the water sports state may be an indoor swimming state or an outdoor swimming state, and the content displayed on the display includes one or more data display pages including data such as laps since the first contextual or environmental state was determined, current stroke type, stroke count of current stroke type, lap time, swimming efficiency, current heart rate, current heart rate zone, calories burned, calories burned since the first contextual or environmental state was determined, or combinations thereof.

In some implementations of the apparatus, the first contextual or environmental state may be an aerobic exercise machine state. In some such implementations, the aerobic exercise machine state may be an elliptical machine state, a stair climbing machine state, a stationary bicycle state, a spinning machine state, or a rowing machine state, and the content displayed on the display may include one or more data display pages including data such as duration since the first contextual or environmental state was determined, current heart rate, current heart rate zone, calories burned, calories burned since the first contextual or environmental state was determined, or combinations thereof.

In some implementations of the apparatus, the first contextual or environmental state may be an aerobic exercise state. In some such implementations of the apparatus, the aerobic exercise state may be a Zumba™ state, an aerobic dance state, a kick boxing state, or a jump rope state, and the content displayed on the display may include one or more data display pages including data such as duration since the first contextual or environmental state was determined, current heart rate, current heart rate zone, calories burned, calories burned since the first contextual or environmental state was determined, or combinations thereof.

In some implementations of the apparatus, the first contextual or environmental state may be a resistance training state. In some such implementations of the apparatus, the resistance training state may be a bicep curl state, a benchpress state, a military press state, a pull-ups state, a push-ups state, a sit-ups state, or a squats state, and the content displayed on the display may include one or more data display pages including data such as number of repetitions since the first contextual or environmental state was determined, number of sets since the first contextual or environmental state was determined, time between sets, current heart rate, current heart rate zone, calories burned, calories burned since the first contextual or environmental state was determined, lifting form, or combinations thereof.

In some implementations of the apparatus, the first contextual or environmental state may be a rest state. In some such implementations of the apparatus, the rest state may be a sleeping state, a reclining state, a sitting state, an office work state, a reading state, a watching-TV state, or a leisure state, and the content displayed on the display may include one or more data display pages including data such as sleep quality, number of times awoken, sleep stage, duration since the first contextual or environmental state was determined, or combinations thereof.

In some such implementations of the apparatus, the rest state may be a sleep state and the content displayed on the display may include one or more data display pages including data such as quiescent sleep time, restless sleep time, ambulatory sleep time, overall time elapsed since the first contextual or environmental state was determined, or combinations thereof. In some such implementations of the apparatus, the sleep state may be determined based on the biometric data indicating inactivity over a first time period. In some alternative or additional such implementations, the sleep state may be determined based on the biometric data indicating inactivity over a first time period including time between the localized time of 9:00 PM and 6:00 AM.

These and other implementations are described in further detail with reference to the Figures and the detailed description below.

BRIEF DESCRIPTION OF THE DRAWINGS

The various implementations disclosed herein are illustrated by way of example, and not by way of limitation, in the figures of the accompanying drawings, in which like reference numerals may refer to similar elements.

FIG. 11 further depicts the data display pages and associated data display subpages for the example biometric monitoring device of FIG. 10.

FIG. 12 also further depicts the data display pages and associated data display subpages for the example biometric monitoring device of FIG. 10.

FIGS. 22A and 22B provide examples of sequential display orders.

DETAILED DESCRIPTION

Figure 1:
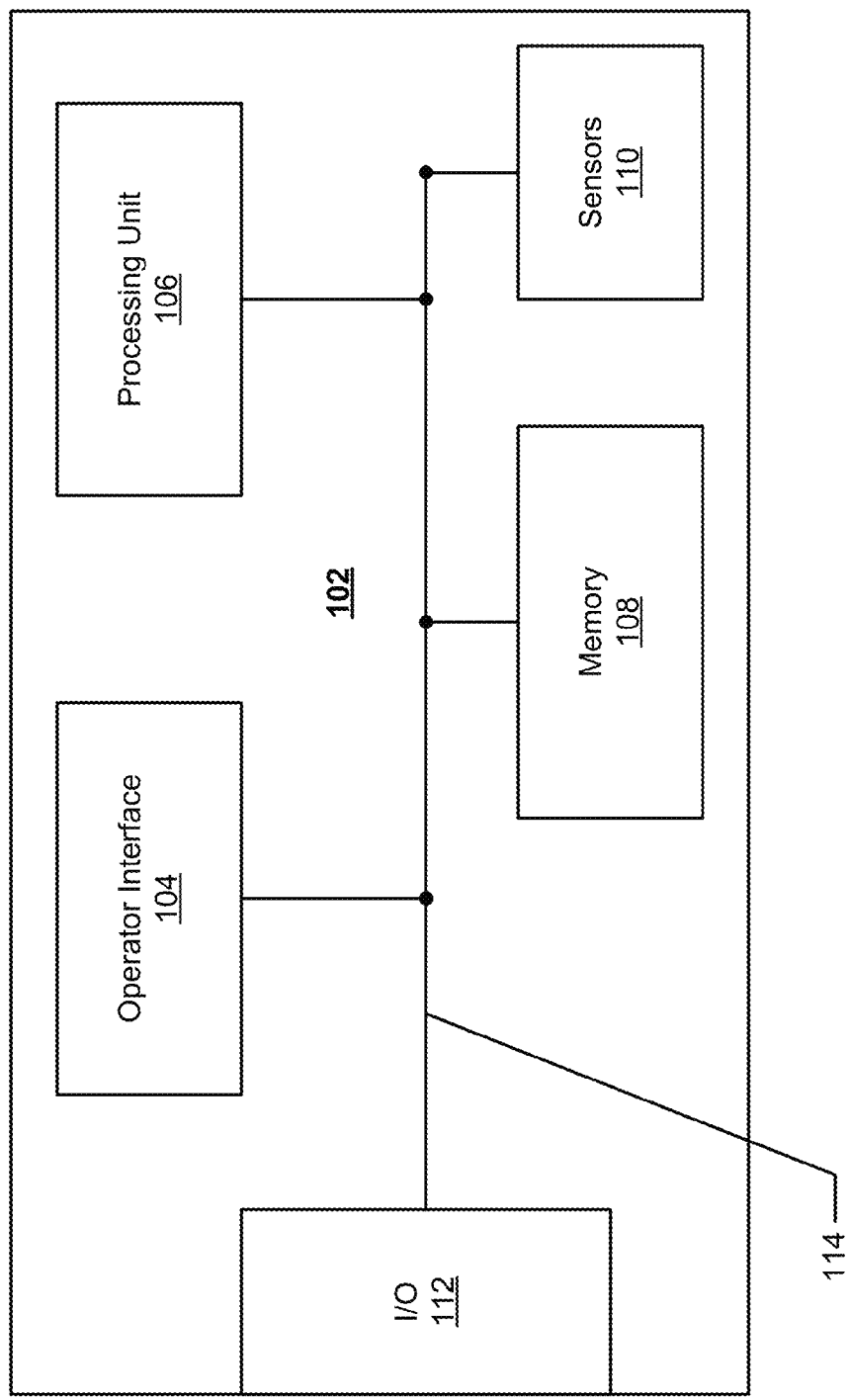
FIG. 1 depicts a generalized schematic of an example computing device that may be used to implement a portable biometric monitoring device or other device with which the various operations described herein may be executed.

The present disclosure relates to wearable biometric monitoring devices (also referred to herein as "biometric tracking devices" or simply as "devices") such as those, for example, illustrated schematically in FIG. 1. In some implementations, a biometric monitoring device may be designed such that it may be inserted into, and removed from, a plurality of compatible cases/housings/holders, e.g., a wristband that may be worn on a person's forearm or a belt clip case that may be attached to a person's clothing. Generally speaking, a biometric monitoring device or biometric tracking device combined with a case or some other means allowing it to be worn or easily carried by a person may be referred to herein as a "biometric monitoring system" or "biometric tracking system."

As used herein, the term "wristband" may refer to a band that is designed to fully or partially encircle a person's forearm near the wrist joint. The band may be continuous, e.g., without any breaks (it may stretch to fit over a person's hand or have an expanding portion similar to a dress watchband), or may be discontinuous, e.g., having a clasp or other connection allowing the band to be closed similar to a watchband or may be simply open, e.g., having a C-shape that clasps the wearer's wrist.

FIG. 1 depicts a generalized schematic of an example portable biometric monitoring device, also simply referred to herein as "biometric monitoring device," or other device with which the various operations described herein may be executed. The portable biometric monitoring device 102 may include a processing unit 106 having one or more processors, a memory 108, an operator interface 104, one or more biometric sensors 110, and input/output 112. The processing unit 106, the memory 108, the operator interface 104, the one or more biometric sensors 110, and the input/output interface 112 may be communicatively connected via communications path(s) 114 (it is to be understood that some of these components may also be connected with one another indirectly).

The portable biometric monitoring device may collect one or more types of biometric data, e.g., data pertaining to physical characteristics of the human body (such as heartbeat, perspiration levels, etc.) and/or data relating to the physical interaction of that body with the environment (such as accelerometer readings, gyroscope readings, etc.), from the one or more biometric sensors 110 and/or external devices (such as an external heart rate monitor, e.g., a chest-strap heart rate monitor) and may then store such information for later use, e.g., for communication to another device via the I/O interface 112, e.g., a smartphone or to a server over a wide-area network such as the Internet. The processing unit 106 may also perform an analysis on the stored data and may initiate various actions depending on the analysis. For example, the processing unit 106 may determine that the data stored in the memory 108 indicates that a goal threshold has been reached and may then display content on a display of the portable biometric monitoring device celebrating the achievement of the goal. The display may be part of the operator interface 104 (as may be a button or other control, not pictured, that may be used to control a functional aspect of the portable biometric monitoring device).

In general, biometric monitoring devices may incorporate one or more types of user interfaces including but not limited to visual, auditory, touch/vibration, or combinations thereof. The biometric monitoring device may, for example, display information relating to one or more of the data types available and/or being tracked by the biometric monitoring device through, for example, a graphical display or through the intensity and/or color of one or more LEDs. The user interface may also be used to display data from other devices or internet sources. The device may also provide haptic feedback through, for instance, the vibration of a motor or a change in texture or shape of the device. In some implementations, the biometric sensors themselves may be used as part of the user interface, e.g., accelerometer sensors may be used to detect when a person taps the housing of the biometric monitoring unit with a finger or other object and may then interpret such data as a user input for the purposes of controlling the biometric monitoring device. For example, double-tapping the housing of the biometric monitoring device may be recognized by the biometric monitoring device as a user input that will cause the display of the biometric monitoring device to turn on from an off state or that will cause the biometric monitoring device to transition between different monitoring states, e.g., from a state where the biometric monitoring device may interpret data according to rules established for an "active" person to a state where the biometric monitoring device may interpret data according to rules established for a "sleeping" person.

In another example, while the user is wearing the biometric monitoring device 102, the biometric monitoring device 102 may calculate and store a user's step count while the user is wearing the biometric monitoring device 102 and then subsequently transmit data representative of step count to the user's account on a web service like www.Fitbit.com, to a mobile computational device, e.g., a phone, paired with the portable biometric monitoring unit, and/or to a standalone computer where the data may be stored, processed, and visualized by the user. Such transmission may be carried out via communications through I/O interface 112. Indeed, the device may measure, calculate, or use a plurality of other physiological metrics in addition to, or in place of, the user's step count. These include, but are not limited to, caloric energy expenditure, floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, and respiration rate. Some of this data may be provided to the biometric monitoring device from an external source, e.g., the user may input their height, weight, and stride in a user profile on a fitness-tracking website and such information may then be communicated to the biometric monitoring device via the I/O interface 112 and used to evaluate, in tandem with data measured by the biometric sensors 110, the distance traveled or calories burned of the user. The device may also measure or calculate metrics related to the environment around the user such as barometric pressure, weather conditions, light exposure, noise exposure, and magnetic field.

As mentioned previously, collected biometric data from the biometric monitoring device may be communicated to external devices through the communications or I/O interface 112. The I/O or communications interface may include wireless communication functionality so that when the biometric monitoring device comes within range of a wireless base station or access point, the stored data automatically uploads to an Internet-viewable source such as a website, e.g., www.Fitbit.com. The wireless communications functionality may be provided using one or more communications technologies known in the art, e.g., Bluetooth, RFID, Near-Field Communications (NFC), Zigbee, Ant, optical data transmission, etc. The biometric monitoring device may also contain wired communication capability, e.g., USB.

Other implementations regarding the use of short range wireless communication are described in U.S. patent application Ser. No. 13/785,904, titled "Near Field Communication System, and Method of Operating Same" filed Mar. 5, 2013 which is hereby incorporated herein by reference in its entirety.

It is to be understood that FIG. 1 illustrates a generalized implementation of a biometric monitoring device 102 that may be used to implement a portable biometric monitoring device or other device in which the various operations described herein may be executed. It is to be understood that in some implementations, the functionality represented in FIG. 1 may be provided in a distributed manner between, for example, an external sensor device and communication device, e.g., a chest-strap heart rate sensor that may communicate with a biometric monitoring device.

Moreover, it is to be understood that in addition to storing program code for execution by the processing unit to effect the various methods and techniques of the implementations described herein, the memory 108 may also store configuration data or other information used during the execution of various programs or instruction sets or used to configure the biometric monitoring device. The memory 108 may also store biometric data collected by the biometric monitoring device. It is to be further understood that the processing unit may be implemented by a general or special purpose processor (or set of processing cores) and thus may execute sequences of programmed instructions to effectuate the various operations associated with sensor device syncing, as well as interaction with a user, system operator or other system components. In some implementations, the processing unit may be an application-specific integrated circuit.

Though not shown, numerous other functional blocks may be provided as part of the biometric monitoring device 102 according to other functions it may be required to perform, e.g., environmental sensing functionality, etc. Other functional blocks may provide wireless telephony operations with respect to a smartphone and/or wireless network access to a mobile computing device, e.g., a smartphone, tablet computer, laptop computer, etc. The functional blocks of the biometric monitoring device 102 are depicted as being coupled by the communication path 114 which may include any number of shared or dedicated buses or signaling links. More generally, however, the functional blocks shown may be interconnected using a variety of different architectures and may be implemented using a variety of different underlying technologies and architectures. With regard to the memory architecture, for example, multiple different classes of storage may be provided within the memory 108 to store different classes of data. For example, the memory 108 may include non-volatile storage media such as fixed or removable magnetic, optical, or semiconductor-based media to store executable code and related data and/or volatile storage media such as static or dynamic RAM to store more transient information and other variable data.

The various methods and techniques disclosed herein may be implemented through execution of one or more a sequences of instructions, e.g., software programs, by the processing unit 106 or by a custom-built hardware ASIC (application-specific integrated circuit) or programmed into a programmable hardware device such as an FPGA (field-programmable gate array), or any combination thereof within or external to the processing unit 106.

Further implementations of portable biometric monitoring devices can be found in U.S. patent application Ser. No. 13/156,304, titled "Portable Biometric Monitoring Devices and Methods of Operating Same" filed Jun. 8, 2011, which is hereby incorporated herein by reference in its entirety.

In some implementations, the biometric monitoring device may include computer-executable instructions for controlling one or more processors of the biometric monitoring device to obtain biometric data from one or more biometric sensors. The instructions may also control the one or more processors to receive a request, e.g., an input from a button or touch interface on the biometric monitoring device, a particular pattern of biometric sensor data (e.g., a double-tap reading), etc., to display an aspect of the obtained biometric data on a display of the biometric monitoring device. The aspect may be a numerical quantity, a graphic, or simply an indicator (a goal progress indicator, for example). In some implementations, the display may be an illuminable display so as to be visible when displaying data but otherwise invisible to a casual observer. The instructions may also cause the one or more processors to cause the display to turn on from an off state in order to display the aspect of the biometric data. The instructions may also cause the display to turn off from an on state after a predefined time period elapses without any user interaction with the biometric monitoring device; this may assist in conserving power.

Due to the small size of many biometric monitoring devices, many biometric monitoring devices may have limited space to accommodate various user interface components. For example, Fitbit makes a variety of extremely compact biometric tracking units that each incorporate a biometric sensor suite, a battery, a display of some sort, a charging interface, and one or more wireless communications interfaces. In some such examples, the biometric tracking units also incorporate a vibramotor and/or a button. These components may be housed, for example, within housings measuring approximately 2" long, 0.75" wide, and 0.5" thick (Fitbit Ultra™); approximately 1.9" in length, 0.75" wide, and 0.375" thick (Fitbit One™); approximately 1.4" long, 1.1" wide, and 0.375" thick (Fitbit Zip™); and approximately 1.3" in length, 0.5" wide, and 0.25" thick (Fitbit Flex™). Of course, housings of other sizes may be used in other implementations of biometric monitoring devices; the above list is merely intended to illustrate the small size of many such biometric monitoring devices.

Despite the small sizes of the above-listed Fitbit devices, each includes a display of some type—the Fitbit Ultra, Fitbit One, and Fitbit Zip, for example, all include small pixelated display screens capable of outputting text, numbers, and graphics. The Fitbit Flex, due to its smaller size, uses discrete light-emitting diode (LED) indicators, e.g., 5 LEDs arranged in a row, to convey information visually. Each of the above-listed Fitbit devices also have an input mechanism that allows a user to affect some aspect of the device's operation. For example, the Fitbit Ultra and Fitbit One each include a discrete pushbutton that allows a user to affect how the device operates. The Fitbit Zip and Fitbit Flex, by contrast, do not have a discrete pushbutton but are instead each configured to detect, using their biometric sensors, when the user taps the housing of the device; such events are construed by the processor or processors of such devices as signaling a user input, i.e., acting as the input mechanism. In some implementations of biometric monitoring devices described herein, the biometric monitoring devices may have only one mechanism, e.g., biometric sensors, for receiving input from a wearer (other than wireless or wired links to other devices). In some other implementations, the biometric monitoring device may include only one mechanism, e.g., a button, other than the biometric sensors in the biometric monitoring device for receiving input from a wearer. In some implementations, the biometric monitoring device may not have any mechanism for receiving physical input from a wearer, but may instead communicate wirelessly with a paired electronic device, e.g., a smartphone, that allows a user to provide input to the biometric monitoring device. Similarly, in some implementations, the biometric monitoring device may not have any display at all, i.e., be unable to display any biometric data directly—biometric data from such biometric monitoring devices may instead be communicated to a paired electronic device, e.g., a smartphone, wirelessly and such biometric data may then be displayed on data display screens shown on the paired electronic device. Such implementations are also considered to be within the scope of this disclosure, i.e., such a paired electronic device may act as a biometric monitoring device configured to communicate with biometric sensors located external to the biometric monitoring device represented by the paired electronic device (such biometric sensors may be located in a separate module worn elsewhere on the wearer's body).

The present disclosure relates to biometric monitoring devices that change what is displayed on the biometric monitoring device display, and, in some cases, how the biometric monitoring device responds to user input, depending on the state of the biometric monitoring device. The state of the biometric monitoring device may be referred to herein as the "device state" or the "activity state." The device state may be partially or wholly determined by environmental or contextual states (also referred to herein as environments and contexts, respectively) and/or states intrinsic, i.e., not based on environmental or contextual states, to the biometric monitoring device itself (referred to herein as modes). The device state or activity state may generally be indicative of an activity in which the wearer of the biometric device is participating, and is to be further understood to be at least partly determined by biometric data collected from the biometric sensors of the biometric monitoring device. For example, a biometric monitoring device may use biometric data from an altimeter to determine that the wearer of the device is gaining altitude consistent with climbing a flight of stairs, and may also determine that the wearer of the device is walking or running—based on such biometric data, the biometric monitoring device may determine (without any deliberate input from the wearer) that the wearer is climbing a flight of stairs. The biometric monitoring device may thus enter a "stair climbing" environmental or contextual state for the duration of such activity.

Generally speaking, modes are typically user-selectable, e.g., they may be deliberately engaged by a user of the biometric monitoring device, either directly, such as by pressing a button on the biometric monitoring device or by sending a command to the biometric monitoring device from a paired smart phone or other external device, or indirectly, such as by configuring the biometric monitoring device to enter into a desired mode based on some user-set condition being met. One example of such a user-defined condition may be observed with respect to a "workday mode" of an example biometric monitoring device that is active on the example biometric monitoring device between the hours of 8 AM and 5 PM, Monday through Friday—the example biometric monitoring device may be reconfigurable to allow a user who worked the night shift to redefine the "workday mode" as being active on the biometric monitoring device between the hours of 8 PM to 4 AM, Monday through Saturday.

Modes may also be triggered independently of any user interaction or biometric data collected from the biometric monitoring device's biometric sensors. For example, some modes may be triggered based on a system state of the biometric monitoring device, e.g., a low battery mode, a low memory mode, a sync mode, etc.

Correspondingly, environments and contexts are generally determined by data analysis performed on the data produced by the biometric sensors and generally correspond to the environment experienced by the wearer of a biometric monitoring device or, more typically, the environment experienced by the biometric monitoring device.

The boundary between environments/contexts and modes may not be clearly delineated in some implementations. For example, in some biometric monitoring devices, biometric data collected from the biometric sensors may be used to determine if a user has performed an act that is intended to be an input or interaction with the biometric monitoring device, e.g., a gesture for controlling the biometric monitoring device or a double-tap of a person's finger on the housing of the biometric monitoring device. In such cases, such biometric data may be interpreted as a deliberate request from the user to enter a particular mode and not, by itself, as deterministic of an environmental state or contextual state. Typically, user inputs are extremely short in duration, e.g., on the order of a few seconds or less, whereas environmental and contextual states are determined with respect to a much longer timeframe, e.g., tens of seconds or even on the order of minutes or tens of minutes. While biometric data that is interpreted as a deliberate request may be contained within a larger dataset of biometric data that triggers an environmental or contextual state, the biometric data that is interpreted as the deliberate request does not, by itself, trigger such an environmental or contextual state). Accordingly, the triggering of an environmental or contextual state is not viewed as being "based on" biometric data that is deterministic of a deliberate request, even if the biometric data that is deterministic of the deliberate request is included in a larger dataset of biometric data that is deterministic of the environmental or contextual state.

In some implementations, an environmental or contextual state may, in addition to being determined based at least in part on biometric data, also be determined based at least in part on a mode that is active on the biometric monitoring device. For example, if a wearer of a biometric monitoring device activates a "bicycling" mode, e.g., via input from a linked smartphone, the biometric monitoring device may interpret biometric data from the perspective of the data likely indicating "bicycling." For example, if the biometric data indicates that the wearer is experiencing high-frequency accelerations, e.g., such as those felt at the handlebars of a bicycle due to road vibrations, the biometric monitoring device may interpret such biometric data as correlating with a "bicycling" environmental state. If such vibrations are not detected in the biometric data, the biometric monitoring device may interpret such biometric data as correlating with a "resting" environmental state (or perhaps a "walking" environmental state). If the wearer has activated a different mode, e.g., a "skiing" mode, then such high-frequency accelerations may be interpreted as indicative of a "downhill skiing" environmental state or context. Thus, the user may, in some implementations, provide some cues to the biometric monitoring device in the form of modes that may influence, at least in part, how the biometric monitoring device determines which environmental state or contextual state is active. Environmental and contextual states may be determined based on a number of different techniques, and the present disclosure may be applied in biometric monitoring devices that utilize presently-known techniques for determining environmental or contextual states, as well as future-developed techniques for determining environmental or contextual states.

For example, biometric data that includes accelerometer data may be analyzed to determine if cyclic accelerations are detected in the vertical direction; such accelerations may be interpreted as indicating that the wearer of a biometric monitoring device is experiencing ambulatory motion, e.g., walking or running. The biometric monitoring device may analyze such data to determine the peak-to-peak frequency of such acceleration cycles; depending on the resulting frequency, such biometric data may be determined to represent walking (low frequency) or running (high frequency). A biometric monitoring device may be configured to perform multiple such analyses on biometric data collected by the biometric monitoring device to arrive at a determination of a particular environmental or contextual state.

For example, a biometric monitoring device may be configured to evaluate both accelerometer data and barometric data to determine if a "stair climbing" environmental or contextual state should be active. For example, barometric data indicating an elevation change may be divided by an average stair flight height, e.g., 10 ft, to determine whether such an elevation change represents the climbing of one or more flights of stairs. However, such altitude changes may also occur due to non-stair-climbing activity, e.g., riding an escalator or elevator. To improve accuracy, an additional level of data analysis may be performed by the biometric monitoring device—the rate of altitude change may be analyzed to determine if the rate exceeds any realistic vertical climb rate for a human being climbing stairs unassisted by mechanical equipment. For example, a modern high-rise elevator may allow a person to ascend 20 floors in about 1 minute, which is far faster than a person could climb unassisted. A biometric monitoring device may thus determine that biometric data indicating such a rapid elevation change is not indicative of a "stair climbing" environmental or contextual state. The biometric monitoring device may further refine its analysis of such biometric data by examining accelerometer data collected during the same interval. Such accelerometer data may reveal whether or not the wearer was ambulatory while the altitude change was occurring. If the altitude change occurs at a reasonable rate and the accelerometer data indicates that the wearer was ambulatory while the altitude change occurred, the biometric monitoring device may determine that such altitude change data is indicative of a "stair climbing" environmental or contextual state.

The techniques and technologies discussed herein may be used on a portable biometric monitoring device to improve the user experience over the current state of the art. However, such techniques and technologies may be equally applicable to any of a variety of electronic devices with which a user interacts to retrieve data, e.g., watches, cell phones, personal music players, tablets, etc.

In one implementation, a portable biometric monitoring device may display different data in response to user input according to the device state of the device. Due to the limited display space of many biometric monitoring devices, the data displayed in association with each device state may be partitioned into a plurality of different data display pages (discussed in more detail below), and a user may "advance" through the data display pages associated with a given device state by providing inputs to the biometric monitoring device.

Such device states may, for example, include the display of information related to, but not limited to, a sleep mode, a workout mode, and a normal operation or default mode. For example, when the portable biometric monitoring device is in normal operation mode, the time may be displayed when the user presses a button on the device to "wake" the display. By contrast, the number of calories burned during a workout may be displayed when the user presses the button to wake the display when the device is in workout mode.

Figure 2:
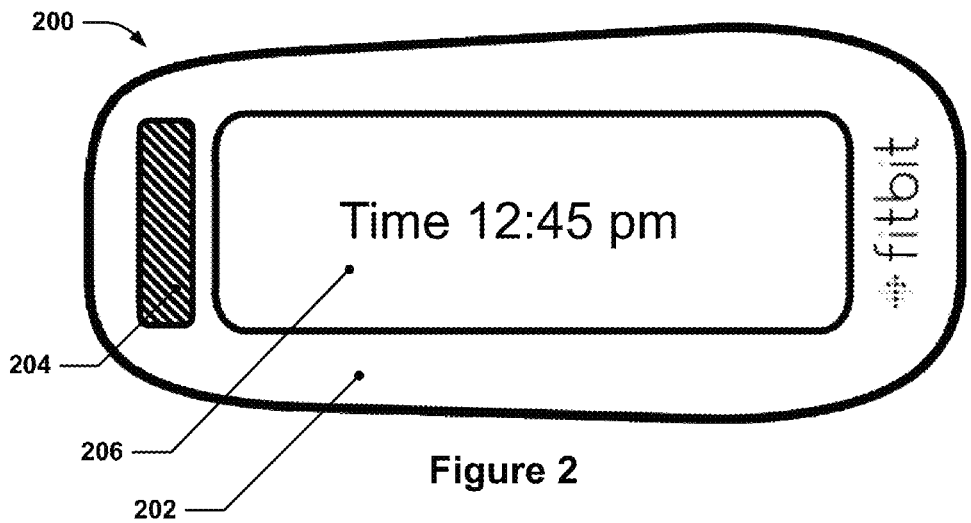
FIG. 2 depicts an example of a biometric monitoring device having a button and a display.
Figure 3:
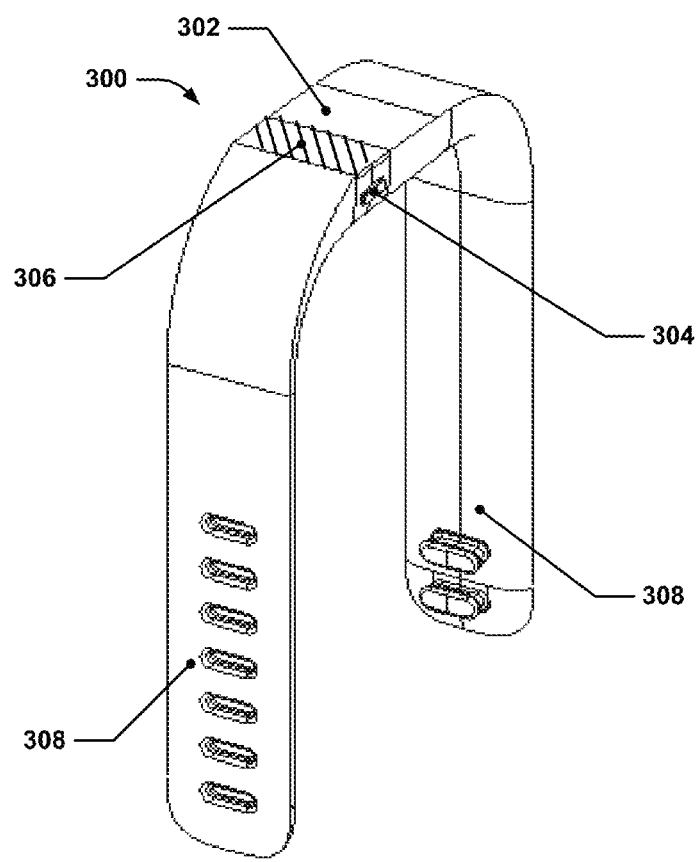
FIG. 3 depicts an example of a wrist-mounted biometric monitoring device having a button, a display, and a band to secure the biometric monitoring device to a user's forearm.
Figure 4:
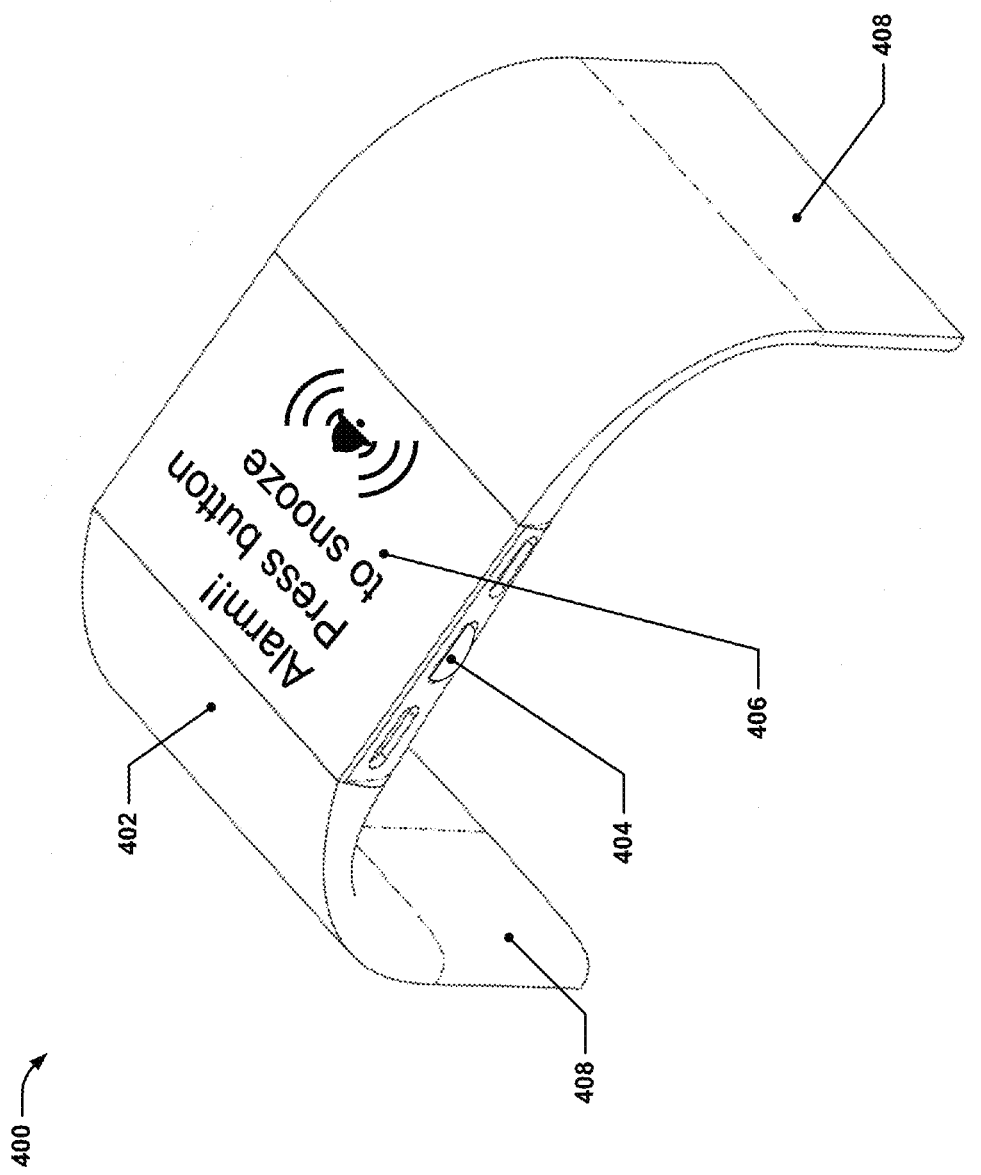
FIG. 4 depicts another example of a wrist-mounted biometric monitoring device having a button, a display, and a band to secure the biometric monitoring device to a user's forearm.

As mentioned above, various implementations of portable biometric monitoring devices described herein may have shapes and sizes adapted for coupling to the body or clothing of a user (e.g., secured to, worn, borne by, etc.). Various examples of such portable biometric monitoring devices are shown in FIGS. 2, 3, and 4. FIG. 2 depicts a biometric monitoring device similar in shape to a Fitbit One, which may be inserted into a holder with a belt clip or into a pocket on a wristband. Biometric monitoring device 200 has a housing 202 that contains the electronics associated with the biometric monitoring device 200. A button 204 and a display 206 may be accessible/visible through the housing 202. FIG. 3 depicts a biometric monitoring device that may be worn on a person's forearm like a wristwatch, much like a Fitbit Flex. Biometric monitoring device 300 has a housing 302 that contains the electronics associated with the biometric monitoring device 300. A button 304 and a display 306 may be accessible/visible through the housing 302. A wristband 308 may be integrated with the housing 302. FIG. 4 depicts another example of a biometric monitoring device that may be worn on a person's forearm like a wristwatch, although with a bigger display than the biometric monitoring device of FIG. 3. Biometric monitoring device 400 has a housing 402 that contains the electronics associated with the biometric monitoring device 400. A button 404 and a display 406 may be accessible/visible through the housing 402. A wristband 408 may be integrated with the housing 402.

As mentioned, the biometric monitoring devices discussed herein may collect one or more types of physiological and/or environmental data from sensors embedded within the biometric monitoring devices, e.g., one or more sensors selected from the group including accelerometers, gyroscopes, altimeters, etc., and/or external devices, e.g., a chest-strap heart rate monitor, and may communicate or relay such information to other devices, including devices capable of serving as an Internet-accessible data sources, thus permitting the collected data to be viewed, for example, using a web browser or network-based application. For example, while the user is wearing a biometric monitoring device, the device may calculate and store the user's step count using one or more sensors. The device may then transmit the data representative of the user's step count to an account on a web service, e.g., www.fitbit.com, a computer, a mobile phone, or a health station where the data may be stored, processed, and visualized by the user. Indeed, the device may measure or calculate a plurality of other physiological metrics in addition to, or in place of, the user's step count.

These physiological metrics may include, but are not limited to, energy expenditure, e.g., calorie burn, floors climbed and/or descended, heart rate, heart rate variability, heart rate recovery, location and/or heading, e.g., via GPS, elevation, ambulatory speed and/or distance traveled, swimming lap count, bicycle distance and/or speed, blood pressure, blood glucose, skin conduction, skin and/or body temperature, electromyography data, electroencephalography data, weight, body fat, caloric intake, nutritional intake from food, medication intake, sleep periods, sleep phases, sleep quality and/or duration, pH levels, hydration levels, and respiration rate. The device may also measure or calculate metrics related to the environment around the user such as barometric pressure, weather conditions, e.g., temperature, humidity, pollen count, air quality, rain/snow conditions, wind speed, light exposure, e.g., ambient light, UV light exposure, time and/or duration spent in darkness, noise exposure, radiation exposure, and magnetic field. Furthermore, the biometric monitoring device, or an external system receiving data from the biometric monitoring device, may calculate metrics derived from the data collected by the biometric monitoring device.

For example, the biometric monitoring device or system may calculate the user's stress levels and/or relaxation levels through a combination of heart rate variability, skin conduction, noise pollution, and sleep quality.

In another example, the device or system may determine the efficacy of a medical intervention, e.g., medication, through the combination of medication intake, sleep and/or activity data. In yet another example, the biometric monitoring device or system may determine the efficacy of an allergy medication through by processing a combination of pollen data, medication intake, sleep and/or activity data. These examples are provided for illustration only and are not intended to be limiting or exhaustive. Further embodiments and implementations of biometric monitoring devices can be found in U.S. patent application Ser. No. 13/156,304, titled "Portable Biometric Monitoring Devices and Methods of Operating Same" filed Jun. 8, 2011 which is hereby incorporated by reference in its entirety.

As mentioned previously, biometric monitoring devices are typically quite small due to practical considerations. People who wish to monitor their performance are unlikely to want to wear a large, bulky device that may interfere with their activities or that may look unsightly. As a result, biometric monitoring devices are often provided in small form factors to allow for light weight and ease of carrying. As mentioned previously, such small form factors often necessitate some design compromises. For example, there may be limited space for displays, controls, and other components of the biometric monitoring device within the device housing. One system component that may be limited in size or performance is the power source, e.g., a battery, capacitor, etc., of the biometric monitoring device. In many implementations, the biometric monitoring device may be in an "always on" state to allow it to continually collect biometric data throughout the day and night. Given that the sensors and processor(s) of the biometric monitoring device must generally remain powered to some degree in order to collect the biometric data, it may be advantageous to implement power-saving features elsewhere in the device, e.g., such as by causing the display to automatically turn off after a period of time.

The Fitbit Ultra™ and the Nike Fuelband™ are both examples of biometric monitoring devices that have data displays that are typically turned off unless the biometric monitoring device is being interacted with by the user in order to save power. A typical user interaction may be provided by pressing a button on the biometric monitoring device, flipping the biometric monitoring device over and back, or double-tapping the housing of the biometric monitoring device.

The term "data display page" is used herein to refer to a visual display including text, graphics, and/or indicators, e.g., LEDs or other lights such as are used on the Fitbit Flex, that are arranged to communicate data measured, produced, or received by a biometric monitoring device to a person viewing a display of the biometric monitoring device. Data that is displayed via data display pages may include biometric sensor data, e.g., accelerometer or altimeter data, or environmental sensor data, e.g., air quality or sunlight. The term "biometric data display page" may be used to refer to data display pages that display such biometric sensor data. Data that is produced by the apparatus may include clock data, timer data, countdown data, achievement badge determinations, etc. Data display pages that display aspects of data that are completely independent of data from the biometric sensors may be referred to herein as "intrinsic data display pages." Examples of intrinsic data display pages are data display pages that display a time-of-day clock, an alarm clock, a stopwatch, and other values that are calculated independently of data received from the biometric sensors. Data display pages that display data received by the apparatus may be referred to herein as "extrinsic data display pages," and may be used to display data that is received from a wireless-linked smartphone, via NFC/wireless with other biometric monitoring devices, or via wireless/NFC or direct communications with a base station. Some data display pages may combine two or more of the above sub-types of data display pages.

In some implementations, a data display page may have several data display sub-pages, any one of which may represent the data display page when used. Such data display sub-pages may present subsets of related data or may present related data that is formatted differently. For example, a data display page of "steps taken" might have "steps," "miles," and "steps v. time" data display subpages, any one of which may be shown as the data display page for "steps taken." Advancing to a different data display subpage of a data display page does not, in itself, cause the data display page itself to advance.

The term "splash page" may be used herein to refer to display pages that are not used to display time-dependent, biometric, or system data, but are instead used to display pre-defined content, e.g., a start-up animation, splash screen, or greeting. A splash page may be randomly selected from a group of possible splash pages (or selected based on a set order) when the display is turned on. While the content of the splash screen may be changed, e.g., by a user entering a custom greeting, it generally does not change responsive to biometric data measured, produced, calculated, or received by the apparatus. Display of a clock is considered to be a "data display page" rather than a "splash page" within this disclosure since clock data is time-dependent. In some cases, a data display page may include content similar to that shown on splash pages, e.g., a person may pre-select a greeting that is displayed in conjunction with the time on a clock data display page; in such instances, such a display is to be understood to be a data display page rather than a splash page.

The order in which data display pages are displayed on a biometric monitoring device display may be referred to herein as a "sequential display order." The sequential display order may change in response to various stimuli, including, but not limited to, user input, past interaction history with the biometric monitoring device, and/or data received from the biometric sensors of the biometric monitoring device. The sequential display order may be modified in two general ways.

In the first case, the relative positioning of two data display pages in the sequence may be changed. For example, data display pages A, B, C, and D may be in the order listed and may then be modified to reflect the sequence A, D, C, and B. Should specific reference to such modification be required, such modifications may be referred to herein as "modifying the order of the sequential display order" or the like.

In the second case of sequential display order modification, various data display pages may be added to or removed from the sequential display order. For example, a biometric monitoring device may have a stopwatch mode that may be enabled by pressing and holding a button of the biometric monitoring device for approximately 2 seconds. When the stopwatch is running, a stopwatch data display page is added to the sequential display order. When the stopwatch is stopped (for example, by again pressing the button for approximately 2+ seconds), its data display page is removed from the sequential display order. It is to be understood that "adding" or "removing" data display pages from the sequential display order may also encompass "hiding" or "showing" such data display pages.

The term "interim data display page" may be used herein to refer to a subtype of data display page. For example, an interim data display page may be a data display page that is either not normally shown as part of the sequential display order, e.g., an achievement celebration screen or text message alert. Interim data display pages may also be data display pages that are in the sequential display order but that may be shown out-of-order, e.g., the sequential display order might be "steps taken; calories burned, clock, and stairs climbed," and the display might display the "clock" data display page when initially turned on, and then proceed to show "steps taken" (followed by "calories burned," "clock" (again), and "stairs climbed" responsive to successive page advance requests). In this example, the "clock" data display page serves as an interim data display page. Another way of thinking of an interim data display page is as a data display page that is associated with a short-lived mode, environmental state, or contextual state, i.e., a mode, environmental state, or contextual state that terminates once its associated data display page or pages, i.e., interim data display page or pages, have been displayed.

In a number of implementations described herein, presentation of data to a user of a biometric monitoring device is improved through device-state-dependent display of information and response to user input. The term "display/response" will be used herein to refer to the display of information and response to user input. It is to be understood that while discussion herein focuses on the visual display of information, information may also or alternatively be communicated through other methods, such as through haptic, e.g., vibratory or Braille display, or audio feedback. The term "display/response" will be used to also describe communication through these alternative methods in addition to visual communication. In general, the techniques described herein with respect to displayed data may also be used with these alternate communications techniques, although visual display may be the most efficient for most situations.

Figure 5:
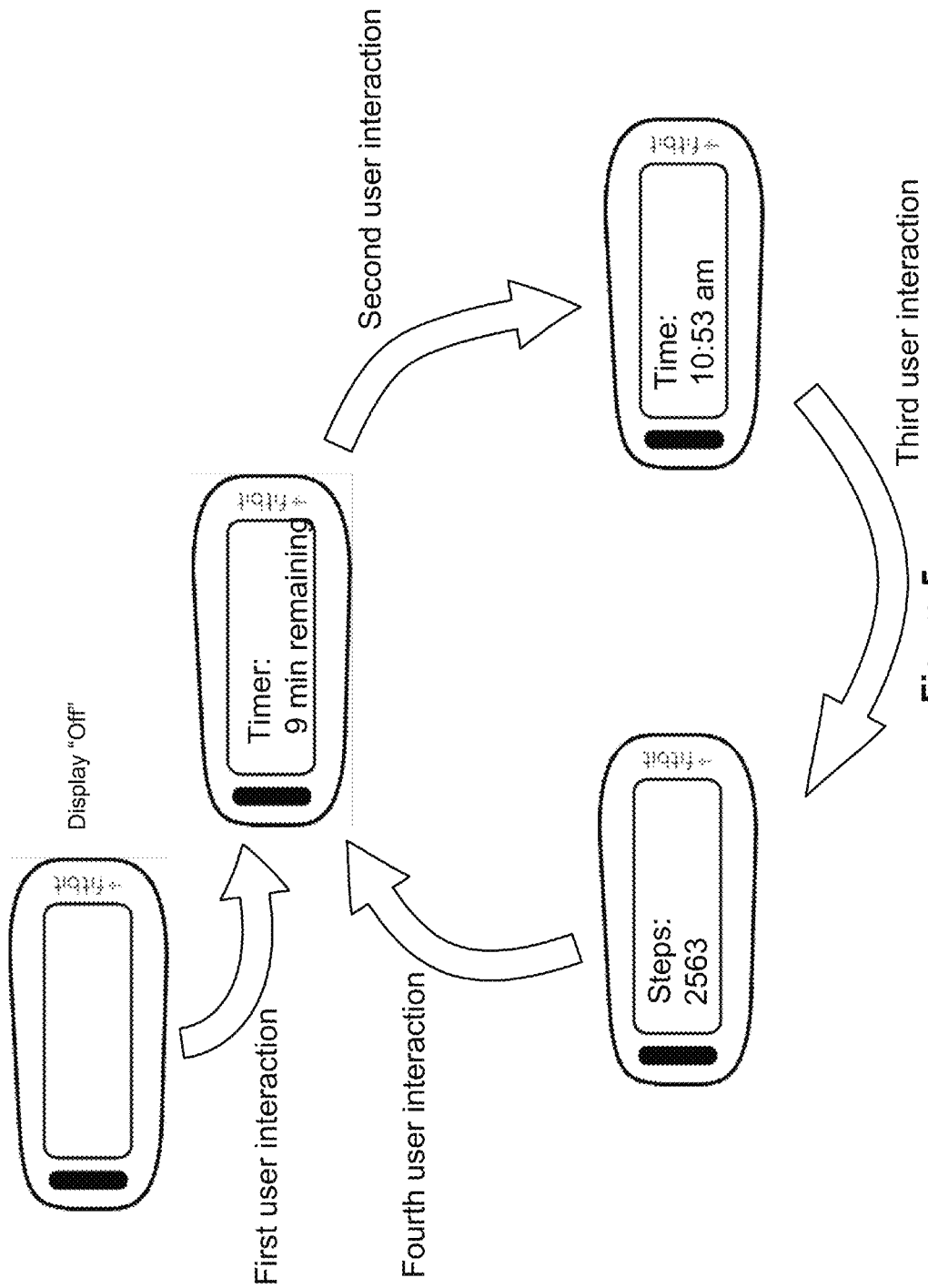
FIG. 5 depicts a diagram showing a sequential display order for a biometric monitoring device that cycles through three separate data display pages.

In one implementation, the device may be a wrist-mounted biometric monitoring device that measures data similar to that measured by the Fitbit Ultra, e.g., metrics such as steps taken, distance traveled, floors climbed, calories burned, activity avatar state, and clock time. Examples of such wrist-mounted biometric monitoring devices are shown in FIGS. 3 and 4. Under normal operation of the biometric monitoring device, an initial user interaction with the biometric monitoring device may cause the display to present the user with the clock time. Each subsequent user interaction, e.g., button press, touching a virtual button on a touch screen, touching a capacitive sensor, performing a gesture on a touch screen, and/or performing a physical gesture, may cause the display to advance through a list of metrics, possibly in a cyclical or iterative fashion as seen in FIG. 5. In another implementation, the biometric monitoring device display may remain on even when the user is not interacting with the device and may automatically revert, for example, to a time-of-day display, i.e., clock time, after a predetermined or programmed interval in which the user has not directly interacted with the biometric monitoring device.

In order to more dynamically change the display/response, a biometric monitoring device may track its device state through a variety of mechanisms and transition through different device states as contextual states, environmental states, and/or modes change. In some implementations, the device may have multiple modes, environmental states, and/or contextual states active simultaneously. In such a case, the device state may be different for each different combination of environmental states, contextual states, and/or modes. Modes may include, but are not limited to, activity annotation, timer, stopwatch, clock/time/watch, sleep monitoring, work, home, and commute, and activity-specific modes for tracking user activities such as biking, swimming, walking, running, climbing, weight-lifting, treadmill exercise, and elliptical machine exercise. Device contexts may be automatically set by the device based on a plurality of signals including but not limited to, step count, calorie burn, floor count, time of day, location (as determined by a GPS, for example), ambient light brightness, and ambient light wavelength. Modes may be set by the user through an interaction with the device including, but not limited to, pressing a button, touching a virtual button on a touch screen, touching a capacitive sensor, performing a gesture on a touch screen, and/or performing a physical gesture. As discussed above, some modes may be triggered based on system conditions within the biometric monitoring device, e.g., low battery mode or low memory mode.

In another implementation, the mode of the biometric monitoring device may be set through a secondary device that may communicate with the biometric monitoring device directly, communicate with the biometric monitoring device via a third party, or communicate with the biometric monitoring device via a variety of external devices and third parties. For example, a user may select the mode of the biometric monitoring device using an application on a smartphone that sends the mode selection to a server. The server, in turn, sends the mode selection to a computer that then sends the mode selection to the device. Alternatively, the smart phone application (or the server) may send the mode selection directly to the device.

In some cases, a mode of the biometric monitoring device may be triggered by an intrinsic condition of the device. In one implementation, a biometric monitoring device may be in a low battery mode when the battery charge within the biometric monitoring device drops below a predefined level. In such a case, the biometric monitoring device may display a low battery warning data display page before any other data display page when the display is first turned on after being in an off state. The low battery mode may coexist with other modes, e.g., the biometric monitoring device may be in a low battery mode as well as another mode simultaneously. For example, the device may be in both a low battery mode and a stopwatch mode. In such a case, the device may show a low battery data display page in response to a first user interaction and a stopwatch data display page in response to a second user interaction.

In one implementation, the device may have a single mode (for example, a wristwatch mode) that may always be active and may thus influence the display/response of any of the device state of the biometric monitoring device. For example, a portable biometric monitoring device physically adapted to be coupled to the body may always have a "wristwatch" mode active that causes the device state to display a data display page showing the current time before displaying other data display pages when the user interacts with the device in one or more specific ways. Preferred interactions may include pressing a button or performing a gesture such as rotating and moving the wrist in a manner similar to motions performed when viewing a wristwatch worn on the forearm. The biometric monitoring device may display the current time data display page regardless of the last data display page that was displayed. The biometric monitoring device may also display the current time data display page first after powering on the display regardless of the environmental state or contextual state indicated by measurements of any of the biometric monitoring device's biometric sensors. The biometric monitoring device may, in some implementations, display the current time data display page regardless of the period of time since the last user interaction and/or last time the display was on.

There are many biometric sensors that may be used to detect various types of biometric data that may determine, at least in part, an environmental state or contextual state that may be active in an activity state or device state. The biometric sensors may include one or more sensors that evaluate a physiological aspect of a wearer of the device, e.g., heart rate sensors, galvanized skin response sensors, skin temperature sensors, electromyography sensors, etc. The biometric sensors may also or alternatively include sensors that measure physical environmental characteristics that reflect how the wearer of the device is interacting with the surrounding environment, e.g., accelerometers, altimeters, GPS devices, gyroscopes, etc. All of these are biometric sensors that may all be used to gain insight into the activities of the wearer, e.g., by tracking movement, acceleration, rotations, orientation, altitude, etc.

A larger listing of potential biometric sensor types and/or biometric data types is shown below in Table 1. This listing is not exclusive, and other types of biometric sensors other than those listed may be used. Moreover, the data that is potentially derivable from the listed biometric sensors may also be derived, either in whole or in part, from other biometric sensors. For example, an evaluation of stairs climbed may involve evaluating altimeter data to determine altitude change, clock data to determine how quickly the altitude changed, and accelerometer data to determine whether biometric monitoring device is being worn by a person who is walking (as opposed to standing still).

TABLE 1

| Biometric Sensor Type | Biometric data potentially measured | Potentially derivable biometric data |
| --- | --- | --- |
| Accelerometers | Accelerations experienced at location worn | Rotation, translation, velocity/speed, distance traveled, steps taken, elevation gained, fall indications, calories burned (in combination with data such as user weight, stride, etc.) |
| Gyroscopes | Angular orientation, angular velocity, angular acceleration and/or rotation | Rotation, orientation |
| Altimeters | Barometric pressure, temperature (to calculate a more accurate altitude) | Altitude change, flights of stairs climbed, local pressure changes, submersion in liquid |
| Pulse Oximeters | Blood oxygen saturation (SpO2), heart rate, blood volume | Heart rate variability, stress levels, active heart rate, resting heart rate, sleeping heart rate, sedentary heart rate, cardiac arrhythmia, cardiac arrest, pulse transit time, heart rate recovery time, blood volume |
| Galvanic Skin Response Sensors | Electrical conductance of skin | Perspiration, stress levels, exertion/arousal levels |
| Global Positioning System (GPS)* | Location, elevation, speed, heading | Distance traveled, velocity/speed |
| Electromyographic Sensors | Electrical pulses | Muscle tension/extension |
| Audio Sensors | Local environmental sound levels | Laugh detection, breathing detection, snoring detection, respiration type (snoring, breathing, labored breathing, gasping), voice detection, typing detection |
| Photo/Light Sensors | Ambient light intensity, ambient light wavelength | Day/night, sleep, UV exposure, TV watching, indoor v. outdoor environment |
| Temperature Sensors | Temperature | Body temperature, ambient environment temperature |
| Strain Gauge Sensors | Weight (the strain gauges may be located in a device remote from the biometric monitoring device, e.g., a Fitbit Aria ™ scale, and communicate weight-related data to the biometric monitoring device, either directly or via a shared account over the Internet) | Body Mass Index (BMI) (in conjunction with user-supplied height and gender information, for example) |
| Bioelectrical Impedance Sensors | Body fat percentage (may be included in remote device, such as Aria ™ scale) | |
| Respiration Rate Sensors | Respiration rate | Sleep apnea detection |
| Blood Pressure Sensors | Systolic blood pressure, diastolic blood pressure | |
| Heart Rate Sensors | Heart rate | |
| Blood Glucose Sensors | Blood glucose levels | |
| Moisture Sensors | Moisture levels | Whether user is swimming, showering, bathing, etc. |

*In some implementations, biometric sensors may specifically exclude GPS sensors and other sensor systems that require a signal from a device not worn on the body of the person wearing the biometric monitoring device. Such implementations may refer to "local biometric sensors" (such biometric monitoring systems may still make use of biometric sensors that are located elsewhere on the wearer's person but that are not physically contained in the biometric monitoring device, e.g., a chest-strap heart rate monitor). It is to be understood that the techniques and systems discussed herein may also utilize biometric data produced solely from local biometric sensors in order to determine, for example, content display, sequential display orders, and environmental or contextual states. Since much biometric data that may be used by biometric monitoring devices to determine environmental or contextual states may be location-independent, i.e., not requiring absolute world location/coordinates, many implementations of biometric monitoring devices as described herein may utilize only local biometric sensors. Of course, other implementations of biometric monitoring systems may utilize biometric sensors that provide absolute world location/coordinates to provide data insights beyond those possible with local biometric sensors.

In addition to the above, some biometric data may be calculated by the biometric monitoring device without direct reference data obtained from the biometric sensors. For example, a person's basal metabolic rate, which is a measure of the "default" caloric expenditure that a person experiences throughout the day while at rest (in other words, simply to provide energy for basic bodily functions such as breathing, circulating blood, etc.), may be calculated based on data entered by the user and the used, in conjunction with data from an internal clock indicating the time of day, to determine how many calories have been expended by a person thus far in the day just to provide energy for basic bodily functions.

A biometric monitoring device mode may also be determined by the presence of or data received from one or a combination of wireless networks or wireless network-connected devices including, but not limited to, active near-field communication (NFC) tags, passive NFC tags, RFID tags, Bluetooth, Wi-Fi devices, and cellular network devices. Devices that use short-range wireless communication are further described in U.S. patent application Ser. No. 13/785,904, titled "Near Field Communication System, and Method of Operating Same," filed Mar. 5, 2013, which is hereby incorporated herein by reference in its entirety. For example, a biometric monitoring device may receive a message from another, nearby biometric monitoring device (via, for example, a wireless link) indicating that the wearer of the other biometric monitoring device has achieved a particular goal; this may cause the biometric monitoring device to enter a "friend goal status" mode that may cause a data display screen indicating that the person associated with the other biometric monitoring device has achieved the goal.

In another implementation, a mode may be determined by the amount of time that has passed since the last user interaction, or the last display of information. For example, a portable biometric monitoring device may be in a "recently on" mode during a predetermined period of time, e.g., a minute, immediately after the display of the biometric monitoring device is turned off, and may be in a "less recently on" mode during a longer predetermined period of time, e.g., 10 minutes, immediately after the display of the biometric monitoring device is turned off. When the "recently on" mode is active, the biometric monitoring device may show the last data display page that was presented prior to powering off the display in response to the user pressing a button to turn on the display. If the "recently on" mode is not active and the "less recently on" mode is active, then the biometric monitoring device may display a "clock" data display page when the user presses a button on the biometric monitoring device. If neither the "recently on" mode nor the "less recently on" mode are active when the user presses a button on the biometric monitoring device to turn on the display, the biometric monitoring device may display a data display page showing the number of steps taken since the display was last on, and then display a data display page showing the time. Specific units of time (minute, ten minutes) are presented above and in other instances herein for purposes of example only and may vary in alternative implementations or programmed configurations.

In another implementation, device state may be determined in part or wholly by data not automatically detected using sensors, but instead by data entered by a person (e.g. by the user). Data entered by a person may include, but is not limited to, user preferences on interaction behavior, gender, visual acuity, age, weight and height. All other data described in this disclosure as being measured by a sensor may also be entered manually by a person into the device or a secondary device, e.g. a laptop, desktop computer and/or smartphone, in communication with the device.

A user may interact with a biometric monitoring device in one or more ways. A typical user input, for example, may include pressing a button. However, as discussed earlier in this disclosure, a user may provide input to biometric monitoring devices through other means. For example, a user may touch a virtual button on a touch screen, touch a capacitive sensor, perform a gesture on a touch screen, or perform a physical gesture, e.g., such as by moving their hand or arm in a specific way. Measurements from one or more sensors selected from the group including, but not limited to, accelerometers, galvanic skin response sensors, thermometers, pressure transducers, altimeters, gyroscopes, photoplethysmograph sensors, electromyographic sensors, force transducers, strain gauges, and magnetometers may be used to detect user input.

The data from such sensors, which may primarily be used to obtain biometric data, may be stored in raw format by the biometric monitoring device or may be pre-processed prior to storage by the biometric monitoring device. For example, the biometric monitoring device may store or buffer the most recent 10 minutes of data in raw form but may then store data from prior to the ten-minute window as filtered data, e.g., with a lower sampling rate and/or with some form of numerical analysis, such as a moving average, performed, or as converted data, e.g., acceleration data may be converted to "steps taken," "stairs climbed," and/or "distance traveled." Data from the biometric sensors, e.g., raw data or post-processed data, may be further analyzed to determine if the biometric data is indicative of a pre-defined biometric state or condition that is associated with a user input. If such analysis indicates that such biometric data has been collected, the biometric monitoring device may then treat such an event as equivalent to a user input.

In some cases, user input may be intrinsic to the state of the user and not consciously controlled by the user, e.g., an autonomic input. For example, a user input may be triggered by reaching a certain heart rate as measured by a photoplethysmographic sensor. The display may show a screen with data related to high heart rate without the user consciously interacting with the biometric monitoring device (other than simply wearing the biometric monitoring device, of course). In another embodiment, a user input may be triggered by reaching or exceeding a certain activity goal for a period of time. For example, meeting a step goal, stair climb goal, distance goal, etc. for the day. In some implementations, an input to the biometric monitoring device may be triggered based on notifications of incoming email, text messages, e.g., via short-message-service (SMS) or via some other mechanism, or comparisons against friends who are competing with the user on specific metrics (e.g., steps).

The biometric monitoring device may be configured to communicate with the user through one or more feedback mechanisms, or combinations thereof, such as vibratory feedback, audio output, graphical output via a display or light-emitting devices, e.g., LEDs. For example, upon detecting or determining that the user has reached a biometric goal, the biometric monitoring device may vibrate to notify the user. If the user then presses a button, the display may turn on and present data about the goal that the user reached, e.g., what goal was reached, if the goal was previously reached one or more times on a different day, week, month, or year, and/or how long it took to reach the goal).

In another example, the color and/or intensity of one or more LEDs may serve as notifications that the user is winning or losing against a friend in a competition in, for example, step count. In yet another example, the biometric monitoring device may be a wrist-mounted device that may vibrate or emit audio feedback to notify the user of an incoming email, text message, or other alert. In some such implementations, if the user then moves his or her wrist in a gesture similar to checking a watch, the display of the biometric monitoring device may be turned on and a data display page relating data relevant to the alert may be presented to the user. In yet another example, the biometric monitoring device may present increasingly noticeable feedback methods based on the importance and/or urgency of the alert. For example, a high priority alert may include audio, vibration, and/or visual feedback, whereas a low priority alert may only include visual feedback. The criteria to distinguish a high priority alert from lower-priority alerts may be defined by the user. For example, a high-priority alert may be triggered if an email message or text is sent with a particular priority, e.g., "urgent," if an email message or text is sent from a particular person, e.g., a person that the user has identified as being high-priority, if a meeting notification or reminder is received or occurs, if a goal is achieved or if some goal milestone is achieved, e.g., a halfway mark of the goal, etc. The preceding examples are provided for illustration and should not be considered as limitations to the present inventions. Indeed, all possible combinations of feedback mechanisms and interactions described herein are intended to be within the scope of the present inventions.

As discussed above, one or more of the biometric sensors discussed herein may be used to detect a physical gesture corresponding to a user input. This allows a user to interact with the device using physical gestures. For example, a wrist-based portable biometric device may contain an accelerometer, magnetometer (which may be used to detect the biometric monitoring device's orientation with respect to the Earth's magnetic field), and/or a gyroscope. One or more of these sensors may be used to determine when the user moves their wrist in a manner that is similar to that performed when viewing a watch. The portable biometric device may interpret this gesture as a user input or interaction. The biometric monitoring device may be configured to display the time on a display of the biometric monitoring device in response to the detection of such a gesture. Other gestures that may be used to cause the portable biometric monitoring device to display a specific data display page such as the time of day include, but are not limited to, multiple taps, or a specific pattern of taps. For example, a user may tap anywhere on the exterior of the portable biometric monitoring device two times within a specific time period, e.g., one second, to cause the display to show a data display page showing the time.

In another embodiment, a wrist-based portable biometric device may have one or more electromyographic (EMG) sensors in the band. These EMG sensors may detect when the user flexes the muscles in their forearm/wrist by forming a fist, for example. This gesture may be interpreted by the portable biometric device as a user input that causes the display to show the time, for example. While some physical gestures are provided here to illustrate gesture based interactions, these examples should not be considered exhaustive.

The display/response of the biometric monitoring device may depend on the device state, e.g., contextual device state and/or intrinsic device mode. Typically, information that deemed as most relevant or otherwise appropriate with regard to the device state may be presented in via the display of the biometric monitoring device, e.g., via a plurality of data display pages, upon the receipt of one or more user inputs. In some cases, information may be displayed regardless of user input, e.g., in response to some other input such as receipt of an email or notification from an external device, or in response to a lack of user input. The biometric monitoring device's response to user input may also change depending on the device state. The following implementations provide several examples of device-state dependent biometric monitoring devices, but are by no means considered exhaustive.

In one implementation, the biometric monitoring device may have a display that changes what is shown, e.g., advances from one data display page to the next, after a user interaction occurs, e.g., after receiving a user input, e.g., as may be indicated by a page advance input such as a button press or other specific act by the user. A specific data type or set of data types may be presented to the user with a data display page when the display first turns on. Subsequent user inputs may cause the display to advance through a succession of different data display pages, each showing different types of information. The information on each data display page (accessed with each subsequent user input) may follow a predetermined, e.g., fixed in code or user-specified, sequential display order. For example, receipt of the first user input may cause a data display page showing the time to be displayed, receipt of the second user input may cause a data display page showing the number of calories burned to be displayed, and the third user input may cause a data display page showing the number of steps the user has taken to be displayed. Another implementation showing the sequential display order of three data display pages of a biometric monitoring device and the data shown on each is illustrated in FIG. 5. In the sequential display order shown in FIG. 5, the three data display pages shown are a timer data display page, a clock data display page, and a steps taken data display page. A first user interaction may cause the display of the biometric monitoring device to turn on (if off) and display the clock data display page. A second user interaction may cause the biometric monitoring device display to advance to a timer data display page. A third user interaction may cause the biometric monitoring device to advance to the steps taken data display page. In many implementations, the sequential display order may be cyclic, e.g., when all of the data display pages in the sequential display order have been displayed, the sequential display order may return back to the first data display page. In the depicted example, a fourth user interaction may cause the biometric monitoring device display to advance back to the timer data display page. A fifth user interaction may then be treated in a manner similar to the second user interaction, a sixth user interaction may be treated similar to the third user interaction, and so forth.

In implementations that allow a user to specify a sequential display order, the biometric monitoring device may be configured to reference sequential display orders downloaded to the biometric device from a remote device, e.g., a paired smartphone or an internet server. A user may specify or modify the user-specified sequential display orders on the smartphone or via a web browser interface and the biometric monitoring device may then download the user-specified sequential display orders for later reference.

It is to be understood that there may be a different number of data display pages than the three data display pages shown, e.g., more or fewer data display pages of information, and that each data display page may display more than one type of information, e.g., a clock also may be displayed on a data display page showing steps taken.

In some implementations, if all the data display pages have been shown, a further user interaction may cause the display to turn off rather than returning to the "first" data display page in the sequential display order as in the sequential display order shown in FIG. 5. In some such implementations, the display may turn off after a set period of time elapses after the last user input. In another implementation, the biometric monitoring device may cause the display to enter a different operation type or series of operation types after a set period of time or set of time periods. For example, the display may first dim after 5 seconds and then turn off completely 10 seconds later.

Figure 6:
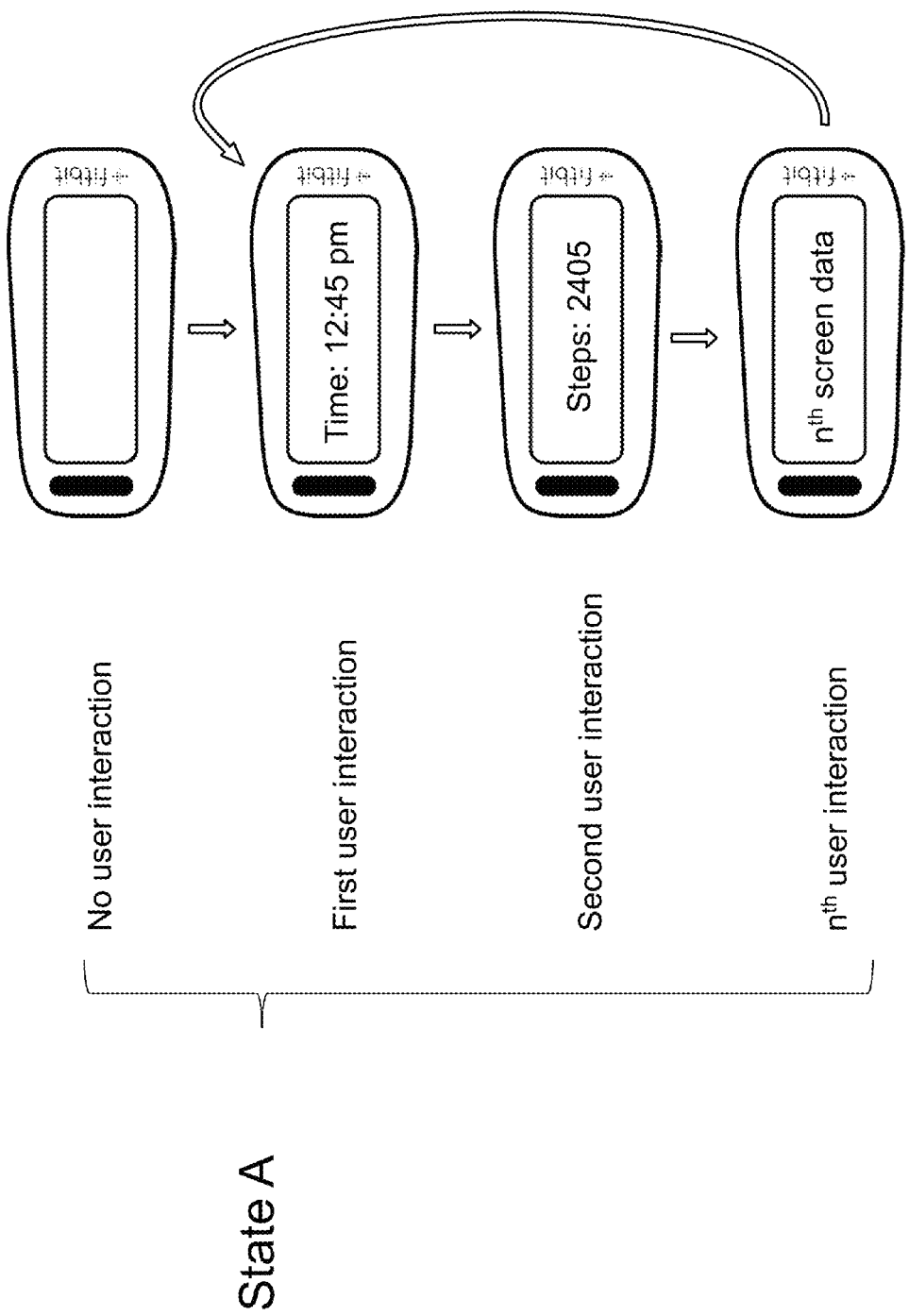
FIG. 6 depicts an example sequential display order for a biometric monitoring device that is operating in a "default" device state (referred to in FIG. 6 as "State A").

In one implementation, the data display page that is displayed on the display of a biometric monitoring device immediately after the display is turned on responsive to receiving a first user input may depend on the device state of the biometric monitoring device. For example, the display may always display a clock data display page responsive to receiving a first user input if the biometric monitoring device is operating in a normal, "default" device state and the display is in the off state when the first user input is received. FIG. 6 depicts an example sequential display order for a biometric monitoring device that is operating in a "default" device state (referred to in FIG. 6 as "State A"). The biometric monitoring device of FIG. 6 has a display that is normally in an off state in the "default" device state so as to conserve power in the absence of any user interaction. In response to a first user interaction, e.g., "first" user interaction received after the display has been turned off, the biometric monitoring device may turn on the display and present a "clock" data display page, e.g., "Time: 12:45 PM." A second, subsequent user interaction may cause the biometric monitoring device display to advance to a "steps taken" data display page, e.g., "Steps: 2405." Further subsequent user interactions may cause the display to advance through additional data display pages, e.g., third through $n^{th}$ data display pages, if such data display pages are normally displayed when the biometric monitoring device is in that default device state.

Figure 7:
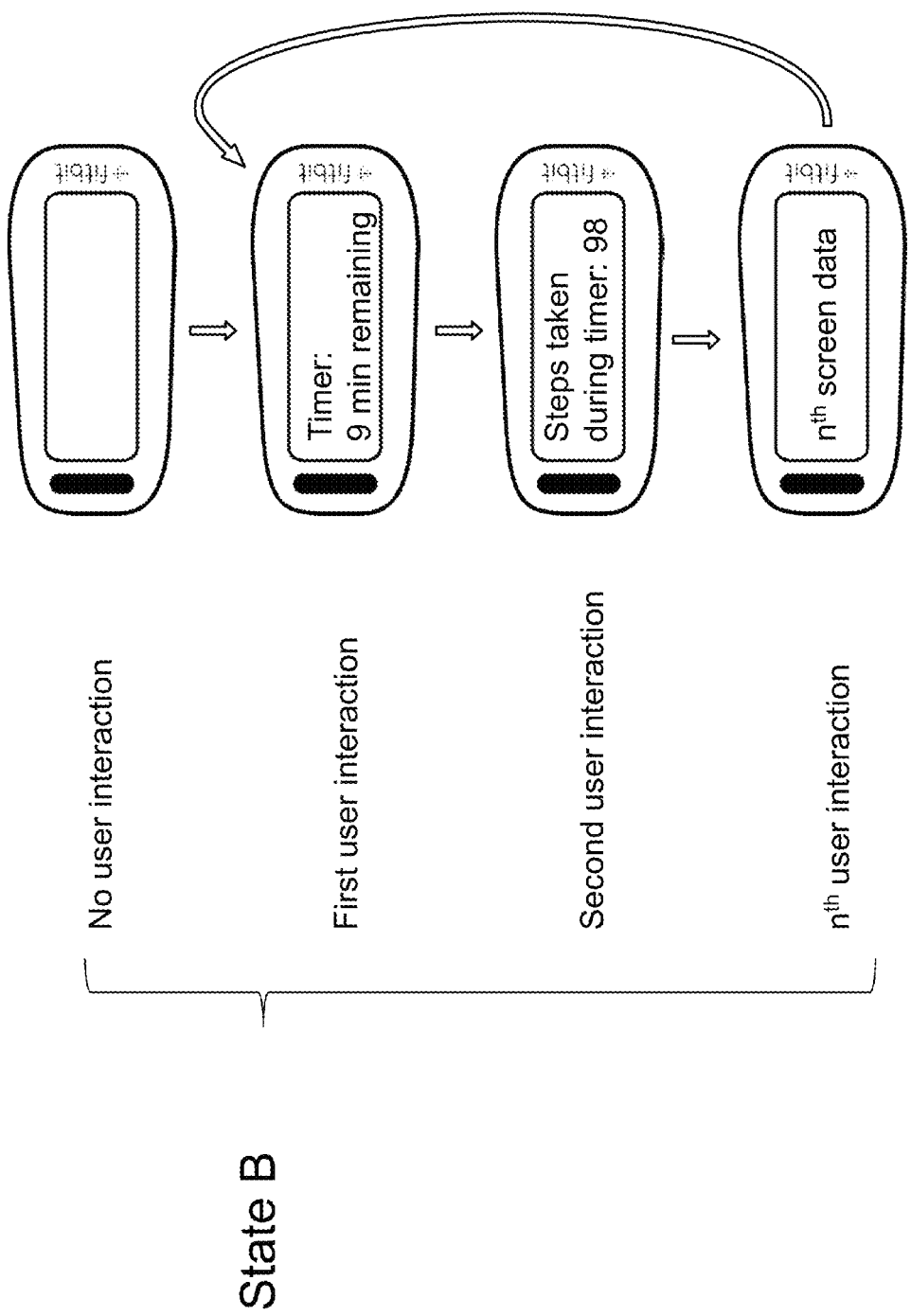
FIG. 7 depicts an example sequential display order for the biometric monitoring device of FIG. 6 but operating in a device state (referred to in FIG. 7 as "State B") that has been modified from the "default" device state to account for a "timer" mode that is active on the biometric monitoring device.

FIG. 7 depicts an example sequential display order for the biometric monitoring device of FIG. 6 but operating in a device state (referred to in FIG. 7 as "State B") that differs from the "default" device state in that a "timer" mode is active on the biometric monitoring device. For example, in the "timer" mode, the biometric monitoring device may track the amount of time remaining in a countdown timer. The biometric monitoring device may also identify biometric data recorded by the biometric monitoring device while the timer is running such that the biometric data recorded while the timer is running may be associated with the operation of the timer. When the "timer" mode is active, the display of the biometric monitoring device, similar to the "default" device state, may ordinarily be kept in an off state to conserve energy. In response to a first user interaction, e.g., "first" user interaction received after the display has been turned off, the biometric monitoring device may turn on the display and present a "timer" data display page, e.g., "Timer: 9 min remaining." A second, subsequent user interaction may cause the biometric monitoring device display to advance to a "steps taken" during timer data display page, e.g., "Steps taken during timer: 98." The "steps taken during timer" data display page and the "steps taken" data display page both show data representing steps taken, but differ with respect to which time periods they refer. For example, the "steps taken" data display page may ordinarily be configured to display the total number of steps taken during the span of a normal day, e.g., from midnight to midnight. By contrast, the "steps taken during timer" data display page may only display the number of steps taken while the timer is running. This may, for example, be of interest to the wearer if they are trying to obtain a certain fitness goal, e.g., taking 1000 steps within 5 minutes. Further subsequent user interactions may cause the display to advance through additional data display pages, e.g., third through $n^{th}$ data display pages, if such data display pages are normally displayed when the biometric monitoring device is in the device state that includes the timer mode. For example, some such implementations may also show the "steps taken" data display page (in addition to the "steps taken during timer" data display page) as part of the sequential display order.

A biometric monitoring device may also be capable of operating in a device state that accounts for a "stopwatch" mode being active in the biometric monitoring device. The "stopwatch" mode may operate in a manner similar to the "timer" mode, but may count up instead of down. When a biometric monitoring device's device state is modified to account for an active "stopwatch" mode on the biometric monitoring device, a "stopwatch" data display page may be inserted into the sequential display order and displayed responsive to a user interaction.

A biometric monitoring device may also be capable of operating in an "annotation" mode that may cause the biometric monitoring device to mark, flag, or otherwise identify data that is gathered while the biometric monitoring device is in the "annotation" mode as being associated with an annotation. The annotation may be a default annotation that may be changed or updated by a user later, or may be automatically assigned based on various parameters. For example, if a biometric monitoring device is placed into an "annotation" mode prior to the wearer going to sleep and then taken out of the "annotation" mode after the wearer wakes up, e.g., via user interactions, the biometric monitoring device may record biometric data that indicates that the wearer was largely stationary and horizontal during the time that the biometric monitoring device was in the "annotation" mode. This, in combination with the time of day that the "annotated" biometric data was collected, may cause the biometric monitoring device to automatically annotate such data as a "sleeping" activity. A wearer of the biometric monitoring device may, alternatively, indicate that the "annotated" biometric data is associated with a particular activity, e.g., by entering a label or other identifier of the activity in association with the annotated data after the biometric data is exported from the biometric monitoring device to a website or other data store or by inputting such a label or other identifier into a device, e.g., a smartphone, that is paired with the biometric monitoring device and within communications range of the biometric monitoring device. In such implementations, a sequential display order similar to that shown in FIG. 7 may be used, except that an "annotation" data display page may be displayed in place of the "timer" data display page. The "annotation" data display page may indicate that the biometric monitoring device is in annotation mode. In some implementations, the "annotation" mode and the "stopwatch" mode may coexist, e.g., when the "stopwatch" mode is active, the "annotation" mode is also active. Thus, the stopwatch data display page may, explicitly or implicitly, indicate that the biometric monitoring device is in the "annotation" mode in addition to displaying a stopwatch.

When a biometric monitoring device is in the "annotation" mode, information related to the activity being annotated may be displayed, e.g., data display pages for various types of biometric data may show quantities limited to biometric data that are measured while the biometric monitoring device is in the "annotation" mode. For example, in the "annotation" mode, a data display page for "steps taken" may only display a quantity of steps that have been taken while the biometric monitoring device is in the "annotation" mode (rather than, for example, the quantity of steps taken throughout the day).

When a biometric monitoring device is in an "annotation" mode that tracks sleep, the sequential display order may cause the display to show data display pages indicating how long the user has been sleeping, a metric of the quality of their sleep, and/or the amount of time remaining before a wake time or alarm.

In some implementations, the biometric monitoring device may be configured to provide an alarm after a threshold associated with biometric data is reached. For example, some biometric monitoring devices may be configured to determine how restfully someone is sleeping while in an annotation mode that tracks sleep. Such a biometric monitoring device may be configured to provide an alarm that may be set to go off after the biometric monitoring device records biometric data indicating that the wearer of the biometric monitoring device has experienced six hours of high-quality sleep. High-quality sleep, for example, may be evaluated based on whether or not the wearer is moving while sleeping. If the wearer of the biometric monitoring device is moving very little or not at all, such data may indicate that the wearer is experiencing "high-quality" sleep. If the biometric data indicates that the wearer of the biometric monitoring device is tossing and turning, then such data may indicate that the wearer of the biometric monitoring device is experiencing "low-quality" sleep. In some such implementations, the biometric monitoring device may be configured to how much "high-quality" sleep has been indicated by the biometric data during a "sleep" annotation mode at regular intervals, e.g., every 10 minutes.

In some implementations of such sleep-quality alarming biometric monitoring devices, the sleep-quality alarm may be an alarm that functions in parallel or in tandem with a time-based alarm. For example, the biometric monitoring device may be configured to trigger an alarm at a specific time or after a specific quantity of high-quality sleep has been indicated while a "sleep" annotation mode is active. If either alarm is triggered, the other alarm may be canceled. In some implementations, the time-based alarm may remain active even after the sleep-quality-based alarm has been triggered; this allows the wearer to continue sleeping even if they have reached their desired number of "high-quality" sleep hours.

In some biometric monitoring device implementations, if it is a certain time period of day, such as the morning, a "morning" mode may be active and the display may show a data display page with time in response to receiving a user input while the display is off.

Additionally, device states such as those disclosed herein may cause a biometric monitoring device in such a device state to change not only the information shown on the data display page displayed by the biometric monitoring device after turning on the display, but also the information displayed on the following data display pages, the order of the data display pages, and the number of data display pages displayed.

The device states disclosed herein may also cause biometric monitoring devices in such device states to change other aspects of the user interface other than the display-centric aspects already discussed in this disclosure. Such other aspects may include, but are not limited to, changing the action performed by a user input, changing to the appearance of, location of, and action associated with virtual buttons on a touch screen, changing the action initiated by user input such as a gesture on a touch sensitive screen, or changing the action initiated by performing a gesture with the device. The device state may also cause aspects of the device other than the user interface to change, including, but not limited to, what type of biometric sensor data is acquired, the method and/or sampling rate of biometric sensor data acquisition, and the power savings strategy of the device.

For example, if a biometric monitoring device is in a device state that actively tracks heart rate, this may cause the display of the biometric monitoring device to show the heart rate on the display after powering on the display responsive to a first user interaction with the device. A heart rate sensor, which may ordinarily be in an "off state" or in a low-sampling rate state, e.g., checking heart rate once every fifteen minutes, may be placed into an on state or a higher-sampling rate state, e.g., monitoring heart rate more or less continuously, while the biometric monitoring device is in the device state where heart rate is being actively tracked.

In another example, if a biometric monitoring device is in a device state associated with the wearer being asleep, it may be less likely for the wearer to input information into or otherwise interact with the biometric monitoring device. Therefore, the biometric monitoring device may decrease the sensitivity of various input detection mechanisms (or even turn the completely off) to reduce the risk of accidental inputs and/or to save power. In other device states, it may be desirable to change the user input method based on the limitations of various input mechanisms in various environments. For example, if a biometric monitoring device is in a device state associated with swimming, e.g., the biometric monitoring device independently determines, e.g., through moisture sensors or pressure sensor data, or is actively placed into a swimming mode by the wearer of the biometric monitoring device, a touchscreen interface for the biometric monitoring device may be deactivated since it may not function well in water. The wearer may instead interact with the biometric monitoring device using physical buttons rather than the touchscreen when the biometric monitoring device is in this device state.

In some implementations, the portable biometric monitoring device may include mechanisms or capabilities for responding to more than one type of user interaction. User interactions may include, but are not limited to, those already disclosed herein, e.g., pressing a button, performing a gesture such as moving your hand in a manner similar to viewing a watch, tapping one or multiple times in a specific pattern, and performing a specific gesture on a touchscreen. Different kinds of user interactions may correspond to different functions. For example, a button press user interaction may cause a data display page showing a first metric related to an activity or physiological signal, e.g., ambulatory motion or cardiac signal may have the metrics step counts and heart rate respectively). An additional user input of a different input method (e.g. by tapping the device one or more times) may trigger display of a second metric related to the same activity or physiological signal. In another implementation, additional user input of a different input method may trigger presentation of a submenu or information unrelated to the previous screen shown. An example of such an interface may be found in FIGS. 10, 11, and 12 (discussed in more depth later in this disclosure).

The information and device states described herein are intended for illustration and should not be interpreted as limitations to the present disclosure. Indeed, a variety of combinations of information and device states are intended within the scope of the present inventions.

In some implementations, some environments/contexts and/or modes may have priority over others in determining the device state and/or display/response if the environments/contexts and/or modes occur simultaneously or within a time window of each other. For example, a biometric monitoring device with a "working" mode that is active during weekday working hours may be configured such that the device state always causes a data display page with a to-do list to be displayed responsive to receiving a first user interaction while the biometric monitoring device display is off regardless of what other modes or environments/contexts the biometric monitoring device is in or experiencing.

Figure 8:
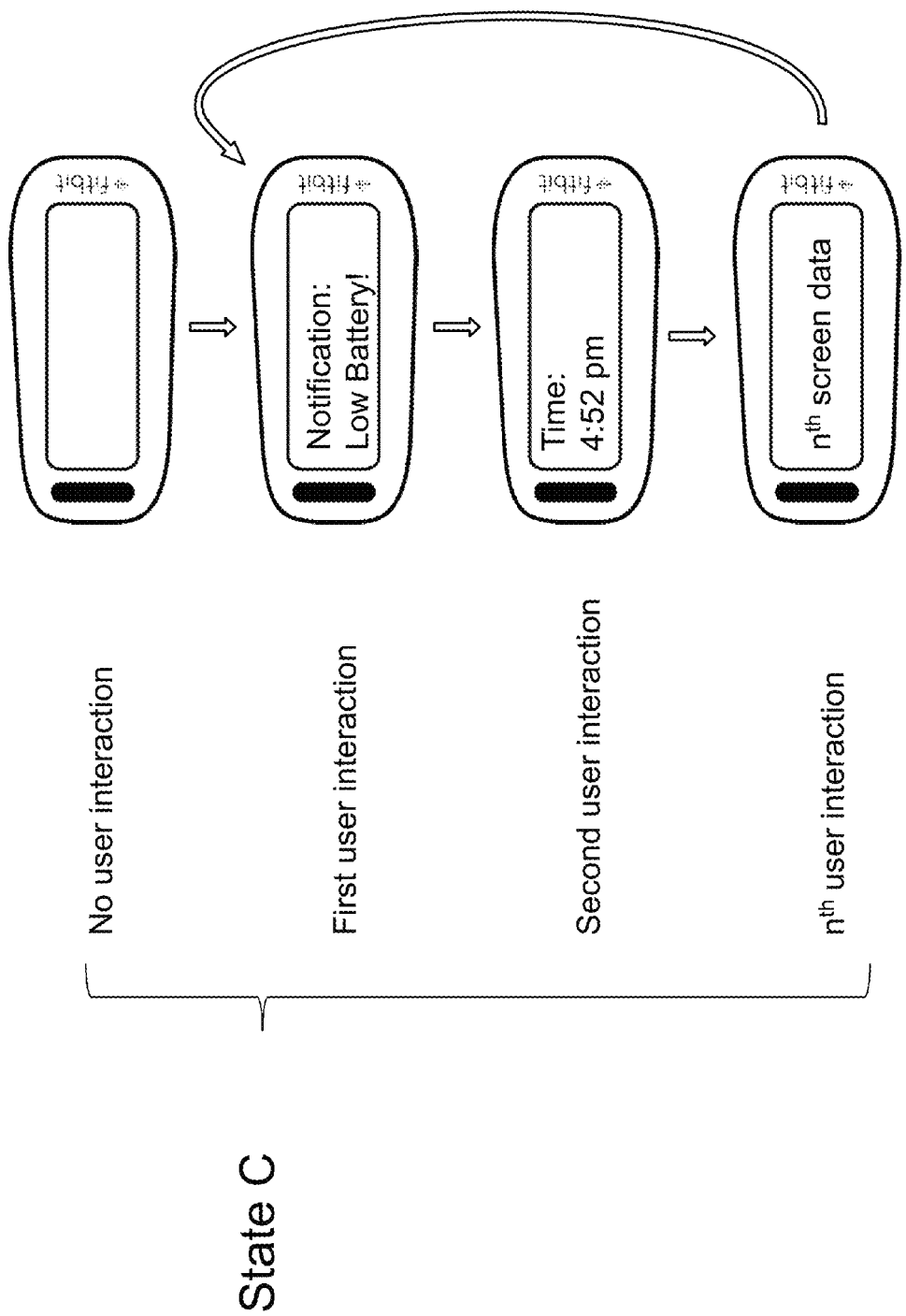
FIG. 8 depicts an example sequential display order for the biometric monitoring device of FIG. 6 but operating in a device state (referred to in FIG. 8 as "State C") that has been modified from the "default" device state to account for a "low battery" mode that is active on the biometric monitoring device.

In another implementation, shown in FIG. 8, a low battery mode may have priority over other modes and may cause the biometric monitoring device to enter a device state where the biometric monitoring device causes the display to show a data display page indicating a low battery warning when the display is first powered on and before data display pages that would normally be displayed are shown.

Figure 9:
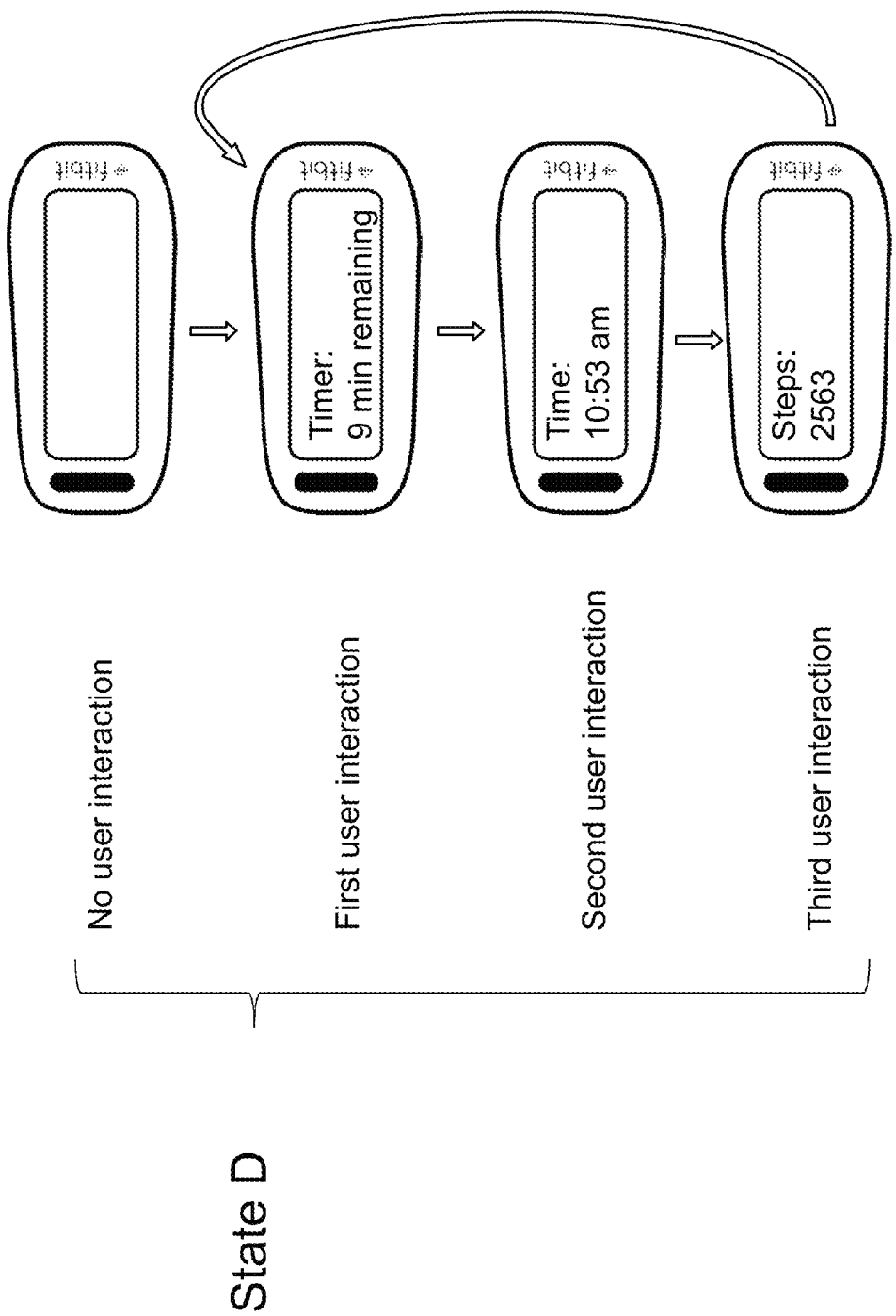
FIG. 9 depicts a sequential display order for a device state (referred to in FIG. 9 as "State D") of an example biometric monitoring device.

FIG. 9 depicts another example of a sequential display order. In FIG. 9, the device state of the example biometric monitoring device advances causes the display to be turned on from an off state and to display a "timer" data display page responsive to a first user interaction received while the display is in an off state. The device state of the biometric monitoring device pictured in FIG. 9 causes further receipt of user interactions to advance through a "time" data display page and a "steps taken" data display page. A fourth user interaction may, in some implementations, cause the display to turn off again. In other implementations, the fourth user interaction may cause the sequential display order to be reset and the "timer" data display page to be shown again.

Additionally, there may be user-specified sequential display orders for each combination of two or more modes, environmental states, and/or contextual states. For example, the user may configure the biometric monitoring device such that when a "work" mode or contextual state is active, e.g., the time is during working hours and a location sensor indicates that the biometric monitoring device is in a location near a pre-defined "work location," simultaneously with an "annotation" mode, the sequential display order may cause a data display page showing how much time the user has spent typing (assuming that the biometric monitoring device can detect typing, e.g., via acoustic or vibratory sensors) for the duration of the annotation mode to be displayed in response to a first button press, a data display page showing the time to be displayed on the display in response to a subsequent button press, and a data display page showing a to-do list to be displayed on the display in response to a further subsequent button press. The user may specify such user-specified sequential display orders using, for example, a web site or a mobile device application that allows the user to edit the sequential display orders and then cause the edited sequential display orders to be uploaded to the biometric monitoring device via a communications link.

In another implementation, a first user interaction may cause the display of a biometric monitoring device to show one of multiple screens depending on the amount of time that has passed since the last user interaction was received or the last time that something was displayed on the display. If the time period between the last user interaction and/or the last time something was displayed on the display meets or exceeds a certain threshold, then a first data display page may be shown on the display, e.g., a "clock" data display page responsive to receipt of a first user interaction while the display is off. If the time period between the last user interaction and/or the last time something was displayed on the display is less than that threshold, then another data display page, e.g., the last data display page that was shown on the display prior to the display being turned off, may be shown responsive to receipt of a first user interaction while the display is off. For example, if a user presses a button on a biometric monitoring device to cause the display of the biometric monitoring device to turn on from an off state, the biometric monitoring device may cause the display to turn on and then display a "clock" data display page if the display has not been on within the previous 1 minute and display the data display page that was displayed on the display when the display entered the off state if the display has been on within the previous 1 minute.

In some implementations, the device state may change not only which data display pages are included in the sequential display order of the data display pages and the order of those data display pages within the sequential display order, but also how the data display pages present the data. For example, in some situations, it may be more important to make the biometric data presented in a data display page legible than to show a high level of detail about such biometric data. For example, if a biometric monitoring device is in a device state associated with the activity of "running," it may be difficult for the wearer of the biometric monitoring device to read small, dense text. Therefore, the biometric monitoring device may, when in the device state associated with the "running" activity, cause the display to present less biometric data or less descriptive text on a data display page than may be displayed on the data display page when the biometric monitoring device is in a device state not associated with a "running" activity, but may also cause such biometric data to be displayed in a larger, easier-to-read font. For example, the device may only display the distance that the user has run in miles rather than display the number of steps taken. In another example, the wearer's age and/or visual acuity score may be used to determine the size of the text, icons, and other visually presented information on the display, and the data display pages may be accordingly modified.

In another implementation, the user may have the ability to modify or define device states and/or to modify their associated display/response characteristics. A user may also or alternatively be able to change what determines that the device is in a certain environmental state, contextual state, and/or mode. For example, a biometric monitoring device may have a default "daytime" mode may be defined as being from sunrise to sunset. However, the user could choose to change this mode to be active within the time period from 2 hours after sunrise to 1 hour before sunset. In another example, a biometric monitoring device may have a default "work" mode that may be determined by detection of the user's proximity to a location associated with work. The user may, if employed in a job that involves continuous travel to unpredictable locations, choose to change the "work" mode to be location-independent and to instead be active during the hours of 8 AM to 5 PM on standard workdays. A user may also choose to use multiple signals to trigger an environmental state, contextual state, or mode. For example, the user may configure their biometric monitoring device such that an "active" contextual state be engaged on their biometric monitoring device whenever the biometric monitoring device senses that the wearer's heart rate is above 90 beats per minute and the wearer's speed is between 3 and 8 miles per hour.

The user may also be able to change the priority of environmental states, contextual states, and/or modes. For example, a user may choose that the "active" environmental or contextual state has the highest priority, that a "work" mode has the second highest priority, and that a "daytime" mode has the lowest priority. Whenever multiple states are detected, the overall device state and the device display/response may be determined by the detected environmental state, contextual state, or mode with the highest priority. In some cases, the user may choose a single, static, device state. The user may be able to modify the display/response associated with this single, static device state.

Some implementations of biometric monitoring devices may include an "alarm" mode that may alert the wearer of the biometric monitoring device (in some cases, even if the wearer is not wearing the biometric monitoring device but is instead nearby) when a particular condition has occurred. For example, some biometric monitoring devices may have the ability to set one or more time-based alarms that may be configured by the wearer to go off when pre-set times are reached. The "alarm" mode may be active when there is any alarm that is set to trigger in the future; in some implementations, the "alarm" mode may only be active if there is an alarm that is set to trigger within some limited future period, e.g., if there is an alarm that is set to trigger within the next 18 hours.

Figure 13A:
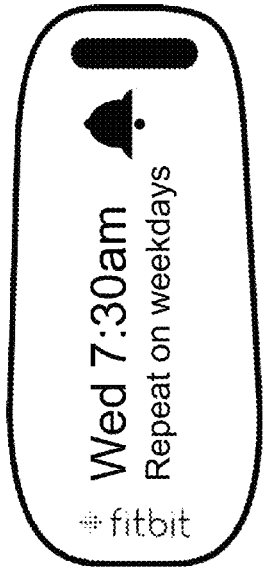
FIGS. 13A through 13F depict various data display pages that may be displayed when an alarm mode is active on a biometric monitoring device.
Figure 13B:
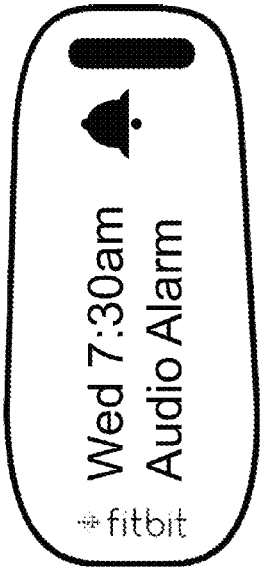
Figure 13C:
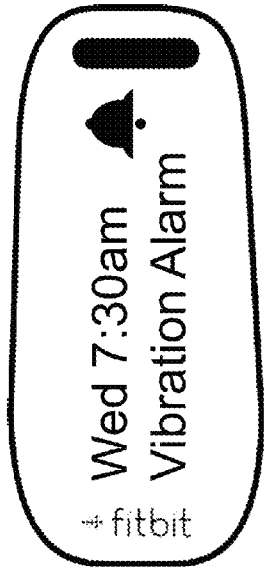
Figure 13D:
Figure 13E:
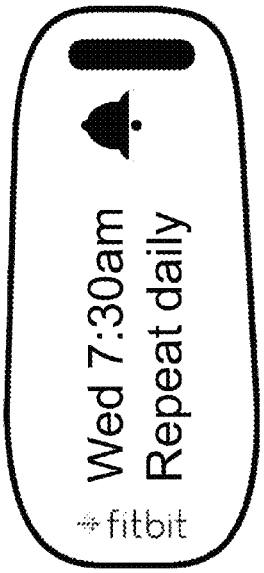
Figure 13F:
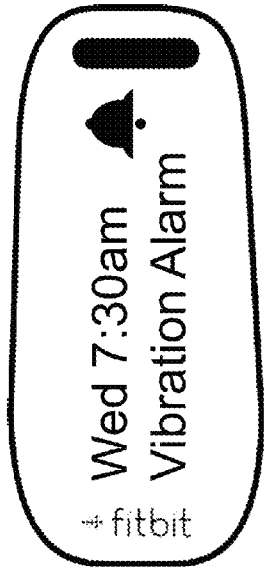

A biometric monitoring device with an active alarm mode may have a device state that may cause "alarm" data display pages to be shown as part of the sequential display order of the biometric monitoring device. The "alarm" data display pages may include information pertaining to future alarms that are set on the portable biometric device (and/or on a secondary computing device in communication with the biometric monitoring device). In some implementations, the time of day and the day of the week that the next alarm will go off may be displayed as illustrated in FIG. 13A. Other information pertaining to one or more alarms set on the biometric monitoring device (or a secondary computing device in communication with the biometric monitoring device) may include but is not limited to the next alarm alert characteristics, e.g., vibration, vibration intensity, audio, volume, light, light intensity, sunrise simulation, etc., the reason for the alarm, e.g., appointment, meeting, time to wake up, time to go to sleep, etc., whether the alarm is to be repeated, how long (or how many times) the alarm will be repeated, the periodicity of a repeating alarm, e.g., once every week for the next 4 months, and so forth as illustrated in FIGS. 13B, 13C, 13D, 13E, and 13F.

In one implementation, the portable biometric monitoring device may have an alarm clock function intended to wake the wearer or user from sleep. Similar to the way a conventional alarm clock functions, the wearer or user may have the ability to set the alarm clock to "snooze," i.e., temporarily stop the alarm for a short period of time, typically minutes, and then have the alarm re-trigger. In a conventional alarm clock, a button on the alarm clock allows the user to set it to snooze. A portable biometric monitoring device may also be set to snooze by pressing or touching a button on the biometric monitoring device one or more times as illustrated in FIG. 4. In one implementation, the button may be a capacitive touch button or touch control. In another implementation, the biometric monitoring device may have a touch screen. The user may be required to perform a touch-input gesture on the touchscreen in order to set the biometric monitoring device to snooze. The touch screen may provide visual guides on the screen so as to aid the user in performing the correct gesture. For example, the user may have to trace an "S" on the touch screen to enter snooze mode. If the user would like to make it more difficult to turn off their alarm or to set it to snooze in the morning, a more difficult gesture may be required, e.g., as specified in a programmed setting within the portable biometric monitoring device, in order to turn off the alarm or set the alarm to snooze. This may be useful in cases where the user has a habit of "snoozing" multiple times. In some implementations, the gesture required to turn off snooze mode may be randomized or changed with each successive alarm. This may require the user to open their eyes to observe the gesture required and then tailor their input to the required gesture. This may assist in rousing stubborn sleepers.

In another implementation, the portable biometric monitoring device may include a motion sensor. The motion sensor may be configured to detect gestures that the user makes with the part of the body to which the biometric monitoring device is coupled. For example, the biometric monitoring device may be coupled to the user's wrist with a band. To set the device to snooze, the user may twist their wrist while wearing the biometric monitoring device.

In another embodiment, a gesture may be performed on the device with a body part to which the device is not coupled. For example, the user may tap a biometric monitoring device worn on their forearm with a finger of the opposite hand to set the biometric monitoring device to snooze the alarm.

While the above discussion has focused on a variety of different implementations, the following discussion explores some of the techniques discussed above in greater detail.

Figure 14:
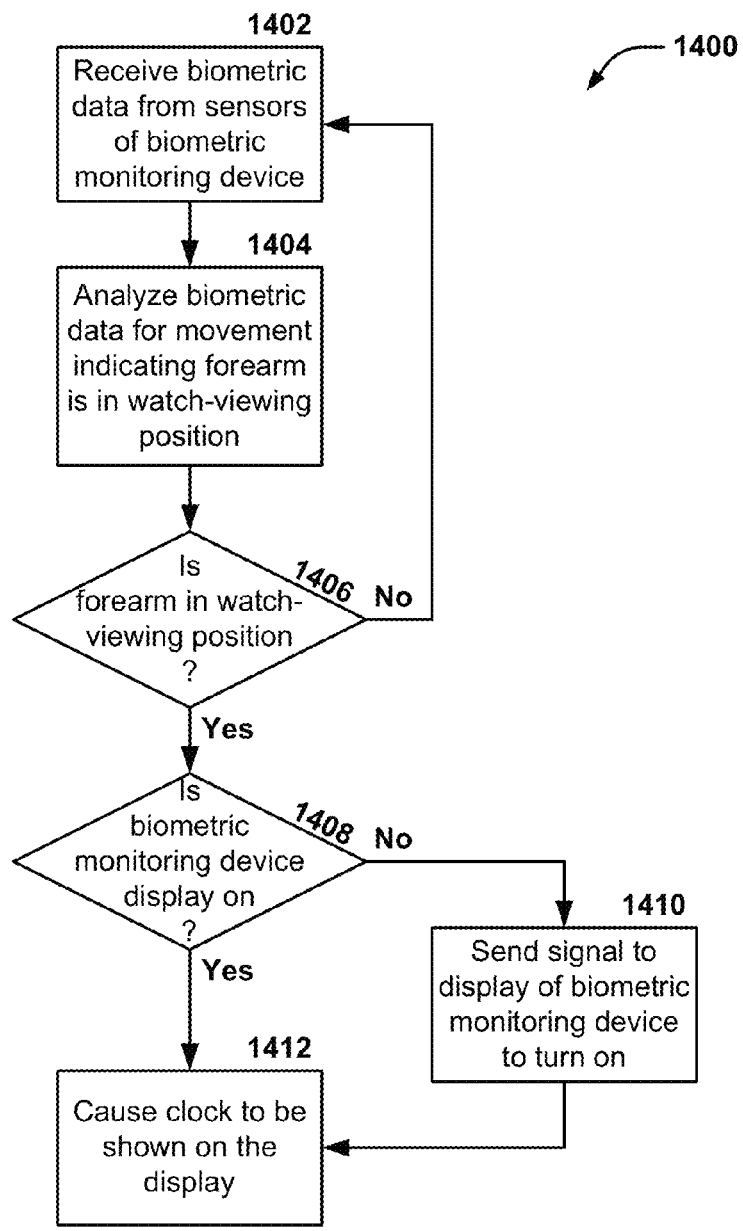
FIG. 14 depicts a flow diagram for a technique that may be used to cause a biometric monitoring device to function as a watch responsive to data received from biometric sensors within the biometric monitoring device.

FIG. 14 depicts a flow diagram for a technique that may be used to cause a biometric monitoring device to function as a watch responsive to data received from biometric sensors within the biometric monitoring device.

The technique 1400 may begin in block 1402 with the receipt of data by a processor or processors of a biometric monitoring device from biometric sensors of the biometric monitoring device. Such data may be analyzed in block 1404 to determine if the biometric data indicates that the biometric monitoring device has moved in a manner consistent with the movement that a wrist-mounted biometric monitoring device would experience if worn on a person's forearm while the person moves that forearm into a position typically assumed when a person is checking their watch. For example, if the biometric data indicates that the person's forearm (and the biometric monitoring device worn on that forearm) has moved from a position generally aligned with the sagittal and frontal planes of the person to a position generally aligned with the frontal and transverse planes of the person, e.g., the person has moved their forearm from a position generally parallel to the long axis of their body to a position that crosses over their torso in a left-to-right (or right-to-left) direction, such an indication may be identified as indicating that the detected movement corresponds with motion consistent with the motions that a person's forearm may experience when the person checks their watch. In other implementations, the biometric monitoring device may analyze the biometric data it collects to determine if the biometric monitoring device has experienced movement consonant with movement corresponding with adduction of the person's wrist joint with respect to the mid-sagittal plane of the person and medial rotation of the hand connected to the wrist joint. In yet other implementations, the biometric monitoring device may analyze the biometric data it collects to determine if the biometric monitoring device has experienced movement corresponding with motion experienced by the distal end of a person's forearm with flexure of the forearm about the forearm's elbow joint.

In block 1406, the processor or processors of the biometric monitoring device may evaluate the biometric data to determine if the biometric monitoring device has received biometric data indicating that the biometric monitoring device (and the forearm upon which it is worn) is in a watch-viewing position with respect to the wearer.

If the processor or processors determine in block 1406 that the biometric monitoring device is not in a watch-viewing position, the technique may return to block 1402 and further biometric data may be received and analyzed.

If the processor or processors determine in block 1406 that the biometric monitoring device is in a watch-viewing position, then the technique may proceed to block 1408. In block 1408, the processor or processors may determine if the display of the biometric monitoring device is on or otherwise already displaying content. If not, then the processor or processors may cause the display to turn on, e.g., by sending a power-on signal to the display, in block 1410 before proceeding to block 1412. In block 1412, the processor or processors may cause a data display page showing a clock to be shown on the display. In this manner, the wearer of the biometric monitoring device does not need to perform any other actions to cause the display of the biometric monitoring device to show the time other than those that the wearer would generally do when checking a watch that always shows the time. This also allows the display of the biometric monitoring device to be powered off most of the time and only powered on under certain conditions, e.g., such as when the wearer "checks" their watch/biometric monitoring device.

In some such implementations, in block 1412 the biometric monitoring device may show a data display page other than a clock data display page. For example, the biometric monitoring device may show a data display page that has been defined as being particularly pertinent to an environmental or contextual state that is determined based on the biometric data collected by the biometric sensors of the biometric monitoring device. For example, if an environmental or contextual state associated with "running" is active on the biometric monitoring device, in block 1412, the biometric monitoring device may display a "distance run" data display page or a "running pace" data display page instead of a "clock" data display page.

Figure 15:
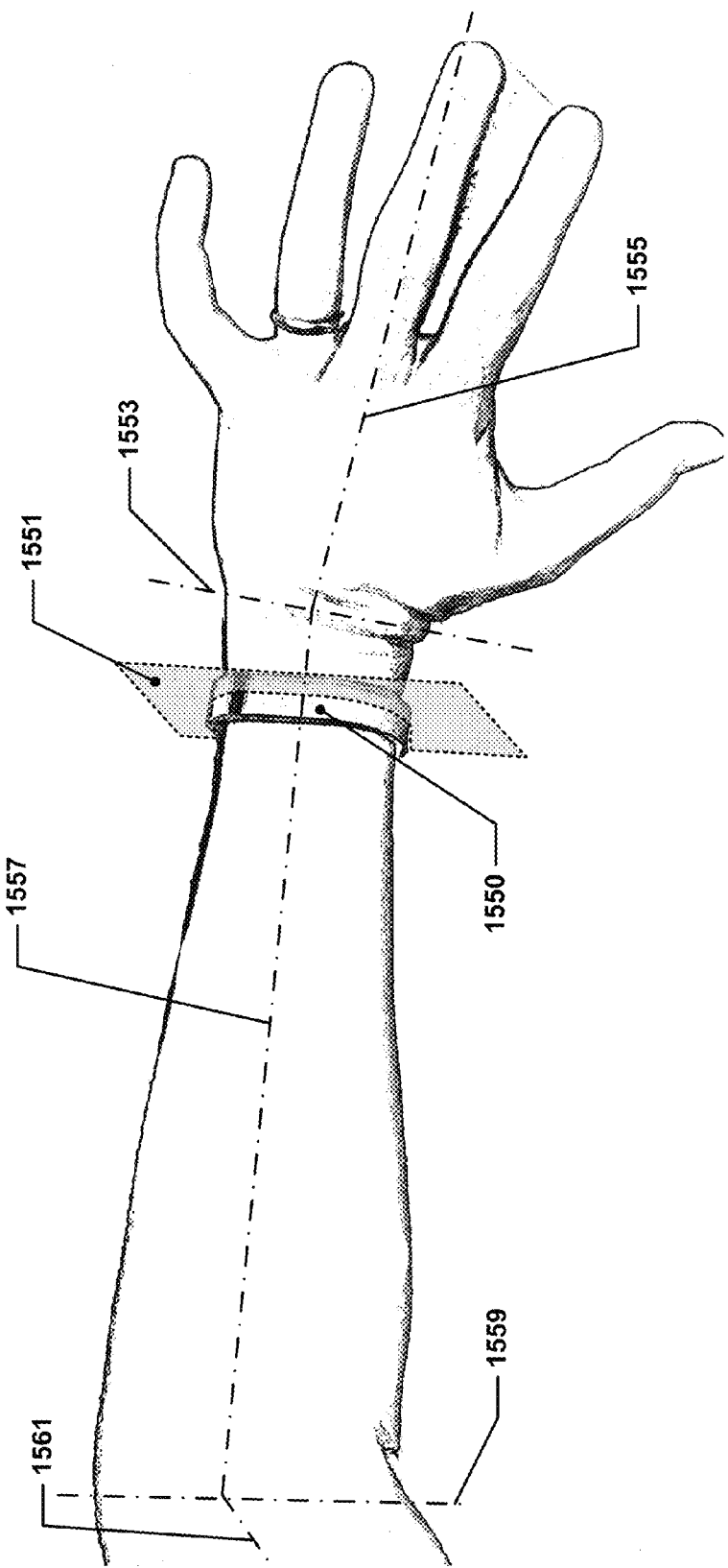
FIG. 15 depicts a person's arm, forearm, and hand with a biometric monitoring device worn on the forearm.

FIG. 15 depicts a person's arm, forearm, and hand with a biometric monitoring device worn on the forearm. In FIG. 15, a person's "arm" is shown. In everyday speech, the term "arm" is typically used to refer to the entirety of the limb connected to a person's shoulder. However, as used herein, the term "arm" refers to the portion of that limb located between the shoulder joint and the elbow joint of that limb. The term "forearm" refers to the portion of that limb between the elbow joint and the wrist joint. The forearm may encompass a portion of the limb that may often be called the "wrist," e.g., the portion of the forearm on which a person may wear a watch or bracelet. This disclosure uses the conventions outlined in Joseph E. Muscolino's "Kinesiology: The Skeletal System and Muscle Function," Second Edition (2011), when discussing various body parts or other kinesiological concepts.

Since a person's arm and forearm are organic structures with widely-varying appearances from person to person, it may be useful to utilize a common reference framework when discussing such a limb or when discussing items that may be worn on such a limb. For example, despite the wide variation in shape and size of forearms in the general population, every normal forearm will have a forearm axis 1557 that is substantially aligned with the longest dimension of the forearm. Another way of thinking of the forearm axis 1557 is as the axis that passes through the nominal centers of rotation of the wrist joint and the elbow joint. In addition to a forearm axis, it may be useful to refer to an elbow axis 1559 and a wrist axis 1553. The elbow axis 1559 may generally define the pivot axis of the forearm about the elbow joint during flexion and extension of the forearm, and the wrist axis 1553 may generally define the pivot axis of the hand about the wrist joint during flexion and extension of the hand (in reality, some of these joints are capable of complex, multi-axial rotation—the pivot axis, as used herein, refers to the axis about which the greatest extent of rotational motion is possible for a joint). An arm axis 1561 may be generally aligned with the long dimension of the arm and may pass through the center of rotation of the elbow joint and the center of rotation of the shoulder joint (not pictured). A hand axis 1555 may pass through the center of the wrist joint and generally in a direction aligned with the middle finger of the hand when at full extension.

As can be seen, the biometric monitoring device 1550 may be located in or on a wristband that encircles the forearm near the wrist (although some users may wear such bands at a loose enough setting that the band may slide over the wrist joint area itself; such bands are still considered to be configured to be worn around the wearer's forearm, however). The wristband may generally define a wristband plane 1551 that is substantially perpendicular to the forearm axis 1557.

Figure 16:
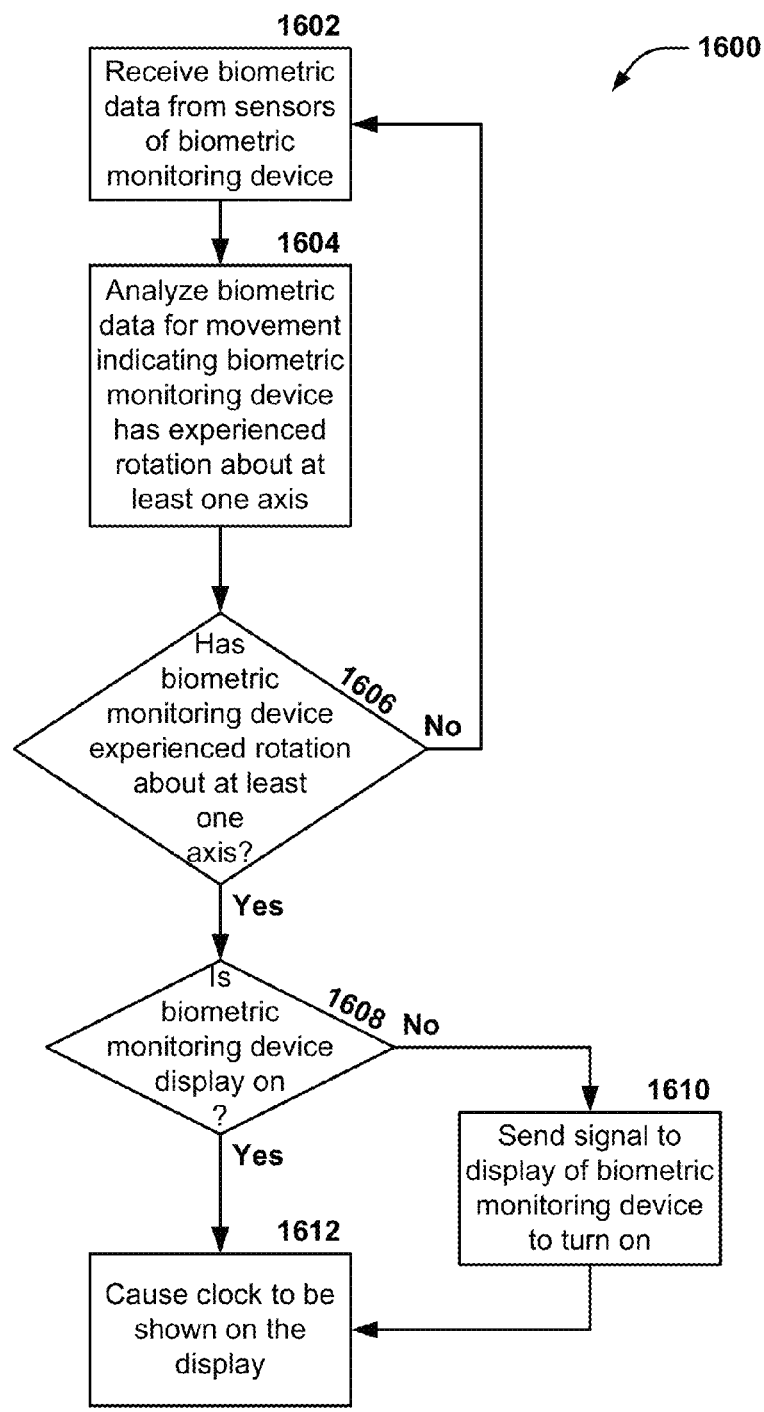
FIG. 16 depicts a flow diagram for a further technique that may be used to cause a biometric monitoring device to function as a watch responsive to data received from biometric sensors within the biometric monitoring device.

FIG. 16 depicts a flow diagram for a further technique that may be used to cause a biometric monitoring device to function as a watch responsive to data received from biometric sensors within the biometric monitoring device.

The technique 1600 may begin in block 1602 with the receipt of data by a processor or processors of a biometric monitoring device from biometric sensors of the biometric monitoring device. Such data may be analyzed in block 1604 to determine if the biometric data indicates that the biometric monitoring device has rotated about at least one axis. For example, if the biometric data indicates that the biometric monitoring device has rotated about an axis such as the forearm axis 1557, such an indication may be interpreted as indicating that the wearer of the biometric monitoring device has rotated their wrist (and thus caused the portion of the forearm adjacent to the wrist and on which the biometric monitoring device is worn to experience similar rotation about the forearm axis). Such rotation may be detected using any of a variety of different techniques. If a gyroscope sensor is included in the biometric monitoring device, the data from such a sensor may be used to determine rotational speed and orientation of the biometric monitoring device. If accelerometers are included in the biometric monitoring device, the accelerations measured by the accelerometers may be used to calculate rotational speed and rotational orientation. For example, the Earth's gravitational field may provide a reference frame for the acceleration data that allows rotational orientation or speed based on tri-axial acceleration measurements to be calculated. Similarly, if a magnetometer is included in the biometric monitoring device, the Earth's magnetic field may be used as a reference frame to determine the absolute orientation of the biometric monitoring device relative to the Earth's surface.

In some implementations, the processor or processors of the biometric monitoring device may be configured to identify rotational movements that are more complex than simple rotation about the forearm axis. For example, when a person moves their forearm from a relaxed position, e.g., the anatomic position, to a position with the forearm generally aligned with the transverse plane and the frontal plane, such motion may involve compound rotation about an axis parallel to the elbow axis 1559 and about an axis parallel to the forearm axis 1557. In terms of an absolute coordinate system, this may translate to triaxial rotations.

In block 1606, the processor or processors of the biometric monitoring device may evaluate the biometric data to determine if the biometric monitoring device has received biometric data indicating that the biometric monitoring device has experienced rotation about at least one axis.

In some implementations, the biometric data may be further evaluated to determine if the rotational movement or orientation, if such is detected, meets certain minimum requirements. For example, the processor or processors may be further configured to determine if detected rotational movement is at least at a rate of 90°/sec and through a substantially continuous rotation of at least 45° about the forearm axis. In other implementations, the processor or processors may be further configured to determine if the detected rotational movement is at least one of the rotational rates in the group including at least 90° per second, at least 60° per second, at least 45° per second, and at least 30° per second. In such implementations, the processor or processors may also be further configured to determine if the detected angular displacement/continuous rotation is at least one angular displacement in the group including at least 90°, at least 60°, at least 45°, and at least 30°.

Such filtering may be used to eliminate spurious rotational movement that is generally classifiable as being unrelated to the motions typically experienced by a person's forearm when the person looks at a wristwatch. For example, when a person walks, they may swing their arms, which may cause the biometric sensors of a biometric monitoring device worn on the person's forearm to cyclically rotate about an axis parallel to the person's shoulder axis. Such rotation, however, would not involve rotation about the person's forearm, however, and may thus be screened out as an indicator of a watch-viewing position.

The biometric sensors used to determine whether the biometric monitoring device has experienced motion consistent with movements a person may make to bring their forearm into a watch-viewing position may be selected from a wide variety of different sensor types, including single-axis or multi-axis gyroscopes, single-axis or multi-axis accelerometers, magnetometers, electromagnetic field sensors, laser rangefinder sensors, Doppler radar sensors, and altimeter sensors. A pair of spaced-apart tri-axial accelerometers may provide a particularly cost-effective mechanism for measuring 3-dimensional movements of a biometric monitoring device, and the data collected from such sensors may be sufficient for determining whether the biometric monitoring device has experienced motion consistent with movements a person may make to bring their forearm into a watch-viewing position.

In some implementations, the determination as to whether the forearm on which the biometric monitoring device is worn has moved into a watch-viewing position may be performed using only data from accelerometers in the biometric monitoring device.

If the processor or processors determine in block 1606 that the biometric monitoring device has not experienced rotation about at least one axis, the technique may return to block 1602 and further biometric data may be received and analyzed.

If the processor or processors determine in block 1606 that the biometric monitoring device is in a watch-viewing position, then the technique may proceed to block 1608. In block 1608, the processor or processors may determine if the display of the biometric monitoring device is on or otherwise already displaying content. If not, then the processor or processors may cause the display to turn on, e.g., by sending a power-on signal to the display, in block 1610 before proceeding to block 1612. In block 1612, the processor or processors may cause a data display page showing a clock to be shown on the display. In this manner, the wearer of the biometric monitoring device need not perform any other actions to cause the display of the biometric monitoring device to show the time other than those that the wearer would generally do when checking a watch that always shows the time. This also allows the display of the biometric monitoring device to be powered off most of the time and only powered on under certain conditions, e.g., such as when the wearer "checks" their watch/biometric monitoring device.

Figure 17:
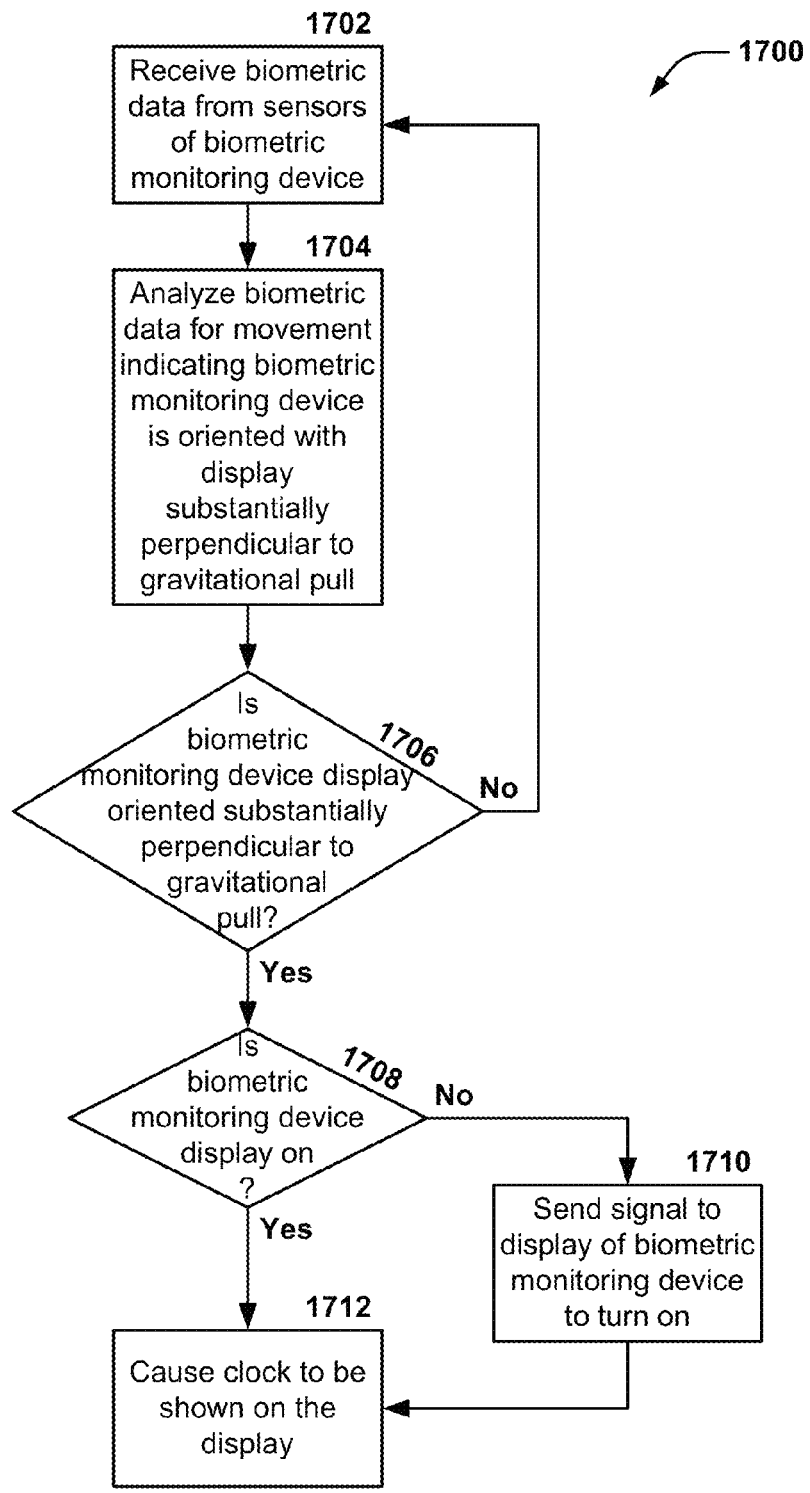
FIG. 17 depicts a flow diagram for yet another technique that may be used to cause a biometric monitoring device to function as a watch responsive to data received from biometric sensors within the biometric monitoring device.

FIG. 17 depicts a flow diagram for yet another technique that may be used to cause a biometric monitoring device to function as a watch responsive to data received from biometric sensors within the biometric monitoring device.

The technique 1700 may begin in block 1702 with the receipt of data by a processor or processors of a biometric monitoring device from biometric sensors of the biometric monitoring device. Such data may be analyzed in block 1704 to determine if the biometric data indicates that the biometric monitoring device has moved from an orientation where a normal to the display of the biometric monitoring device is substantially unaligned with the Earth's gravitational field, e.g., the display is oriented such that a normal to the display makes an angle of more than 30° with the maximum gravitational strength vector at that location, to an orientation where the normal of the display of the biometric monitoring device is substantially aligned with the Earth's gravitational field, e.g., the display is oriented such that the normal to the display makes an angle of 30° or less with the maximum gravitational strength vector at that location. The boundaries of such orientation determinations may be modified from the 30° limits discussed above. Such angular limits may be selected based on empirical measurements that indicate the typical orientations of watch faces when people check their watches.

If the processor or processors determine in block 1706 that the biometric monitoring device is not in a watch-viewing position, the technique may return to block 1702 and further biometric data may be received and analyzed. The biometric monitoring device may also screen the biometric data to prevent unnecessary display of a clock data display page. For example, if the display of the biometric monitoring device is determined to have been in substantially alignment with the maximum gravitational strength vector for more than a first amount of time, e.g., 30 seconds, or if the clock data display page has been displayed since the last time the display was determined to be in the non-aligned position, then the processor or processors may determine that the biometric monitoring device is not in a watch-viewing position even if the biometric data indicates that it physically is in such a position. The user may need to "reset" the biometric monitoring device orientation by placing it in the substantially unaligned position and then moving it back to the substantially aligned position.

If the processor or processors determine in block 1706 that the biometric monitoring device is in a watch-viewing position, then the technique may proceed to block 1708. In block 1708, the processor or processors may determine if the display of the biometric monitoring device is on or otherwise already displaying content. If not, then the processor or processors may cause the display to turn on, e.g., by sending a power-on signal to the display, in block 1710 before proceeding to block 1712. In block 1712, the processor or processors may cause a data display page showing a clock to be shown on the display. In this manner, the wearer of the biometric monitoring device does not need to perform any other actions to cause the display of the biometric monitoring device to show the time other than those that the wearer would generally do when checking a watch that always shows the time. This also allows the display of the biometric monitoring device to be powered off most of the time and only powered on under certain conditions, e.g., such as when the wearer "checks" their watch/biometric monitoring device.

Each of the techniques outlined in FIGS. 14, 16, and 17 may be used to provide for a biometric monitoring device that may be worn on a person's forearm and that may display the time in a transiently-visible manner, i.e., the biometric monitoring device may normally not display the time (to conserve power or to achieve a certain design aesthetic) but may display the time in a transient manner, e.g., for a period of a few seconds, in response to the natural motions that people normally make when checking a standard watch, e.g., moving the forearm into a position that allows for convenient reading of a watch.

It is to be understood that there may be a variety of techniques in addition to those described herein that may be used to determine that a biometric monitoring device has experienced motion consistent with a person's typical watch-checking movements. Biometric monitoring devices providing transient clock or time display responsive to such watch-checking movements using techniques other than those specifically described herein are also considered to be within the scope of this disclosure.

Additionally, it is to be understood that the techniques described herein for providing a transiently-visible clock or time display are not necessarily limited to biometric monitoring device implementations, but may also be implemented in other forearm-worn devices that include sensors that may allow for a determination that the forearm-worn device is experiencing motion consistent with the wearer checking a watch on the forearm. For example, a bracelet that appears to be purely cosmetic may have a hidden display that may display the time when the forearm wearing the bracelet is moved into a watch-viewing position. The bracelet may have a processor or processors, one or more sensors, and, of course, the display. The bracelet may not, however, actually store the gathered data for any extended period of time (unlike a biometric monitoring device). These non-biometric monitoring implementations are also considered to be within the scope of this disclosure.

It is to be understood that the techniques discussed above with respect to FIGS. 14, 16, and 17 may involve, for example, a combination of a mode and an environmental or contextual state. For example, the environmental or contextual state reflected in the biometric data may indicate that the biometric device is being subjected to a watch-viewing motion; this may be interpreted as a user interaction with the biometric monitoring device which may, in turn, cause the biometric monitoring device to enter a "wristwatch" mode. The device state (or activity state) of the biometric monitoring device may then change to account for the "wristwatch" mode being active.

As discussed above, certain modes may have priority over other modes, environmental states, or contextual states. The "wristwatch" mode may, for example, have priority over all or nearly all other modes, and the device state that includes the "wristwatch" mode may therefore prioritize the display of the data page or data pages that are associated with the "wristwatch" mode.

In some implementations, the biometric monitoring device may, after displaying a clock or time data display page in response to a watch-viewing motion, display a data display page relevant to other modes of the biometric monitoring device. For example, after first displaying a clock or time data display page, the biometric monitoring device may next display the last data display page that was displayed on the display prior to the most recent power-down of the display.

Other implementations of device-state dependent biometric monitoring devices are discussed below with reference to FIGS. 18 through 23. While these techniques and examples are provided in the context of biometric monitoring devices, further implementations may be implemented in other contexts, e.g., other devices having some, perhaps incidental, biometric sensing capabilities.

Figure 18:
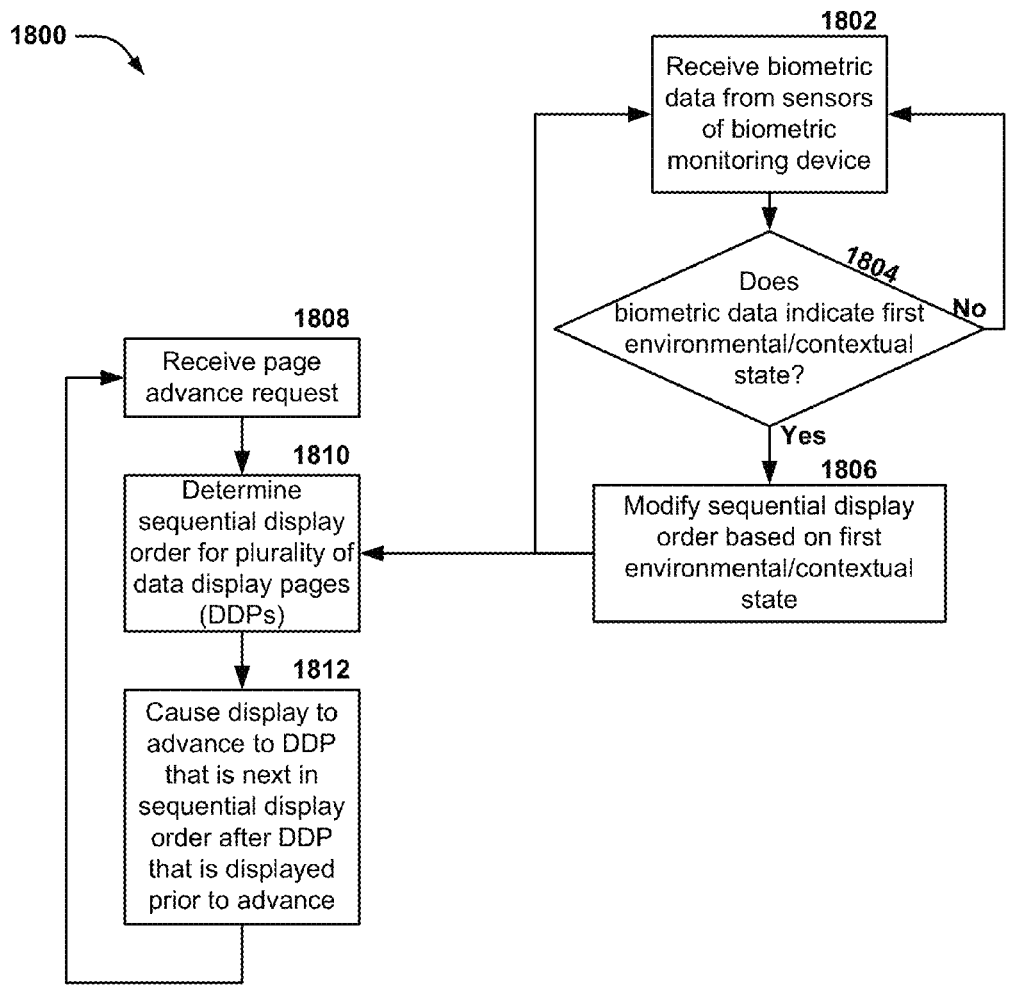
FIG. 18 depicts a flow diagram of a technique for modifying the sequential display order of an example biometric monitoring device.

FIG. 18 depicts a flow diagram of a technique for modifying the sequential display order of an example biometric monitoring device. In FIG. 18, the technique 1800 may begin in block 1802 with the receipt of biometric data from biometric sensors of a biometric monitoring device. The biometric data may be evaluated in block 1804 to determine if the biometric data indicates a first environmental or contextual state. For example, the biometric data may cause a "walking" or "running" environmental or contextual state to become active on the biometric monitoring device. It is to be understood that for FIG. 18, as well as FIGS. 19 through 23, the first environmental or contextual state and/or the second environmental or contextual state (if discussed) may be become active responsive to biometric data collected by the biometric monitoring device biometric sensors If block 1804 does not cause the first environmental or contextual state to become active on the biometric monitoring device, the technique may return to block 1802. If block 1804 does cause the first environmental or contextual state to become active on the biometric monitoring device, then the technique may proceed to block 1806. In block 1806, the sequential display order of data display pages that may be advanced through on the display of the biometric monitoring device may be modified based on the first environmental or contextual state. For example, the sequential display order may be modified to include data display pages that are relevant to the contextual states and/or environmental states that are active as a result of the biometric data. The sequential display order may also be modified such that the order through which those data display pages may be advanced may change from environmental or contextual state to environmental or contextual state.

While blocks 1802 through 1806 are performed, blocks 1808 through 1812 may also be performed. In block 1808, a page advance request may be received by the biometric monitoring device. The page advance request, for example, may be generated by a person pressing a button of the biometric monitoring device, by tapping the housing of the biometric monitoring device, or by some other mechanism. The page advance request represents a request by a user for the biometric monitoring device to advance from the data display page currently displayed (if any) to the next data display page in the sequential display (as modified by whatever environmental or contextual state or states are currently active). If the currently-displayed data display page is the last data display page in the sequential display order, the data display page that is first in the sequential order may be treated as the "next" data display page in the sequential display order. This may be referred to herein as a "modular" or "modulo" sequential display order.

In other implementations, instead of a "modular" or "modulo" sequential display order, the sequential display order may reverse when the last data display page in the sequential display order is displayed. For example, if a sequential display order consists of data display pages A, B, C, and D, and data display page D is displayed, the sequential display order following the display of data display page D may be C, B, and A (and then B, C, and D after the data display page A is displayed).

In some other implementations, e.g., ones in which a user may be able to both advance through and retreat through data display pages, the sequential display order may not reverse when the last data display page in the sequential display order is displayed, but instead the user may only be allowed to retreat from the last data display page to the data display page just prior to the last data display page (and similarly, when the first data display page in the sequential display order is shown, the user may only be allowed to advance to the next data display page and may not be allowed to retreat from the first data display page in the sequential display order). It is to be understood that within the context of this disclosure, generally any features that are discussed in the context of "page advance requests" and "advancing" through data display pages may also be implemented using "page retreat requests" and may, correspondingly, involve retreating through the sequential display order of data display pages (in a direction opposite that used to advance through the sequential display order of the data display pages).

The sequential display order, it is to be understood, refers to an end result as perceived by a user of a biometric monitoring device, i.e., as the user advances through the data display pages that are displayable at a given point in time, the user may be presented the data display pages in a particular order and perceive such presentation as representing a sequential display order. There may be many techniques that are used to provide such an effect to a user, and it is to be understood that regardless of the particular technique used to achieve such an effect, all such techniques are considered to be within the scope of this disclosure and as providing or managing a sequential display order.

As discussed above, there may be many ways to manage and track the sequential display order. The discussion herein generally treats the sequential display order as a look-up table where the currently-display data display page may be looked up and the next data display page in the sequential display page identified. Another alternative is to manage and track the sequential display order using a mechanism such as a circular shift register. In such an implementation, the currently-display data display page may generally always be located in the same absolute position within the shift register, e.g., "last," and the next data display page to be shown may generally always be located in the same absolute position within the shift register, e.g., "first." When a user advances from the currently-displayed data display page to the next data display page in the sequential display order, all of the entries in the circular shift register may advance as well. There are a multitude of other techniques that may be used to track and manage the sequential display order in addition to those discussed herein. It is to be understood that modification of a sequential display order, regardless of the particular mechanism used to track and manage the sequential display order, based on the current environmental or contextual state of a biometric monitoring device is within the scope of this disclosure.

In some implementations, the sequential display order may be implicitly defined instead of explicitly defined. For example, a biometric monitoring device may instead utilize a set of heuristics or rules that ultimately determine what data display pages are displayed in association with a particular device mode, environmental state, contextual state, or combination thereof, and may apply those heuristics or rules in response to each page advance request to determine which data display page will be displayed next. Such implicit sequential display orders are considered to be within the scope of this disclosure as well, and it is to be understood that "sequential display order" as used herein refers to both implicit and explicit sequential display orders.

In other implementations, a biometric monitoring device may have multiple sets of data display pages specified in separately-stored lists. A biometric monitoring device may be in a device state in which one such list of data display pages is used to select data display pages for display in that device state and may then transition to another device state in which another list of data display pages is used to select data display pages for display. The data display pages for each list may remain fixed, i.e., no re-ordering of the data display pages for each list may occur, and no data display pages may be added or removed from the lists. However, transitioning from the display of data display pages from one list to the display of data display pages from the other list is still considered, under the conventions of this disclosure, to involve the modification of the sequential display order used to determine the order in which data display pages are shown responsive to page advance requests.

After a page advance request is received in block 1808, the technique 1800 may proceed to block 1810, where the biometric monitoring device may determine the sequential display order for a plurality of data display pages. The biometric monitoring device may, for example, obtain the sequential display order from the above-mentioned look-up table or circular shift register. In some implementations, the biometric monitoring device may not manage the sequential display order as a pre-determined list or array, but may instead re-calculate the sequential display order at the time each page advance request is received.

The sequential display order determined in block 1810 may change depending on the outcome of block 1806. If block 1806 causes the biometric monitoring device to modify the sequential display order consonant with the first first environmental or contextual state, the modified sequential display order may be referenced in block 1810.

After determining the sequential display order in block 1810, the display may be caused to advance to the next data display page in the sequential display order after the currently-displayed data display page. After the data display page has been advanced, the technique may return to block 1808 and wait for another page advance request to be received. In some implementations, the technique may return to block 1808 prior to causing the data display page to be advanced, allowing several page advance requests to be queued up. Each queued-up page advance request may cause the biometric monitoring device to advance to a subsequent data display page.

It is to be understood that blocks 1802 through 1806 and blocks 1808 through 1812 may be performed concurrently, and that the sequential display order used to determine which data display page is to be displayed next in block 1812 may be influenced by the modifications to the sequential display order performed in block 1806. Moreover, the sequential display order may, in some implementations, change between successive page advance requests based on the modifications made in block 1806. In some other implementations, however, the modified sequential display order may not be provided for use in block 1810 immediately. For example, the modified sequential display order may only be provided after the current sequential display order has been cycled through from start to finish, or only after the display has been automatically powered down to conserve power.

Figure 19:
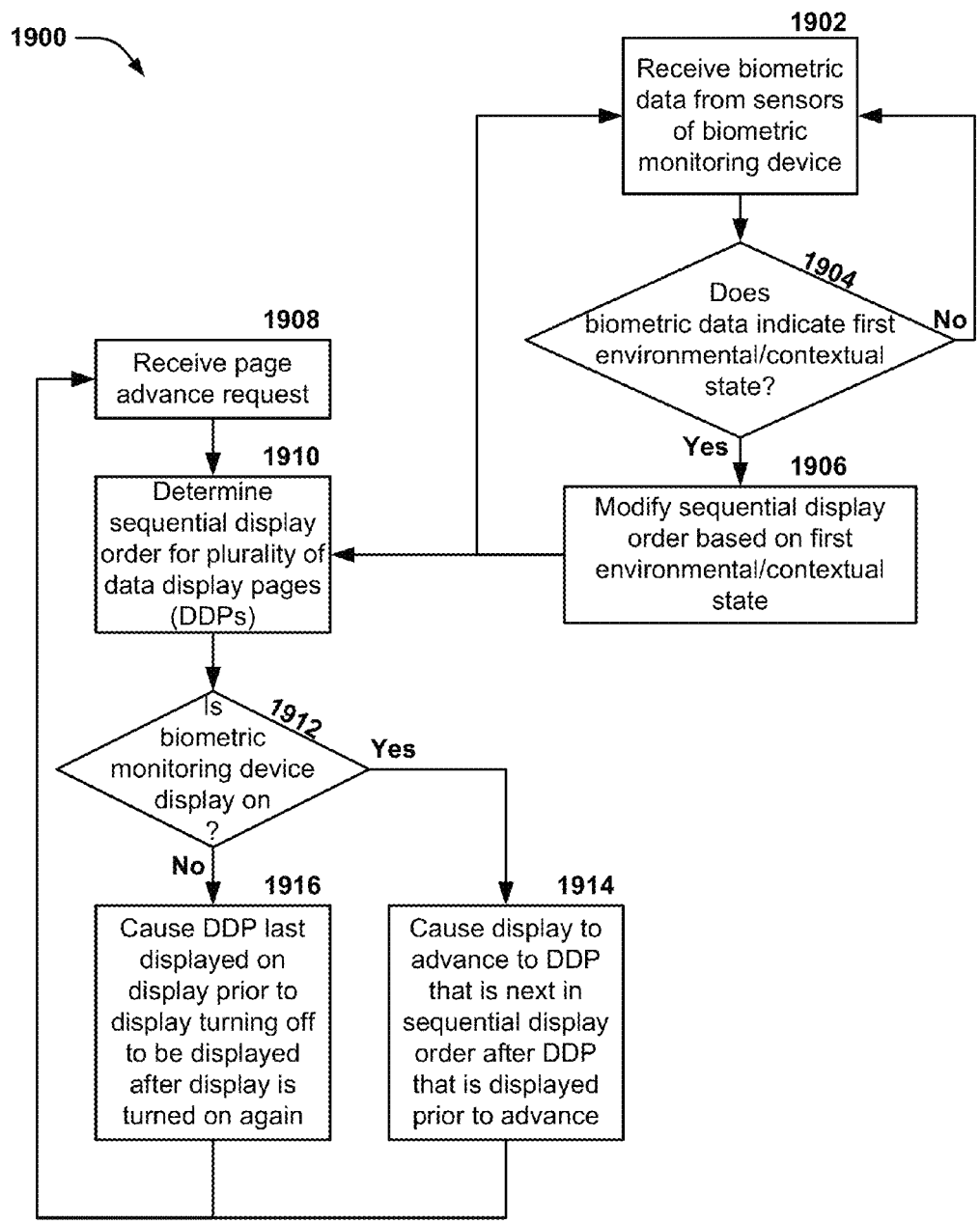
FIG. 19 depicts a flow diagram of a further technique for modifying the sequential display order of an example biometric monitoring device.

FIG. 19 depicts a flow diagram of a further technique for modifying the sequential display order of an example biometric monitoring device.

In FIG. 19, the technique 1900 may begin in block 1902 with the receipt of biometric data from biometric sensors of a biometric monitoring device. The biometric data may be evaluated in block 1904 to determine if the biometric data indicates a first environmental or contextual state. If the evaluation in block 1904 does not indicate a first environmental or contextual state, then the technique may return to block 1902 and await further biometric data.

If the evaluation in block 1904 does cause the biometric monitoring device to enter the first environmental or contextual state, the sequential display order of data display pages of the biometric monitoring device may be modified in block 1906 based on the first environmental or contextual state. This may occur in a manner similar to that discussed above with respect to block 1806.

While blocks 1902 through 1906 are performed, blocks 1908 through 1916 may also be performed. In block 1908, a page advance request may be received by the biometric monitoring device, much as in block 1808. In block 1910, the sequential display order of the data display pages is determined. If block 1906 has been performed and the first environmental or contextual state is active, then the sequential display order may be as modified in block 1906.

In block 1912, the processor or processors of the biometric monitoring device may determine if the display of the biometric monitoring device used to display data display pages is on. If the display is determined to be on in block 1912, the processor or processors of the biometric monitoring device may, in block 1914, cause the display to advance to the data display page that is next in the sequential display order, as determined in block 1910, with respect to the currently-displayed data display page.

If the display is determined to be off in block 1912, the processor or processors of the biometric monitoring device may, in block 1916, cause the display to turn on again and to display the data display page that was displayed on the display on the most recent instance in which the display was turned off.

After either block 1914 or 1916 is performed, the technique may return to block 1908 and await a further page advance request. In some implementations, if multiple page advance requests are received such that the temporal spacing between page advance requests is less than a screen power-off delay that causes the display to be de-powered or placed in standby, the first page advance received may cause block 1916 to be performed, and each subsequent such page advance request may cause block 1914 to be performed. It is to be understood that, generally speaking, reference herein to the display being in an "off" state also refers to displays that are not off, but in a low-power standby mode where a reduced amount of display functionality is provided as compared with non-standby operation modes.

In some implementations, the display may be a non-illuminable display, e.g., an LCD display or a reflective display, and instead of turning on the display, a backlight or frontlight for the display may be turned on or off. In some such implementations, the display may also be turned off, and both the display and the backlight or frontlight may be turned on. In some further such implementations, the display may be turned on and, if a light sensor on the biometric monitoring device indicates that ambient light values are sufficiently low, the biometric monitoring device may also turn on a backlight or frontlight to assist in viewing the content on the display. As with FIG. 18, blocks 1902 through 1906 and blocks 1908 through 1916 may be performed concurrently, and the sequential display order used to determine which data display page is to be displayed next in block 1914 may be influenced by the modifications to the sequential display order performed in block 1906. It is also to be understood that the relative order of the operations represented in blocks 1902 through 1916 (as well as the blocks of other techniques described herein) may be somewhat re-ordered from the order shown. For example, block 1910 may be performed between block 1912 and block 1914, instead of before block 1912, without affecting the overall functionality of the technique 1900. Such alternate implementations are also considered to be within the scope of this disclosure.

Figure 20:
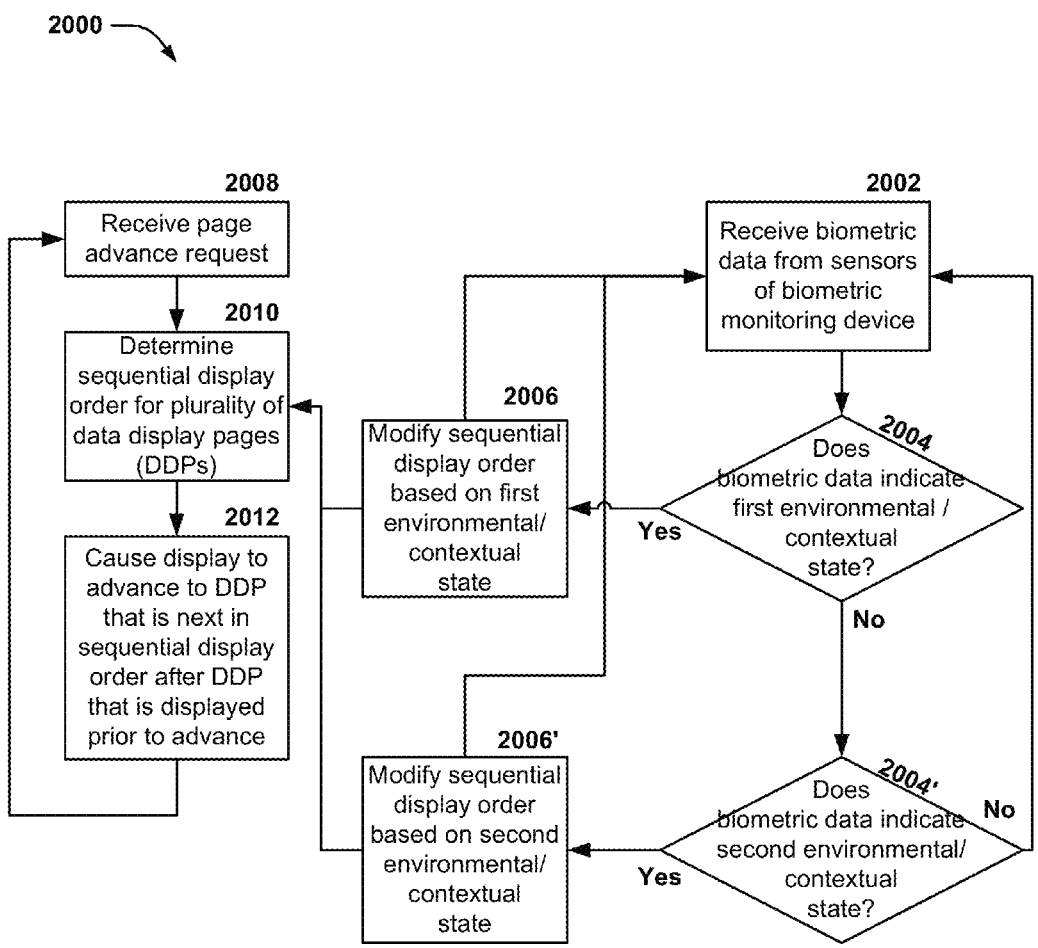
FIG. 20 depicts a flow diagram of another technique for modifying the sequential display order of an example biometric monitoring device.

FIG. 20 depicts a flow diagram of another technique for modifying the sequential display order of an example biometric monitoring device.

In FIG. 20, the technique 2000 may begin in block 2002 with the receipt of biometric data from biometric sensors of a biometric monitoring device. The biometric data may be evaluated in block 2004 to determine if the biometric data indicates a first environmental or contextual state. If the evaluation in block 2004 does not indicate that the first environmental or contextual state to be active, then the technique may proceed to block 2004' to determine if the biometric data indicates whether a second environmental or contextual state is indicated.

For example, if the biometric data indicates that the wearer of the biometric monitoring device is climbing stairs, e.g., an altimeter sensor indicates that the wearer is changing altitude at a rate that is consistent with climbing stairs and accelerometers indicate that the wearer is moving up and down consistent with a person's gait while climbing stairs, the biometric monitoring device determine that a first environmental or contextual state associated with stair climbing is active. If the biometric data instead indicates that that the wearer of the biometric monitoring device is running, e.g., accelerometers in the biometric monitoring device indicate that the wearer is experiencing accelerations consistent with running, then the biometric monitoring device may determine that the first environmental or contextual state is not indicated and may instead determine that a second environmental or contextual state is indicated. If the biometric data does not indicate that any environmental or contextual state is active, then the technique may return to block 2002 and await further biometric data. It is to be understood that there may be additional blocks 2004 (and 2006) for third, fourth, . . . $n^{th}$ environmental or contextual states rather than just the two environmental or contextual states shown.

If the biometric data causes the biometric monitoring device to enter the first environmental or contextual state in block 2004, then the technique may proceed to block 2006. In block 2006, the sequential display order may be modified based on the first environmental or contextual state. For example, if the first environmental or contextual state is associated with stair climbing, then the sequential display order may be modified to cause a "total stair flights climbed today" data display page to be first in the sequential display order, followed by a "contiguous stair flights currently climbed" data display page, followed by a data display page showing a graphic of a recognizable object that gives an indication of the magnitude of the elevation change, e.g., if the biometric data indicates an elevation change of two stories, a giraffe might be shown, whereas if the biometric data indicates an elevation change of five stories, a tree might be shown. Other data display pages, e.g., a "clock" data display page, a "steps taken" data display page, and a "calories burned" data display page, may be included in the sequential display order after the three data display pages relating to stair climbing. The modification of the sequential display order may involve including data display pages that may not be included in the sequential display order for other environmental or contextual states. For example, the "total stair flights climbed today" data display page may ordinarily be included in the sequential display order for a default device state or default activity state, but the "contiguous stair flights currently climbed" data display page, as well as the graphic-based data display page indicating the elevation change magnitude, may generally not be included in the sequential display order for the default device state or default activity state. Such data display pages may, however, be added to the sequential display order based on the first environmental or contextual state being active, e.g., if the first environmental or contextual state is associated with stair climbing.

If the biometric data causes the biometric monitoring device to enter the second environmental or contextual state in block 2004', then the technique may proceed to block 2006'. In block 2006', the sequential display order may be modified based on the second environmental or contextual state. For example, if the second environmental or contextual state is associated with running, then the sequential display order may be modified to cause a "running distance" data display page to be first in the sequential display order, followed by a "average miles per hour" data display page, followed by a data display page showing a graphic of a recognizable object that gives an indication of how fast the wearer of the biometric monitoring device is running, e.g., if the biometric data indicates that the wearer is running at a pace of 6 mph, a turtle or snail may be shown, whereas if the biometric data indicates that the wearer is running at a pace of 10 mph, a rabbit may be shown. Other data display pages, e.g., a "clock" data display page, a "steps taken" data display page, and a "calories burned" data display page, may be included in the sequential display order after the three data display pages relating to running.

While blocks 2002 through 2006/2006' are performed, blocks 2008 through 2016 may also be performed. In block 2008, a page advance request may be received by the biometric monitoring device, much as in block 1808. In block 2010, the sequential display order of the data display pages is determined. If block 2006 has been performed and the biometric monitoring device is in the first environmental or contextual state, then the sequential display order may be as modified in block 2006. If block 2006' has been performed and the biometric monitoring device is in the second environmental or contextual state, then the sequential display order may be as modified in block 2006'.

In block 2012, the processor or processors of the biometric monitoring device may cause the display to advance to the data display page that is next in the sequential display order, as determined in block 2010, with respect to the currently-displayed data display page.

After block 2012 is performed, the technique may return to block 2008 and await a further page advance request. In some implementations, blocks 2008 through 2012 may be replaced with operations similar to those represented in blocks 1908 through 19018.

As with FIG. 18, blocks 2002 through 2006 and blocks 2008 through 2012 may be performed concurrently, and the sequential display order used to determine which data display page is to be displayed next in block 2012 may be influenced by the modifications to the sequential display order performed in blocks 2006 or 2006'.

In various implementations, a biometric monitoring device may determine that an environmental or contextual state or states from a multitude of different environmental or contextual states is active, and may modify the sequential display order to display data display pages with data that is predetermined as being pertinent to the environmental or contextual state that is active.

For example, if the first environmental or contextual state indicates that an ambulatory motion state is active, then the sequential display order may be modified to include data display pages that display content that includes data such as step count since the first contextual or environmental state was determined, running pace, miles per hour, kilometers per hour, distance run since the first contextual or environmental state was determined, stairs climbed since the first contextual or environmental state was determined, elevation change since the first contextual or environmental state was determined, current elevation, time elapsed since the first contextual or environmental state was determined, current heart rate, current heart rate zone, calories burned, calories burned since the first contextual or environmental state was determined, and/or combinations thereof.

In some such implementations, the biometric monitoring device may determine that the ambulatory motion state is an ambulatory motion state such as a walking state, a running state, a hiking state, an interval training state, or a treadmill state based on the biometric data.

In some implementations, the biometric monitoring device may determine that a running state is active based on the biometric data indicating a step rate above a first threshold. In some other or additional implementations, the biometric monitoring device may determine that a running state is active based on the biometric data indicating a speed above 4 miles per hour and below 20 miles per hour coupled with the biometric data indicating that the person is engaged in ambulatory motion.

In some implementations, the biometric monitoring device may determine that a walking state is active based on the biometric data indicating a step rate below the first threshold. In some other or additional implementations, the biometric monitoring device may determine that a walking state is active based on the biometric data indicating a non-zero speed below 4 miles per hour coupled with the biometric data indicating that the person is engaged in ambulatory motion.

In another example, if the first environmental or contextual state indicates that a water sports state is active, then the sequential display order may be modified to include data display pages that display content that includes data such as laps since the first contextual or environmental state was determined, current stroke type, stroke count of current stroke type, lap time, swimming efficiency, current heart rate, current heart rate zone, calories burned, calories burned since the first contextual or environmental state was determined, and/or combinations thereof.

In some such implementations, the biometric monitoring device may determine that the water sports state is an indoor swimming state or an outdoor swimming state based on the biometric data.

In another example, if the first environmental or contextual state indicates that a aerobic exercise machine state is active, then the sequential display order may be modified to include data display pages that display content that includes data such as duration since the first contextual or environmental state was determined, current heart rate, current heart rate zone, calories burned, calories burned since the first contextual or environmental state was determined, and/or combinations thereof.

In some such implementations, the biometric monitoring device may determine that the aerobic exercise machine state is an elliptical machine state, a stair climbing machine state, a stationary bicycle state, a spinning machine state, or a rowing machine state based on the biometric data.

In yet another example, if the first environmental or contextual state indicates that an aerobic exercise state is active, then the sequential display order may be modified to include data display pages that display content that includes data such as duration since the first contextual or environmental state was determined, current heart rate, current heart rate zone, calories burned, calories burned since the first contextual or environmental state was determined, and/or combinations thereof.

In some such implementations, the biometric monitoring device may determine that the aerobic exercise state is a Zumba™ state, an aerobic dance state, a kick boxing state, or a jump rope state based on the biometric data.

In yet another example, if the first environmental or contextual state indicates that a resistance training state is active, then the sequential display order may be modified to include data display pages that display content that includes data such as number of repetitions since the first contextual or environmental state was determined, number of sets since the first contextual or environmental state was determined, time between sets, current heart rate, current heart rate zone, calories burned, calories burned since the first contextual or environmental state was determined, lifting form, and/or combinations thereof.

In some such implementations, the biometric monitoring device may determine that the resistance training state is a bicep curl state, a benchpress state, a military press state, a pull-ups state, a push-ups state, a set-ups state, or a squats state based on the biometric data.

In yet a further example, if the first environmental or contextual state indicates that a resting state is active, then the sequential display order may be modified to include data display pages that display content that includes data such as sleep quality, number of times awoken, sleep stage, duration since the first contextual or environmental state was determined, quiescent sleep time, restless sleep time, ambulatory sleep time, overall time elapsed since the first contextual or environmental state was determined, and/or combinations thereof.

In some such implementations, the biometric monitoring device may determine that the resting state is a sleeping state, a reclining state, a sitting state, an office work state, a reading state, a watching-TV state, or a leisure state based on the biometric data.

A rest state may, for example, be determined to be a sleep state based on the biometric data collected by the biometric monitoring device indicating that the wearer of the biometric monitoring device is substantially inactive for a first time period. In some implementations, the biometric monitoring device may also determine that the first time period includes time between the hours of 9:00 PM and 6:00 AM as a further indicator that the biometric data indicates a sleep state.

Figure 21:
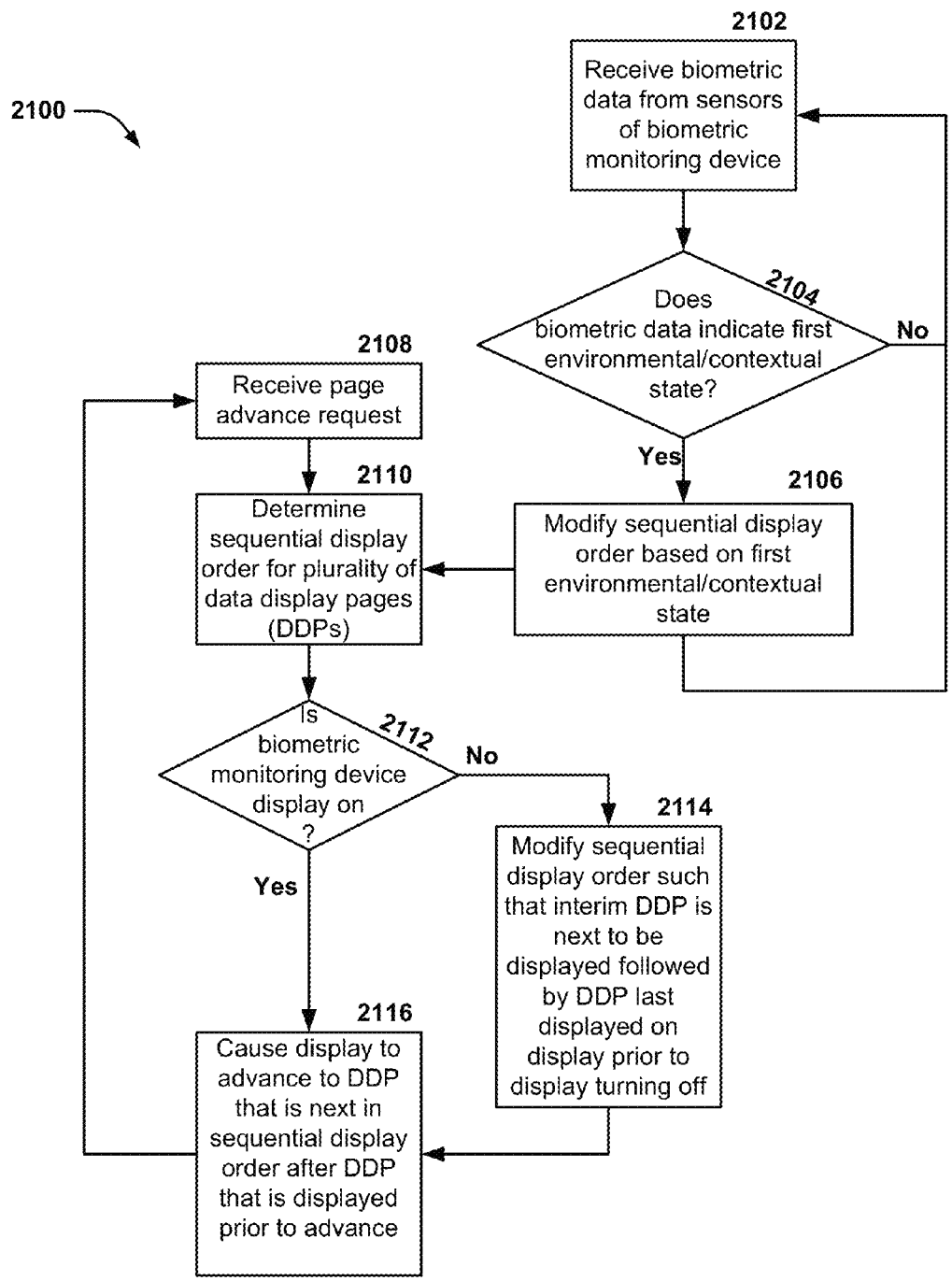
FIG. 21 depicts a flow diagram of an additional technique for modifying the sequential display order of an example biometric monitoring device.

FIG. 21 depicts a flow diagram of an additional technique for modifying the sequential display order of an example biometric monitoring device.

In FIG. 21, the technique 2100 may begin in block 2102 with the receipt of biometric data from biometric sensors of a biometric monitoring device. The biometric data may be evaluated in block 2104 to determine if the biometric data causes a first environmental or contextual state to be active. If the evaluation in block 2104 does not cause a first environmental or contextual state to be active on the biometric monitoring device, then the technique may return to block 2102 and await further biometric data.

While blocks 2102 through 2106 are performed, blocks 2108 through 2114/2116 may also be performed. In block 2108, a page advance request may be received by the biometric monitoring device. In block 2110, the sequential display order may be determined. The sequential display order may, for example, be modified per the actions of block 2106. The technique may then proceed to block 2112, where the processor or processors of the biometric monitoring device may determine if the display of the biometric monitoring device is in an off state.

If a determination is made in block 2112 that the display is in an off state, then the sequential display order may be further modified in block 2114 such that one or more interim data display pages are next in the sequential display order. The sequential display order may further be modified such that the one or more interim data display pages are followed by the data display page that was last displayed on the display prior to the display entering the off state. In some implementations, however, the sequential display order may instead be further modified such that the non-interim data display page that would have been displayed next if the sequential display order had not been modified to include the interim data display pages is displayed next after the interim data display page or interim data display pages. In some cases, a splash page may be used instead of an interim data display page. In some implementations, interim data display pages may include "low battery" data display pages, "low memory" data display pages, "sync-in-progress" data display pages, etc. that may be used to communicate biometric monitoring device system status to the user.

Another example of an interim data display page is a "message" or "reminder" data display page. For example, if the biometric monitoring device receives an indication of a text message, a "tweet," a comment on a social networking site, or an email, this might cause a "message received" state to be active on the biometric monitoring device. When the "message received" state is active, the device state may alter and cause the sequential display order to be modified to cause a "message" data display page to be inserted into the sequential display order such that the "message" data display page is the next data display page to be displayed when a page advance request is received. The "message" data display page may display some content associated with the received message. This may be as simple as an icon indicating that the message was received, e.g., a graphic of an envelope, or may include additional data, e.g., the name of the sender, an excerpt from the message, etc.

Yet another example of an interim data display page is an "achievement indicator" that may be associated with an "achievement reached" state. For example, the biometric monitoring device may detect that the wearer has exceeded a predefined goal or achievement threshold, e.g., 10,000 steps taken in one day, and may, responsive to such an event, enter an "achievement reached" state. This may cause the sequential display order to be modified to cause an "achievement award" data display page to be the next data display page in the sequential display order to be displayed responsive to receipt of a page advance request. Thus, if the display is off when the page advance request is received, the display may turn on and display the "achievement award" data display page. After a further page advance request is received to cause the display to advance to the next data display page in the sequential display order, the "achievement reached" state may be inactivated and the "achievement award" data display page may be removed from the sequential display order. In other implementations, the "achievement reached" state may stay active for a predetermined period of time before becoming inactivated, e.g., 1 minute after a subsequent page advance request is received.

The technique may then proceed from block 2114 to block 2116, where the processor or processors of the biometric monitoring device may cause the display to advance to the data display page that is next in the sequential display order after the data display page that was most recently displayed on the data display page. If a determination is made in block 2112 that the display of the biometric monitoring device is already on, then block 2116 may be performed without performing block 2114.

FIGS. 22A and 22B provide examples of sequential display orders. In FIG. 22A, a table is provided that lists a sequential display order for five data display pages in the right-most column. The left column indicates the display status of the listed data display pages. As can be seen, the "distance traveled" data display page is currently displayed, and the "calories burned" data display page is the data display page that will be displayed next responsive to receipt of a page advance request, e.g., such as may be done in block 2116.

FIG. 22B depicts the same sequential display order as shown in FIG. 22A, but modified to insert two interim data display pages into the sequential display order, such as may be done in block 2114.

For example, a biometric monitoring device may be displaying the data display pages listed in the sequential display order of FIG. 22A. The user of the biometric monitoring device may cause the display to cycle through the five listed data display pages—as long as the display does not turn off, each successive page advance request by the user may cause the biometric monitoring device to display the next data display page listed in the sequential display order with respect to the data display page currently displayed. If the last data display page in the sequential display order is displayed, then the next data display page that is displayed responsive to a page advance request may be the first data display page in the sequential display order, as indicated by the arrow on the right side of the table. If the display of the biometric monitoring device is currently displaying the "distance traveled" data display page and a page advance request is received, then a processor or processors of the biometric monitoring device may cause the display to display the "next" data display page in the sequential display order, i.e., the "calories burned" data display page.

If a page advance request is received while the display of the biometric monitoring device is in an off state, however, then the processor or processors of the biometric monitoring device may modify the sequential display order as shown in FIG. 22B by inserting, in this case, two interim data display pages into the sequential display order just after the data display page that was last displayed on the display before the display entered the off state. The interim display pages, as shown in this example, may be duplicate instances of other data display pages in the sequential display order. For example, the sequential display order may be modified such that an interim "clock" data display page is the next data display page that is displayed responsive to receipt of a page advance request while the display is off, and such that an interim "distance traveled" data display page—which was the data display page that was displayed by the display when the display entered the off state—is the next data display page that is displayed responsive to the next page advance request to be received after the page advance request received while the display was off.

After one or more interim data display pages have been displayed, the sequential display order may be further modified to remove the displayed interim data display pages from the sequential display order. For example, after the interim "clock" data display page is displayed, it may be removed from the sequential display order. Thus, if all of the data display pages in the sequential display order are advanced through without the display turning off, then both interim data display pages shown may be removed from the sequential display order. In effect, this causes the interim data display pages to be shown only once while the display is in an on state—after the initial display of the interim data display pages, the biometric monitoring device will revert to displaying the data display pages as shown in the sequential display order of FIG. 22A.

Figure 10:
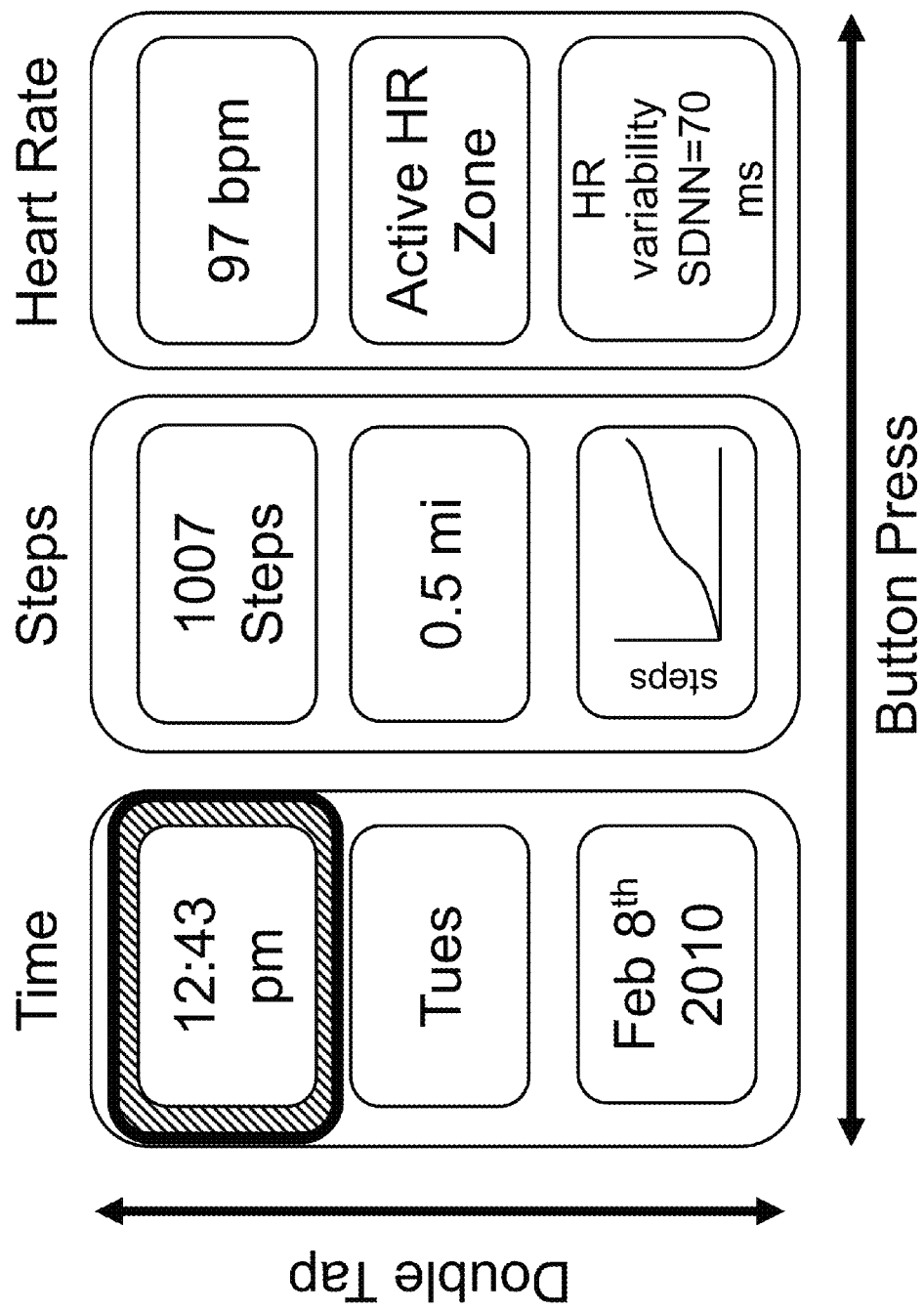
FIG. 10 depicts data display pages and associated data display subpages for an example biometric monitoring device.

As mentioned with respect to FIGS. 10 through 12, in some implementations, some data display pages may be represented by any of a plurality of different data display subpages. For example, FIG. 10 depicts three data display pages—a "time" data display page, a "steps" data display page, and a "heart rate" data display page. Each data display page shown may have, in this example, three data display subpages. For example, the "time" data display page has a "12-hour time" data display subpage ("12:43 pm"), a "weekday" data display subpage "Tues"), and a "date" data display subpage ("Feb 8$^{th}$ 2010"); the "steps" data display page has a "steps taken" data display subpage ("1007 steps"), a "distance" data display subpage ("0.5 mi"), and a "steps v. time" data display subpage (a two-axis data plot); and the "heart rate" data display page may have a "beats per minute" data display subpage ("97 bpm"), a "heart rate zone" data display subpage ("Active HR Zone"), and a "heart rate variability" data display subpage ("HR variability SDNN=70 ms").

In FIGS. 10 through 11, the data display pages/data display subpages shown are examples of data display pages/data display subpages that may be shown on a display of a biometric monitoring device. Such a biometric monitoring device may be capable of differentiating between at least two different types of input. In response to receiving the first type of input, e.g., a button press, the biometric monitoring device may cause the display to advance through the sequential display order and to display, for each data display page, the data display subpage that is indicated as representing the data display page. For example, the "12-hour time" data display subpage is currently representing the "time" data display page in FIG. 10, and when a user advances to the "time" data display page, the "12-hour time" data display subpage would then be displayed by the display to represent the "time" data display page. Correspondingly, when the user then advances to the "steps" data display page, e.g., by pressing the button again, the "steps taken" data display subpage may be displayed to represent the "steps" data display page.

In response to receipt of the second type of input, e.g., a double tap of an object such as a fingertip on the housing of the biometric monitoring device, the processor or processors of the biometric monitoring device may cause the display to advance to the next data display subpage in a sequential subpage display order for the currently-displayed data display page. For example, if the "steps" data display page, represented by the "steps taken" data display subpage, is currently shown on the display of a biometric monitoring device and the biometric monitoring device receives the second type of input, e.g., a double-tap on the housing of the biometric monitoring device, the processor or processors of the biometric monitoring device may cause the display to advance to the "distance" data display subpage. Thus, the "steps" data display page is still shown/represented on the display of the biometric monitoring device, but the actual content that is displayed by the "steps" data display page is governed by the data display subpage. Typically, the content of the various data display subpages that may represent a data display page is related to the data display page that the data display subpages represent.

Figure 23:
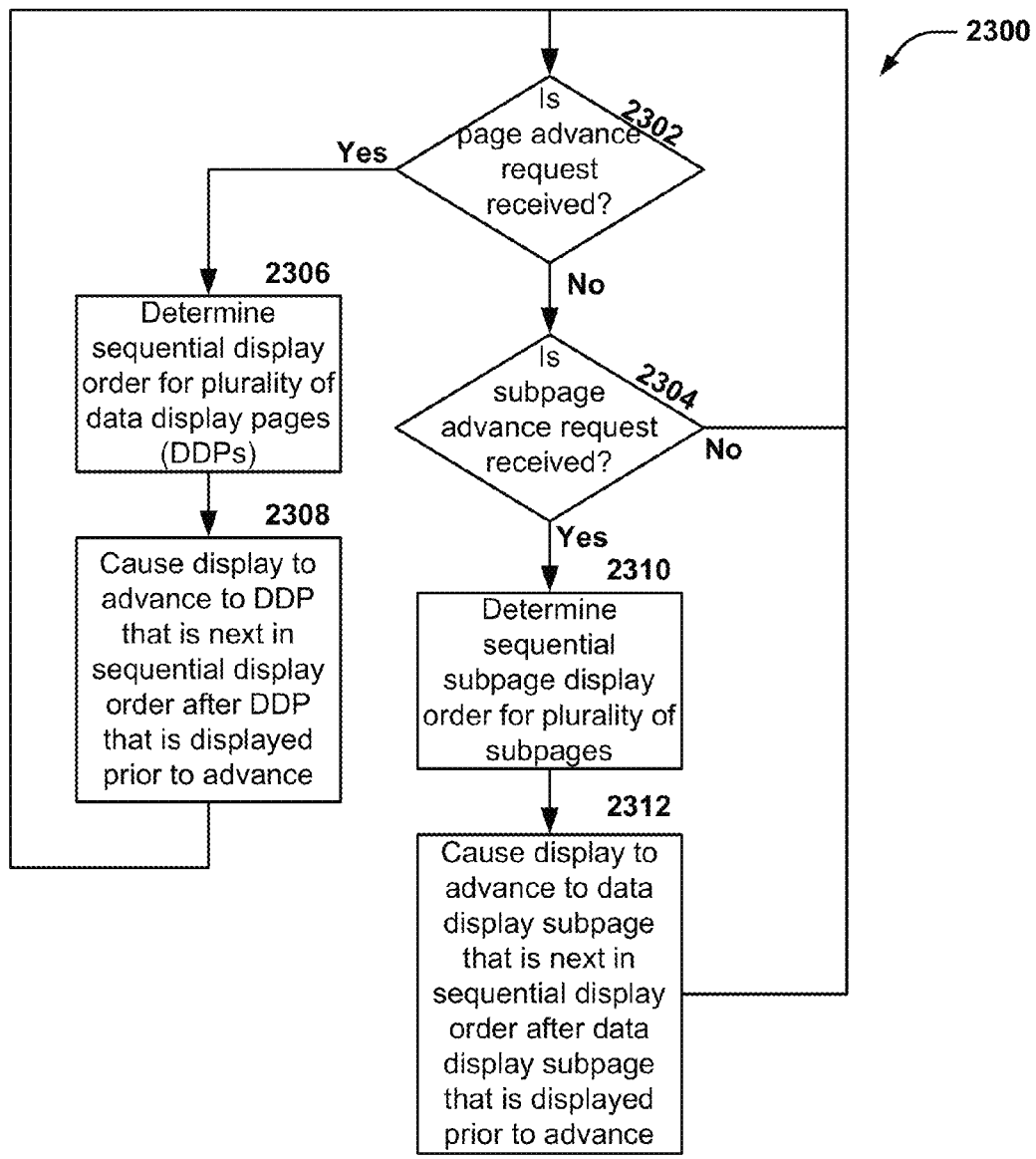
FIG. 23 depicts a flow diagram of a technique for navigating data display pages and data display subpages.

FIG. 23 depicts a flow diagram of a technique for navigating data display pages and data display subpages.

Technique 2300 in FIG. 23 begins in block 2302 with a determination as to whether a page advance request is received by the processor or processors of a biometric monitoring device. If the determination is made in block 2302 that a page advance request has been received, then the technique may proceed to block 2306. In block 2306, the sequential display order for a plurality of data display pages may be determined. This may occur in a manner similar to that discussed above with respect to other implementations described herein, e.g., such as the manner described with respect to FIG. 18. The technique may then continue to block 2308, where the processor or processors may cause the display to advance to the data display page that is next in the sequential display order with respect to the data display page that is displayed when the page advance request is received.

If a determination is made in block 2302 that a page advance has not been received, a determination may then be made in block 2304 as to whether a subpage advance request has been received. If the determination is made in block 2304 that a subpage advance request has been received, then the technique may proceed to block 2310. In block 2310, the sequential subpage display order for a plurality of data display subpages may be determined. This may occur in a manner similar to that discussed above with respect data display page sequential display orders in other implementations described herein, e.g., in a manner similar to that described with respect to data display page sequential display order as described with respect to FIG. 18. The technique may then continue to block 2312, where the processor or processors may cause the display to advance to the data display subpage that is next in the sequential subpage display order with respect to the data display subpage that is displayed when the subpage advance request is received.

If a subpage advance request is received while the data display subpage that is last in the sequential subpage display order is displayed, then the data display subpage that is first in the sequential subpage display order may be treated as the next data display subpage in the sequential subpage display order. Alternatively, the sequential subpage display order may reverse.

If a determination is made in block 2302 that a page advance has not been received, then the technique may return to block 2302 and be ready to receive potential page advance requests and subpage advance requests. Similarly, the technique may also return to block 2302 after the actions in blocks 2308 or 2312 are completed.

Generally speaking, the techniques and functions outlined above may be implemented in a biometric monitoring device as machine-readable instruction sets, either as software stored in memory, as application-specific integrated circuits, field-programmable gate-arrays, or other mechanisms for providing system control. Such instruction sets may be provided to a processor or processors of a biometric monitoring device to cause the processor or processors to control other aspects of the biometric monitoring device to provide the functionality described above.

Unless the context (where the term "context" is used per its typical, general definition) of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein.

There are many concepts and implementations described and illustrated herein. While certain features, attributes and advantages of the implementations discussed herein have been described and illustrated, it should be understood that many others, as well as different and/or similar implementations, features, attributes and advantages of the present inventions, are apparent from the description and illustrations. As such, the above implementations are merely exemplary. They are not intended to be exhaustive or to limit the disclosure to the precise forms, techniques, materials and/or configurations disclosed. Many modifications and variations are possible in light of this disclosure. It is to be understood that other implementations may be utilized and operational changes may be made without departing from the scope of the present disclosure. As such, the scope of the disclosure is not limited solely to the description above because the description of the above implementations has been presented for the purposes of illustration and description.

Importantly, the present disclosure is neither limited to any single aspect nor implementation, nor to any single combination and/or permutation of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein.

What is claimed is:

1. An apparatus comprising:

two or more biometric sensors including at least one accelerometer and at least one other biometric sensor;

a display;

at least one processor; and a memory, wherein:

the memory, the at least one processor, the two or more biometric sensors, and the display are communicatively connected with one another, and the memory stores computer-executable instructions for controlling the at least one processor to:

determine a sequential display order for a plurality of data display pages;

receive one or more page advance requests;

cause, for each received page advance request, the display to advance to the data display page that is next in the sequential display order with respect to the data display page that is displayed on the display prior to the advance;

receive biometric data from the two or more biometric sensors, the biometric data including biometric data from the at least one accelerometer and from the at least one other biometric sensor;

determine that the biometric data from the at least one accelerometer and from the at least one other biometric sensor indicates, at least in part, a first contextual or environmental state, wherein the biometric data that is determined to indicate, at least in part, the first contextual or environmental state is not biometric data that is indicative of a deliberate user request or interaction with the apparatus; and modify the sequential display order of the data display pages based on the determination that the biometric data from the at least one accelerometer and from the at least one other biometric sensor indicates, at least in part, the first contextual or environmental state in conjunction with a determination that a mode of the apparatus is active to produce a first sequential display order, wherein:

the modification of the sequential display order is defined, at least in part, by a set of heuristics associated with the mode of the apparatus that is active, an interpretation of the biometric data from the two or more biometric sensors is impacted by the mode of the apparatus, and the first environmental or contextual state is associated with an activity of a user.

2. The apparatus of claim 1, wherein when the data display page that is displayed on the display prior to the advance is the last data display page in the sequential display order, the data display page that is first in the sequential display order is treated as the data display page that is next in the sequential display order.

3. The apparatus of claim 1, wherein the sequential display order reverses when the data display page that is displayed on the display prior to the advance is the last data display page in the sequential display order.

4. The apparatus of claim 1, wherein the first contextual or environmental state is associated with activities selected from the group consisting of walking, running, stair climbing, bicycling, swimming, resting, working, being at home, being in transit in a car or other powered vehicle, driving, and being in a meeting.

5. The apparatus of claim 1, wherein the page advance requests are generated responsive to data collected from the two or more biometric sensors.

6. The apparatus of claim 1, further comprising:
a page advance input separate from the two or more biometric sensors, wherein:
the memory, the at least one processor, the two or more biometric sensors, the page advance input, and the display are communicatively connected with one another, and the memory and/or at least one processor are configured to receive the one or more page advance requests responsive to corresponding one or more activations of the page advance input.

7. The apparatus of claim 6, wherein the page advance input is a button.

8. The apparatus of claim 7, wherein the apparatus is free of buttons except for the page advance input and wherein the two or more biometric sensors and the page advance input are the only mechanisms in the apparatus that are capable of detecting tactile or audio input to the apparatus.

9. The apparatus of claim 1, wherein the memory further stores computer-executable instructions for controlling the at least one processor to:
determine that the biometric data indicates, at least in part, a second contextual or environmental state different from the first contextual or environmental state; and
modify the sequential display order of the data display pages based on the determination that the biometric data indicates the second contextual or environmental state to produce a second sequential display order, wherein the first sequential display order and the second sequential display order are different.

10. The apparatus of claim 1, wherein the memory further stores computer-executable instructions for controlling the at least one processor to:
modify the sequential display order of the data display pages by adding or removing a data display page from the plurality of data display pages based on the determination that the biometric data indicates the first contextual or environmental state.

11. The apparatus of claim 1, wherein the memory further stores computer-executable instructions for controlling the at least one processor to:
determine that the first contextual or environmental state is associated with a first user-specified sequential display order; and
modify the sequential display order of the data display pages to correspond to the first user-specified sequential display order to produce the first sequential display order.

12. The apparatus of claim 11, further comprising:
a communications interface, wherein the memory, the at least one processor, the two or more biometric sensors, the page advance input, the display, and the communications interface are communicatively connected with one another, and
the memory and/or at least one processor are configured to receive data indicating the user-specific sequential display order via the communications interface and from a device external to the apparatus.

13. The apparatus of claim 1, wherein the memory further stores computer-executable instructions for controlling the at least one processor to:
determine that at least one of the data display pages in the plurality of data display pages has a user-specified priority; and
modify the sequential display order of the data display pages based on the determination that the biometric data indicates the first contextual or environmental state and the user-specified priority of the at least one data display page to produce the first sequential display order.

14. The apparatus of claim 1, wherein the memory further stores computer-executable instructions for controlling the at least one processor to:
determine that the display is turned off when a page advance request is received;
determine the data display page displayed on the display when the display was turned off;
cause the display to turn on responsive to the page advance request; and
modify the sequential display order such that the data display page that was displayed on the display when the display was turned off is displayed on the display after the display is turned on again and responsive to the page advance request.

15. The apparatus of claim 1, wherein the memory further stores computer-executable instructions for controlling the at least one processor to:
determine that the display is turned off when a page advance request is received;
determine the data display page displayed on the display when the display was turned off;
cause the display to turn on again;
modify the sequential display order such that at least one interim data display page different from the data display page that was displayed on the display when the display was turned off is the first data display page or pages displayed on the display after the display is turned on again and responsive to the page advance request; and
modify the sequential display order such that the data display page that was displayed on the display when the display was turned off is the next data display page that is displayed on the display after the at least one interim data display page is displayed.

16. The apparatus of claim 15, wherein the at least one interim data display page includes a data display page showing a time-of-day clock.

17. The apparatus of claim 15, wherein the at least one interim data display page includes a data display page selected from the group consisting of: a data display page showing a low battery indicator, a data display page showing a low memory indicator, and a data display page showing a sync-in-progress indicator.

18. The apparatus of claim 15, wherein the at least one interim data display page includes a data display page showing user achievement indicator that indicates that one or more quantities based on data provided by the two or more biometric sensors have exceeded a pre-defined threshold, the user achievement indicator in addition to displaying the one or more quantities.

19. The apparatus of claim 15, further comprising:
a communications interface configured to communicate with a device external to the apparatus, wherein:
  the memory, the at least one processor, the two or more biometric sensors, the display, and the communications interface are communicatively connected with one another, and
  the memory further stores computer-executable instructions for controlling the at least one processor to:
    receive a message from the device external to the apparatus via the communications interface, and
    display a data display page on the display indicating at least some content associated with the message as an interim data display page of the at least one interim data page.

20. The apparatus of claim 19, wherein:
the message is a text message, tweet, social networking website comment, or email.

21. The apparatus of claim 19, wherein:
the message includes data indicating a user achievement indicator that indicates that one or more quantities based on data provided by another two or more biometric sensors external to the apparatus have exceeded a pre-defined threshold.

22. The apparatus of claim 14, wherein:
the plurality of data display pages includes a first subset of at least one data display page, and
the memory further stores computer-executable instructions for controlling the at least one processor to:
  cause the at least one data display page of the first subset to be displayed on the display after the display is turned on again regardless of whether the data display page that was displayed on the display when the display was turned off is in the first subset.

23. The apparatus of claim 1, wherein:
at least one of the data display pages in the plurality of data display pages has a plurality of data display subpages, wherein each of the data display subpages in the plurality of data display subpages displays a metric that is based on the biometric data received from at least one of the two or more biometric sensors when that data display subpage is displayed, and
the memory further stores computer-executable instructions for controlling the at least one processor to:
  determine a sequential subpage display order for the plurality of data display subpages,
  receive one or more subpage advance requests,
  cause, for each received subpage advance request received when the data display subpage having the plurality of data display subpages is displayed, the display to advance to the data display subpage that is next in the sequential subpage display order with respect to the data display subpage that is displayed on the display prior to the advance, wherein when the data display subpage that is displayed on the display prior to the advance is the last data display subpage in the sequential subpage display order, the data display subpage that is first in the sequential subpage display order is treated as the data display subpage that is next in the sequential subpage display order, wherein the data display page having the data display subpage that is displayed on the display is represented by the data display subpage that is displayed on the display.

24. The apparatus of claim 23, wherein each data display subpage of the plurality of data display subpages presents data associated with the data page display having the data display subpages in different units, different formats, or a combination thereof.

25. A method comprising:
determining, by one or more processors of a biometric tracking device, a sequential display order for a plurality of data display pages;
receiving, by the one or more processors, one or more page advance requests;
causing, for each received page advance request, a display of the biometric tracking device to advance to the data display page that is next in the sequential display order with respect to the data display page that is displayed on the display prior to the advance;
receiving biometric data from two or more biometric sensors in communication with the biometric tracking device, the two or more biometric sensors including at least one accelerometer and at least one other biometric sensor and the biometric data including biometric data from the at least one accelerometer and from the at least one other biometric sensor;
determining, by the one or more processors, that the biometric data from the at least one accelerometer and from the at least one other biometric sensor indicates, at least in part, a first contextual or environmental state, wherein the biometric data that is determined to indicate, at least in part, the first contextual or environmental state is not biometric data that is indicative of a deliberate user request or interaction with the apparatus; and
modifying, by the one or more processors, the sequential display order of the data display pages to produce a first sequential display order based on the determination that the biometric data from the at least one accelerometer and from the at least one other biometric sensor indicates, at least in part, the first contextual or environmental state in conjunction with a determination that a mode of the apparatus is active, wherein:
  the modification of the sequential display order is defined, at least in part, by a set of heuristics associated with the mode of the apparatus that is active,
  an interpretation of the biometric data from the two or more biometric sensors is impacted by the mode of the apparatus, and
  the first environmental or contextual state is associated with an activity of a user.

26. The method of claim 25, wherein when the data display page that is displayed on the display prior to the advance is the last data display page in the sequential display order, the data display page that is first in the sequential display order is treated as the data display page that is next in the sequential display order.

27. The method of claim 25, wherein the sequential display order reverses when the data display page that is displayed on the display prior to the advance is the last data display page in the sequential display order.

* * * * *